United States Patent
Gonzalez et al.

(10) Patent No.: US 10,233,209 B2
(45) Date of Patent: Mar. 19, 2019

(54) INHIBITORS OF THE FARNESOID X RECEPTOR AND USES IN MEDICINE

(71) Applicants: The United States of America, as represented by the Secretary, Department of Health and Human Services, Washington, DC (US); The Penn State Research Foundation, University Park, PA (US)

(72) Inventors: Frank J. Gonzalez, Bethesda, MD (US); Changtao Jiang, Beijing (CN); Cen Xie, Rockville, MD (US); Andrew D. Patterson, State College, PA (US); Fei Li, Rockville, MD (US); James B. Mitchell, Damascus, MD (US); Shantu Amin, Union City, NJ (US); Dhimant Desai, Mechanicsburg, PA (US)

(73) Assignees: The United States of America, As represented by the Secretary, Department of Health and Human Services, Washington, DC (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/371,032

(22) Filed: Dec. 6, 2016

(65) Prior Publication Data
US 2017/0152283 A1 Jun. 1, 2017

Related U.S. Application Data

(62) Division of application No. 14/909,263, filed as application No. PCT/US2014/049460 on Aug. 1, 2014, now Pat. No. 9,540,415.

(60) Provisional application No. 62/004,436, filed on May 29, 2014, provisional application No. 61/861,109, filed on Aug. 1, 2013.

(51) Int. Cl.
*C07J 9/00* (2006.01)
*C07J 41/00* (2006.01)
*C07J 31/00* (2006.01)

(52) U.S. Cl.
CPC ........... *C07J 41/0061* (2013.01); *C07J 9/005* (2013.01); *C07J 31/006* (2013.01); *C07J 41/0055* (2013.01); *C07J 41/0066* (2013.01)

(58) Field of Classification Search
CPC ...... C07J 41/0061; C07J 9/005; C07J 31/006; C07J 41/0055; C07J 41/0066
USPC ....................................................... 514/119
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,010,056 A * | 4/1991 | Boghen ................ | A61K 9/0043 424/43 |
| 5,019,369 A | 5/1991 | Presant et al. | |
| 5,876,721 A * | 3/1999 | Alexander ............. | A61K 39/39 424/184.1 |
| 6,551,623 B1 * | 4/2003 | Rang ...................... | A61K 31/07 424/528 |
| 6,984,650 B2 | 1/2006 | Haffner et al. | |
| 2005/0054634 A1 | 3/2005 | Busch et al. | |
| 2008/0132519 A1 | 6/2008 | Martin et al. | |

FOREIGN PATENT DOCUMENTS

| CA | 2014545 C | 8/2001 |
|---|---|---|
| CN | 101891791 A | 11/2010 |
| WO | WO 87/02367 A2 | 4/1987 |
| WO | WO 90/00175 A1 | 1/1994 |

(Continued)

OTHER PUBLICATIONS

Angelakis et al., "The Increase of *Lactobacillus* Species in the Gut Flora of Newborn Broiler Chicks and Ducks Is Associated with Weight Gain," *PLoS One*, 5(5), e10463, 1-5 (2010).

(Continued)

*Primary Examiner* — Yevgeny Valenrod
(74) *Attorney, Agent, or Firm* — Leydig, Voit & Mayer, Ltd.

(57) ABSTRACT

Disclosed are inhibitors of the farnesoid X receptor, for example of formula (I), wherein $R^1$, $R^2$, $R^4$, X, Y, Z, m, and n are as defined herein, which are useful in treating or preventing obesity, type 2 diabetes/insulin resistance and non-alcoholic fatty liver disease in a mammal in need thereof. Also disclosed is a composition comprising a pharmaceutically suitable carrier and at least one compound of the invention, a method of method of inhibiting a farnesoid X receptor in a mammal, and a method of treating or preventing obesity in a mammal.

11 Claims, 84 Drawing Sheets

(56) References Cited

FOREIGN PATENT DOCUMENTS

| WO | WO 94/24147 A1 | 10/1994 |
|---|---|---|
| WO | WO 00/37077 A1 | 6/2000 |
| WO | WO 02/094865 A1 | 11/2002 |
| WO | WO 03/030612 A2 | 4/2003 |
| WO | WO 2009/136396 A2 | 11/2009 |
| WO | WO 2010/014836 A2 | 2/2010 |
| WO | WO 2011/022838 A1 | 3/2011 |

OTHER PUBLICATIONS

Barlow et al., "Obesity Evaluation and Treatment: Expert Committee Recommendations," *Pediatrics*, 102 (3), 1-11 (1998).
Beltowski et al. "Antioxidant treatment normalizes renal Na+,K+-ATPase activity in leptin-treated rats" *Pharma. Reports*, 57, 219-228 (2005).
Berber et al., "Tempol Reduces Bacterial Translocation After Ischemia/Reperfusion Injury in a Rat Model of Superior Mesenteric Artery Occlusion," *Surgery Today*, 39, 407-413 (2009).
Bhatia et al., "Non-alcoholic fatty liver disease: a new and important cardiovascular risk factor?" *Eur. Heart J.*, 33, 1190-1200 (2012).
Blankenberg et al., "Manipulation of FASTQ data with Galaxy," *Bioinformatics*, 26 (14), 1783-1785 (2010).
Browning et al., "Molecular mediators of hepatic steatosis and liver injury," *J Clin. Invest.*, 114 (2), 147-152 (2004).
Bruce et al., "Overexpression of Sphingosine Kinase 1 Prevents Ceramide Accumulation and Ameliorates Muscle Insulin Resistance in High-Fat Diet-Fed Mice," *Diabetes*, 61, 3148-3155 (2012).
Chavez et al., "A Ceramide-Centric View of Insulin Resistance," *Cell Metabolism*, 15, 585-594 (2012).
Cloarec et al., "Evaluation of the Orthogonal Projection on Latent Structure Model Limitations Caused by Chemical Shift Variability and Improved Visualization of Biomarker Changes in $^1$H NMR Spectroscopic Metabonomic Studies" *Anal. Chem.*, 77 (2), 517-526 (2005).
Dai et al., "Impact of Bile Acids on the Growth of Human Cholangiocarcinoma via FXR" *J. Hematol. Oncol.*, 4 (41), 1-8 (2011).
Database CA 1956:37341—Kobayashi, "Influence of bile salts on fat metabolism," 2 pages (1955).
Database CA 1960:119943—Hirata, "Influence of bile salts on carbohydrate metabolism. II. Influence of bile salts on the amount of glucose, pyruvate, citrate, and alpha.-ketoglutarate in the blood of normal and alloxan," 1 page (1958).
Database CA 1990:604829—Katagiri et al. "Tauromuricholic acid for treatment of bile acid secretory disorders," 2 pages (1990).
Database CA 1996:68395—Kitani, "The protective effect of hydrophilic bile acids on bile acid hepatotoxicity in the rat." 2 pages (1996).
Database CA 2002:481189—Paolini et al., "Anticholestatic bile acids as inducers of the cytochrome P450-dependent system," 2 pages (2002).
Database CA 2010:1477293—Shen et al. "99mTc-labeled bile acid derivative and its reference standard, and preparation method and medical application thereof as imaging agent," 4 pages (2010).
Database CA 2012:266494—Jani et al., "Treatment for nonalcoholic fatty liver disease," 2 pages (2012).
De Wit et al., "The role of the small intestine in the development of dietary fat-induced obesity and insulin resistance in C57BL/6J mice," *BMC Medical Genomics*, 1 (14), 1-16 (2008).
Donnelly et al., "Sources of fatty acids stored in liver and secreted via lipoproteins in patients with nonalcoholic fatty liver disease," *J. Clin. Invest.*, 115 (5), 1343-1351 (2005).
Donohoe et al., "The Microbiome and Butyrate Regulate Energy Metabolism and Autophagy in the Mammalian Colon," *Cell Metabolism*, 13, 517-526 (2011).
Dosa et al., "Synthesis and Evaluation of Water-Soluble Prodrugs of Ursodeoxycholic Acid (UDCA), an Anti-apoptotic Bile Acid," *ChemMedChem*, 8 (6), 1002-1011 (2013).

Ferraretto et al., "New Methodological Approach to Induce a Differentiation Phenotype in Caco-2 Cells Prior to Post-confluence Stage,"*Anticancer Res.*, 27, 3919-3925 (2007).
Fiorucci et al., "Development of FXR, PXR and CAR agonists and antagonists for treatment of liver disorders", *Curr. Top. Med. Chem.*, 12 (6), 605-624 (2012).
Flores et al., "Assessment of the human faecal microbiota: I. Measurement and reproducibility of selected enzymatic activities," *Eur. J. Clin. Invest.*, 42 (8), 848-854 (2012).
Forman et al., "Identification of a nuclear receptor that is activated by farnesol metabolites," *Cell*, 81 (5), 687-693, (1995).
Giardine et al., "Galaxy: a platform for interactive large-scale genome analysis," *Genome Res.*, 15, 1451-1455 (2005).
Goecks et al., "Galaxy: a comprehensive approach for supporting accessible, reproducible, and transparent computational research in the life sciences," *Genome Biol.*, 11 (8), R86, 1-13 (2010).
Goodwin et al., "A regulatory cascade of the nuclear receptors FXR, SHP-1, and LRH-1 represses bile acid biosynthesis," *Mol. Cell.*, 6, 517-528 (2000).
Górski, "Ceramide and Insulin Resistance: How Should the Issue Be Approached?," *Diabetes*, 61, 3081-3083 (2012).
Huang et al., "Corrigendum to Synthesis and antimicrobial evaluation of bile acid tridentate conjugates," *Steroids*, 75, 189 (2010).
Idle et al., "Metabolomics," *Cell Metabolism*, 6, 348-351 (2007).
Iida et al., "Potential bile acid metabolites. 14. Hyocholic and muricholic acid stereoisomers," *J. Lipid Res.*, 30 (8), 1267-1279 (1989).
Iida et al., "Potential bile acid metabolites: IV. Inversion of 7 alpha-hydroxyl ursodeoxycholic acid," *Lipids*, 16 (11), 863-865 (1981).
International Preliminary Report on Patentability, Application No. PCT/US2014/049460, dated Feb. 11, 2016.
International Search Report, Application No. PCT/US2014/049460, dated Jan. 26, 2015.
Jiang et al., "Diversity of bile salt hydrolase activities in different lactobacilli toward human bile salts." *Ann. Microbiol.*, 60, 81-88 (2010).
Karlsson et al., "The microbiota of the gut in preschool children with normal and excessive body weight," *Obesity*, 20 (11), 2257-2261 (2012).
Khandekar et al., "Molecular mechanisms of cancer development in obesity," *Nature*, 11, 886-895 (2011).
Kim et al., "Differential regulation of bile acid homeostasis by the farnesoid X receptor in liver and intestine," *J. Lipid Res.*, 48, 2664-2672 (2007).
Lack et al., "The ideal bile salt transport system: Effect of the charged state of the substrate on activity," *Biochim. Biophys. Acta*, 135 (5), 1065-1068 (1967).
Larsen et al., "Gut Microbiota in Human Adults with Type 2 Diabetes Differs from Non-Diabetic Adults," *PLoS One*, 5 (2), e9085, 1-10 (Feb. 2010).
Li et al., "Homocysteine Upregulates Resistin Production From Adipocytes In Vivo and In Vitro," *Diabetes*, 57, 817-827 (Apr. 2008).
Li et al., "Stable Isotope- and Mass Spectrometry-based Metabolomics as Tools in Drug Metabolism: A Study Expanding Tempol Pharmacology," *J. Proteome Res.*, 12 (3), 1369-1376 (2013).
Li et al., "Microbiome remodelling leads to inhibition of intestinal farnesoid X receptor signalling and decreased obesity," *Nat. Commun.*, 4:2384, 1-10 (2013).
Lozupone et al., "UniFrac: a new phylogenetic method for comparing microbial communities," *App. Environ. Microbiol.*, 71 (2), 8228-8235 (2005).
Lyznicki et al., "Obesity: assessment and management in primary care," *Am. Fam. Phys.*, 63, 2185-2196 (2001).
Ma et al., "Farnesoid X receptor is essential for normal glucose homeostasis," *J. Clin. Invest.*, 116 (4), 1102-1109 (2006).
Mangelsdorf et al., "The RXR heterodimers and orphan receptors" *Cell*, 83 (6), 841-850 (1995).
Matsubara et al., "Metabolomics Identifies an Inflammatory Cascade Involved in Dioxin- and Diet-Induced Steatohepatitis," *Cell Metabolism*, 16, 634-644 (2012).

(56) References Cited

OTHER PUBLICATIONS

Matsubara et al., "Lithocholic Acid Disrupts Phospholipid and Sphingolipid Homeostasis Leading to Cholestasis in Mice," *Hepatology*, 53 (4), 1282-1293 (2011).
Matsubara et al., "FXR signaling in the enterohepatic system," *Mol. Cell. Endocrinol.*, 368 (1-2), 17-29 (2013) Author Manuscript.
Mitchell et al., "The Antioxidant Tempol Reduces Carcinogenesis and Enhances Survival in Mice When Administered after Nonlethal Total Body Radiation," *Cancer Res.*, 72 (18), 4846-4855 (2012).
Mitchell et al., "A Low Molecular Weight Antioxidant Decreases Weight and Lowers Tumor Incidence," *Free Rad. Bio. Med.*, 34 (1), 93-102 (2003).
Musso et al., "Interactions Between Gut Microbiota and Host Metabolism Predisposing to Obesity and Diabetes," *Ann. Rev. Med.*, 62, 361-360 (2011).
Musso et al., "Obesity, Diabetes, and Gut Microbiota," *Diabetes Care*, 33 (10) 2277-2284 (2010).
National Institutes of Health, "Clinical Guidelines on the Identification, Evaluation, and Treatment of Overweight and Obesity in Adults—The Evidence Report. National Institutes of Health" *Obes. Res.*, 6 (supp. 2) 51S-179S (1998).
Phillips et al., "Oxidant stress and constrictor reactivity impair cerebral artery dilation in obese Zucker rats," *Am. J. Physiol. Regul. Integr. Comp. Physiol.*, 288, R522-R530 (2005).
Prawitt et al., "Farnesoid X Receptor Deficiency Improves Glucose Homeostasis in Mouse Models of Obesity," *Diabetes*, 60, 1861-1871 (2011).
PubMed NCBI Search Results "'farnesoid x receptor' Inhibit" 7 pages, (Aug. 28, 2013).
Ravussin et al., "Estimating Energy Expenditure in mice using an Energy Balance Technique" *Int. J. Obesity*, 37 (3), 399-403 (2013) Author Manuscript.
Ridlon et al., "Bile salt biotransformations by human intestinal bacteria," *J. Lipid Res.*, 47, 241-259 (2006).
Rizzo et al., "Functional Characterization of the Semisynthetic Bile Acid Derivative INT-767, a Dual Farnesoid X Receptor and TGR5 Agonist," *Mol. Pharmacol.*, 78 (4), 617-630 (2010).
Roda et al., "Synthesis and Physiochemical, Biological, and Pharmacological Properties of New Bile Acids Amidated with Cyclic Amino Acids +" *J. Med. Chem.*, 39 (11), 2270-2276 (1996).
Rozen et al., "Selective Flourination of Bile Acids Using Elemental Flourine" *Tetra. Letters*, 25 (18), 1947-1948 (1984).
Samad et al., "A Potential Mechanism for Cardiovascular and Metabolic Risk," *Diabetes*, 55, 2579-2587 (2006).
Sato et al., "Novel Potent and Selective Bile Acid Derivatives as TGR5 Agonists: biological screening, structure-activity relationships, and molecular modeling studies," *J. Med. Chem.*, 51 (6), 1831-1841 (2008).
Sayin et al., "Gut Microbiota regulates acid metabolism by reducing the levels of Tauro-beta-muricholic Acid, a naturally occurring FXR Antagonist," *Cell Metab.*, 17 (2), 225-235 (2013).
Schloss et al., "Introducing mothur: Open-Source, Platform-Independent, Community-Supported Software for Describing and Comparing Microbial Communities," Appl. Environ. Microbiol., 75 (23), 7537-7541 (2009).
Scifinder Author Search Results, 35 pages (Aug. 28, 2013).
Shukla et al., "Microbial Transformation of Quinoline by a *Pseudomonas* sp.," *Appl. Environ. Microbiol.*, 51 (6), 1332-1342 (1986).
Sinal et al., "Targeted Disruption of the Nuclear Receptor FXR/BAR Impairs Bile Acid and Lipid Homeostasis," *Cell*, 102 (6), 731-744 (2000).
Soule et al., "The chemistry and biology of nitroxide compounds," *Free Radic. Biol. Med.*, 42 (11) 1632-1650 (2007).
Swann et al., "Systemic gut microbial modulation of bile acid metabolism in host tissue compartments," *Proc. Natl. Acad. Sci. USA*, 108 (Supp. 1), 4523-4530 (2011).
Tserng et al., "Synthesis of sulfate esters of lithocholic acid, glycolithocholic acid, and taurolithocholic acid with sulfur trioxide-triethylamine" *J. Lipid Res.*, 18, 491-495 (1977).

Tuohy et al., "Studying the Human Gut Microbiota in the Trans-Omics Era—Focus on Metagenomics and Metabonomics," *Curr. Pharma. Des.*, 15, 1415-1427 (2009).
Turnbaugh et al., "An Invitation to the Marriage of Metagenomics and Metabolomics," *Cell*, 134, 708-713 (2008).
Turnbaugh et al., "An obesity-associated gut microbiome with increased capacity for energy harvest," *Nature*, 444, 1027-1031 (2006).
Walker et al., "A less stressful alternative to oral gavage for pharmacological and toxicological studies in mice," Toxicol. Appl. Pharmacol., 260 (1), 65-69 (2012) Author Manuscript.
Wang et al., "Naïve Bayesian Classifier for Rapid Assignment of rRNA Sequences into the New Bacterial Taxonomy," *Appl. Environ. Microbiol.*, 73 (16), 5261-5267 (Aug. 2007).
Wang et al., "Endogenous bile acids are ligands for the nuclear receptor FXR/BAR," Mol. Cell, 3 (5), 543-553 (1999).
Watanabe et al., "Lowering Bile Acid Pool Size with a Synthetic Farnesoid X Receptor (FXR) Agonist Induces Obesity and Diabetes through Reduced Energy Expenditure," *J. Biol. Chem.*, 286 (30), 26913-26920 (2011).
Weiß et al., "Non-Alcoholic Fatty Liver Disease" *Dtsch. Arztebl. Int.*, 111, 447-452 (2014).
Wikoff et al., "Metabolomics analysis reveals large effects of gut microflora on mammalian blood metabolites," *PNAS*, 106 (10), 3698-3703 (2009).
Written Opinion of the International Searching Authority, Application No. PCT/US2014/049460, dated Jan. 26, 2015.
Yu et al., "Identification of Trisubstituted-pyrazol Carboxamide Analogs as Novel and Potent Antagonists of Farnesoid X Receptor," *Bioorg. Med. Chem.*, 22 (11), 2919-2938 (2014) Author Manuscript.
Yu et al., "Effect of guggulsterone and cembranoids of Commiphora mukul on pancreatic phospholipase A(2): role in hypocholesterolemia," *J. Nat. Prod.*, 72 (1), 24-28 (2009).
Zhang et al., "Abcb11 Deficiency Induces Cholestasis Coupled to Impaired β-Fatty Acid Oxidation in Mice," *J. Biol. Chem.*, 287 (29), 24784-24794 (2012).
Zhang et al., "Dysfunction of organic anion transporting polypeptide 1a1 alters intestinal bacteria and bile acid metabolism in mice," *PLos One*, 7 (4):e34522 (2012).
Zhang et al., "Activation of the nuclear receptor FXR improves hyperglycemia and hyperlipidemia in diabetic mice," *PNAS*, 103 (4), 1006-1011 (2006).
Abu-Hayyeh et al., "Intrahepatic Cholestasis of Pregnancy Levels of Sulfated Progesterone Metabolites Inhibit Farnesoid X Receptor Resulting in a Cholestatic Phenotype," *Hepatology*, 57, 716-726 (Feb. 2013).
García-Cañaveras et al., "Targeted Profiling of Circulating and Hepatic Bile Acids in Human, Mouse, and Rat Using a UPLC-MRM-MS-validated Method," *J. Lipid Research* 53, 2231-2241 (2012).
Griffin et al., "Combination Lopinavir and Ritonavir Alter Exogenous and Endogenous Bile Acid Disposition in Sandwich-Cultured Rat Hepatocytes," *Drug Metabolism and Disposition*, 41, 188-196 (Jan. 2013).
Haeusler et al., "Impaired Generation of 12-Hydroxylated Bile Acids Links Hepatic Insulin Signaling With Dyslipidemia," *Cell Metabolism*, 15(1) 65-74 (2012).
Ito et al., "Disruption of Stard10 Gene Alters the PPARα-mediated Bile Acid Homeostasis," Biochim Biophys Acta, 1831(2):459-68 (Feb. 2013).
Kitani, "The Protective Effect of Hydrophilic Bile Acids on Bile Acid Hepatotoxicity in the Rat," *Italian Journal of Gastroenterology* 27(7): 366-71 (Sep. 1995).
Kobayashi, "Influence of Bile Salts on the Fat Metabolism (I) Lipotropic Action of Bile Salts," *Hiroshima Journal of Medical Sciences* 27:366-371 (1955).
Li et al., "Metabolomics Reveals an Essential Role for Peroxisome Proliferator-Activated Receptor α in a Bile Acid Homeostasis," *Journal of Lipid Research* 53: 1625-1635 (2012).
Marion et al., "Endogenous Bile Acid Disposition in Rat and Human Sandwich-Cultured Hepatocytes," *Toxicol App Pharmacol*, 261(1): 1-9 (May 15, 2012).

(56) References Cited

OTHER PUBLICATIONS

Seyer et al., "Hepatic Glucose Sensing is Required to Preserve β Cell Glucose Competence," *The Journal of Clinical Investigation* 123(4): 1662-1676 (Apr. 2013).

Taguchi et al., "Simultaneous and Rapid Analysis of Bile Acids Including Conjugates by Supercritical Fluid Chromatography Coupled to Tandem Mass Spectrometry," *Journal of Chromatography* 1299:103-109 (May 2013).

Zhang et al., "Organic Anion Transporting Polypeptide 1a1 Null Mice Are Sensitive to Cholestatic Liver Injury," *Toxicological Sciences* 172(2): 451-462 (2012).

* cited by examiner

**P<0.01 compared to *Fxr^{fl/fl}* mice

**P<0.01 compared to control, ##P<0.01 compared to CDCA (100 μM) treatment

**P<0.01 compared to control, #P<0.05, ##P<0.01 compared to Gw4064 treatment 5/14

\*\*$P<0.01$ compared to control, #$P<0.05$, ##$P<0.01$ compared to Gw4064 treatment

**P<0.01 compared to control, #P<0.05, ##P<0.01 compared to Gw4064 treatment

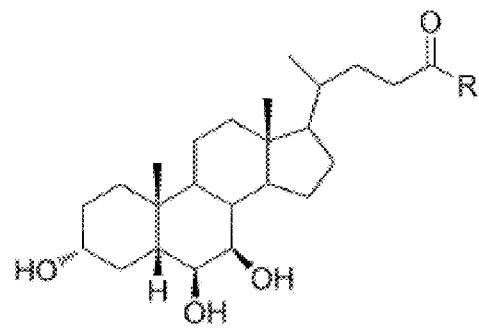
β-Muricholic acid: R = OH
Tauro-β-Muricholic acid (TβMCA): R = NHCH$_2$CH$_2$SO$_3$H
Glycine-β-Muricholic acid (Gly-MCA): R = NHCH$_2$COOH
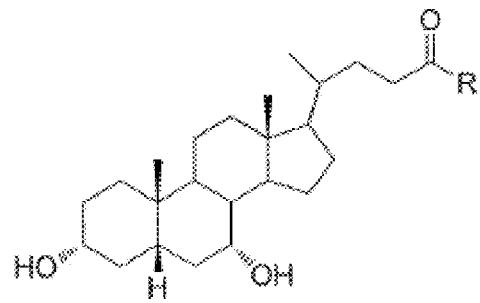
Chenodeoxycholic acid: R = OH
Taurocholic acid (TCA): R = NHCH$_2$CH$_2$SO$_3$H
Glycine-chenodeoxycholic acid: R = NHCH$_2$COOH
FIG. 10

** P<0.01 compared to to vehicle-treated mice of the same genotype

**P<0.01 compared to $Fxr^{fl/fl}$ mice

*P<0.05 compared to $Fxr^{fl/fl}$ mice

*P<0.05, **P<0.01 compared to Fxr$^{fl/fl}$ mice

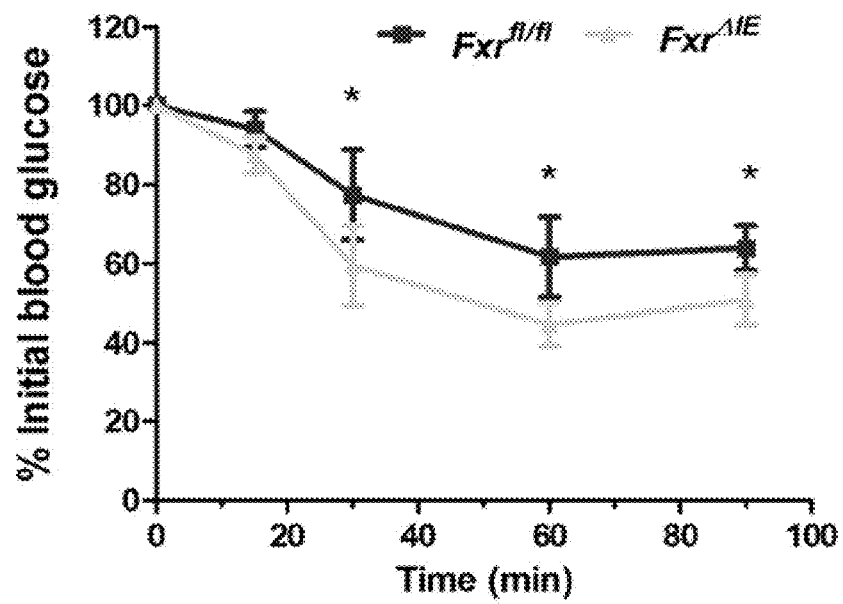
*$P<0.05$, **$P<0.01$ compared to $Fxr^{fl/fl}$ mice
FIG. 14
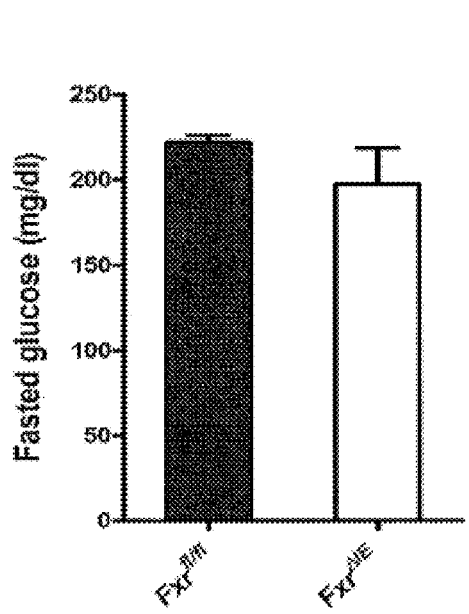
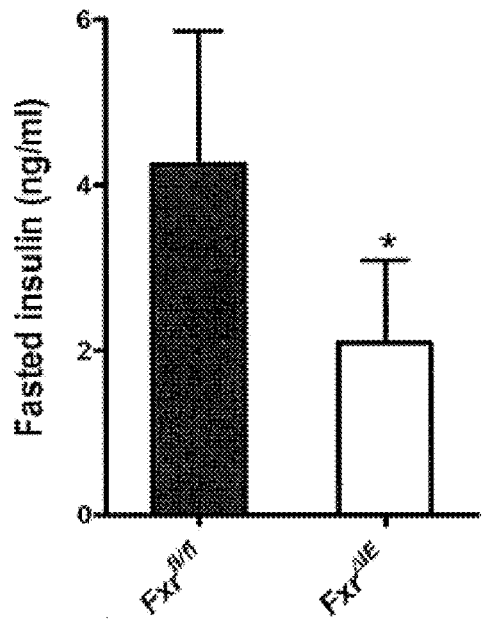
*$P<0.05$ compared to $Fxr^{fl/fl}$ mice
FIG. 15A　　　　　　　　　　FIG. 15B

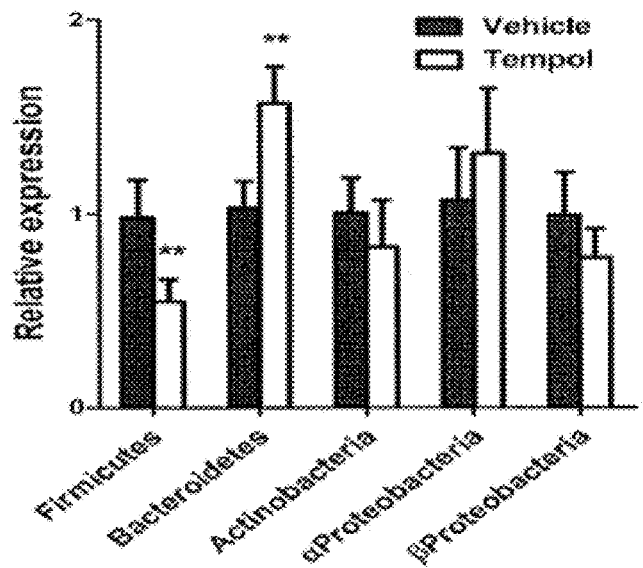
**P<0.01 compared to vehicle treated mice
FIG. 16B
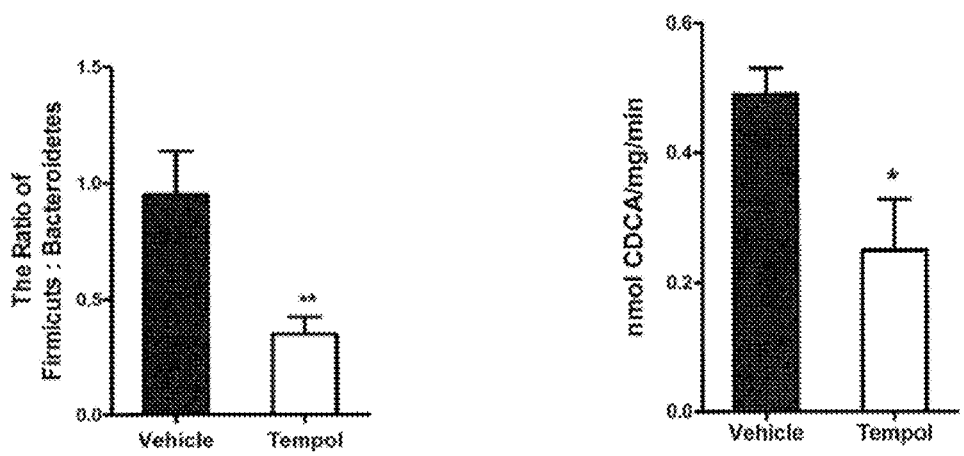
**P<0.01 compared to vehicle treated mice   *P<0.05 compared to vehicle treated mice
FIG. 17A                                    FIG. 17B

**P<0.01 compared to vehicle

**P<0.01 compared to vehicle

**p<0.01

**P<0.01

**P<0.01

**$p<0.01$

**P<0.01 compared to vehicle

**P<0.01 compared to vehicle

**P<0.01 compared to vehicle; *P<0.05 compared to vehicle

**P<0.01 compared to vehicle

P<0.01 compared to vehicle; P<0.01 compared to TCA

**P<0.01

**P<0.01

*$P<0.05$ compared to $Fxr^{fl/fl}$

*$P<0.05$ compared to $Fxr^{fl/fl}$

**$P<0.01$ compared to vehicle; *$P<0.05$ compared to vehicle

**P<0.01 compared to vehicle

**P<0.01 compared to vehicle; *P<0.05 compared to vehicle

**P<0.01 compared to $Fxr^{fl/fl}$; *P<0.05 compared to $Fxr^{fl/fl}$

**P<0.01 compared to vehicle

**$P<0.01$ compared to vehicle

**P<0.01 compared to vehicle

**P<0.01 compared to vehicle

**P<0.01 compared to vehicle

**P<0.01 compared to vehicle

**P<0.01 compared to vehicle

*P<0.05 compared to $Fxr^{fl/fl}$ + vehicle

**P<0.01 compared negative control

**P<0.01 compared to vehicle

**P<0.01 compared to control; ##P<0.01 compared to control CDCA

**P<0.01 compared to control; ##P<0.01 compared to control, 2 μM GW4064

**P<0.01 compared to control; ##P<0.01 compared to control, 2 μM GW4064

*P<0.05 compared to control; #P<0.05 compared to control, 2 μM or 5 μM GW4064; ##P<0.01 compared to control, 2 μM or 5 μM GW4064

**P<0.01 comparing Gly-MCA to vehicle

**P<0.01 comparing Gly-MCA to vehicle

**P<0.01 compared to vehicle

**P<0.01 comparing Gly-MCA to vehicle

**P<0.01 compared to vehicle

**P<0.01 comparing Gly-MCA to vehicle

**P<0.01 compared to vehicle

*P<0.05 comparing Gly-MCA to vehicle

**P<0.01 compared to vehicle

**P<0.01 compared to vehicle

**P<0.01 compared to vehicle

**P<0.01 compared to vehicle

**P<0.01 compared to vehicle

**P<0.01 compared to vehicle; *P<0.05 compared to vehicle

**P<0.01 compared to vehicle; *P<0.05 compared to vehicle

**P<0.01 compared to vehicle

**$P<0.01$ compared to vehicle; *$P<0.05$ compared to vehicle

**P<0.01 compared to vehicle; *P<0.05 compared to vehicle

**P<0.01 compared to vehicle

*\*\*P<0.01 compared to vehicle*

*\*P<0.05 compared to vehicle*

**P<0.01 compared to vehicle

*P<0.05 compared to vehicle

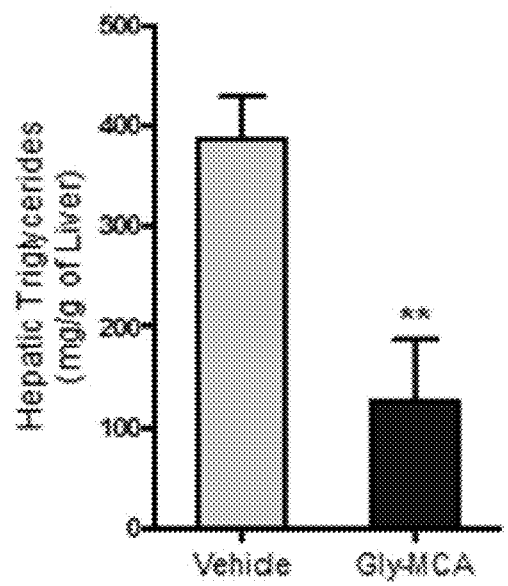
**P<0.01 compared to vehicle
FIG. 54D
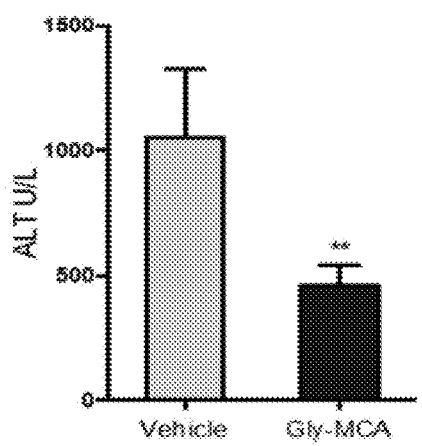 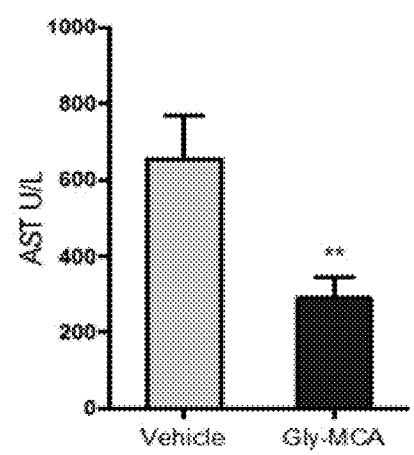
**P<0.01 compared to vehicle
FIG. 55A
**P<0.01 compared to vehicle
FIG. 55B

*P<0.05 compared to vehicle

**P<0.01 compared to vehicle; *P<0.05 compared to vehicle

**P<0.01 compared to vehicle; *P<0.05 compared to vehicle

**P<0.01 compared to vehicle; *P<0.05 compared to vehicle

*$P<0.05$ compared to vehicle

**$P<0.01$ compared to vehicle

**P<0.01 compared to vehicle

*P<0.05 compared to vehicle

*P<0.05 compared to vehicle

**P<0.01 compared to vehicle; *P<0.05 compared to vehicle

INHIBITORS OF THE FARNESOID X RECEPTOR AND USES IN MEDICINE

CROSS-REFERENCE TO RELATED APPLICATIONS

This patent application is a continuation of copending U.S. patent application Ser. No. 14/909,263, filed Feb. 1, 2016, which is a 371 of International Patent Application No. PCT/US2014/049460, filed Aug. 1, 2014, which claims the benefit of U.S. Provisional Patent Applications Nos. 61/861,109, filed Aug. 1, 2013, and 62/004,436, filed May 29, 2014, which are incorporated by reference for all purposes.

This invention was made with government support under Grant No. ES022186 awarded by the National Institutes of Health and under Hatch Act Project Nos. PEN04451 and PEN04607, awarded by the United States Department of Agriculture. The Government has certain rights in the invention.

BACKGROUND OF THE INVENTION

Obesity has reached epidemic proportions worldwide and is associated with chronic diseases such as type 2 diabetes mellitus, cardiovascular diseases, hepatosteatosis, and cancer. Obesity develops as a result of energy intake that exceeds energy expenditure, leading to a net storage of excess calories in the form of fat in adipose tissue. Obesity is metabolically linked with type 2 diabetes (insulin resistance) and hepatosteatosis, the latter of which can lead to steatohepatitis, hepatocarcinogenesis and liver failure. Thus, a pharmaceutical approach that suppresses appetite, blocks dietary fat absorption, induces fat mobilization, or increases metabolism would be ideal in the treatment of obesity and related metabolic disorders.

Farnesoid X Receptor (FXR) is an orphan nuclear receptor initially identified from a rat liver cDNA library (Forman, et al., *Cell* 81:687-693, 1995) that is most closely related to the insect ecdysone receptor. FXR is a member of the nuclear receptor superfamily of transcription factors that includes receptors for the steroid, retinoid, and thyroid hormones (Mangelsdorf, et al., *Cell* 83:841-850, 1995). Northern blotting and in situ hybridization analysis showed that FXR is most abundantly expressed in the liver, intestine, kidney, and adrenal (B. M. Forman, et al., *Cell* 81:687-693.1995; Seol, et al., *Mol. Endocrinol.* 9:72-85, 1995). FXR is a ligand-activated nuclear receptor that binds to DNA as a heterodimer with the retinoic acid receptor α (RXRα) that is activated by the vitamin A derivative 9-cis retinoic acid. The FXR/RXRα heterodimer preferentially binds to response elements composed of two nuclear receptor half sites of the consensus AG(G/T)TCA organized as an inverted repeat and separated by a single nucleotide (IR-1 motif) (Forman, et al., *Cell* 81:687-693, 1995). An early report showed that rat FXR is activated by micromolar concentrations of farnesoids such as farnesol and juvenile hormone thus accounting for the original name (Forman, et al., *Cell* 81:687-693, 1995). However, these compounds were weak ligands and also failed to activate the corresponding mouse and human FXR, leaving the nature of the endogenous FXR ligand in doubt. However, several naturally-occurring bile acids were found to bind to and activate FXR at physiological concentrations (Makishima, et al., *Science* 284:1362-1365, 1999; Parks, et al., *Science* 284:1365-1368, 1999; Wang et al., *Mol. Cell* 3:543-553, 1999; PCT WO 00/37077, published Jun. 29, 2000). The bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. About 95% of bile acids are subsequently reabsorbed in the ileum and returned to the liver via the enterohepatic circulatory system. The conversion of cholesterol to bile acids in the liver is under feedback regulation, and bile acids down-regulate transcription of cytochrome P450 7A1 (CYP7A1), which encodes the enzyme that catalyzes the rate-limiting step in bile acid biosynthesis. FXR is involved in the repression of CYP7A1 expression by bile acids through an indirect mechanism involving the FXR target gene small heterodimer partner (SHP) and liver receptor homolog 1 (Goodwin et al., *Mol. Cell* 6:517-528, 2000; reviewed in Matsubara et al., *Mol. Cell. Endocrinol.* 368:17-29, 2013). In the ileum, in an FXR dependent manner, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters. Thus, FXR is involved in both the stimulation (IBABP) and the repression (CYP7A1) of target genes involved in bile acid and cholesterol homeostasis. FXR also induces expression of the bile salt export pump (BSEP, ABC11) that transports unconjugated and conjugated bile acids/salts from hepatocyte into the bile (reviewed in Matsubara et al., *Mol. Cell. Endocrinol.* 368:17-29, 2013).

Tempol (4-hydroxy-2,2,6,6,-tetramethylpiperidine-1-oxyl), an antioxidant and a radiation protector, was reported to prevent obesity in mice (Mitchell et al., *Free Radic. Biol Med.* 34: 93-102, 2003). A recent mass spectrometry-based investigation revealed that tempol can affect fatty acid metabolism and the altered levels of suspected gut microbe-generated metabolites provided initial clues that tempol may alter the microbiome (Li et al., *J. Proteome Res.,* 12:1369-1376, 2013). Previous studies demonstrated that the alteration of the gut microbiome can affect the level of bile acids in liver, heart, and kidney (Swann et al., *Proc. Natl. Acad. Sci. USA* 108:4523-4530, 2011). High fat diets can induce changes in the expression of genes in the small intestine that are controlled by nuclear receptors including FXR (de Wit et al., *BMC Med. Genomics* 1:14, 2008). Thus, there may be relationship between altered bile acids in the intestine and FXR signaling that can alter high fat diet-induced obesity. While there are known natural and synthetic FXR agonist, no therapeutic agents have been disclosed which antagonize FXR. Recent studies revealed that the secondary bile acid tauro-β-muricholic acid (TβMCA) can antagonize bile acid signaling in the intestine (Sayin et al., *Cell Metab.* 225-235, 2013; Li et al., *Nat. Commun.* 4:2384, 2013). Trisubstituted-pyrazol carboxamide analogs have been synthesized that are FXR antagonist, but their effect on metabolism and physiology were not investigated (Yu et al., *Bioorg. Med. Chem.* 2919-2938, 2014).

Non-alcoholic fatty liver disease (NAFLD) is characterized by massive ectopic triglyceride (TG) accumulation in the liver in the absence of other liver disease or significant alcohol consumption (Weiß et al., *Ditsch. Arzteb.l Int.* 2014; 0.447-452, 2014). NAFLD is the most common liver disorder affecting 20-30% of the adult population and more than 80% of obese people in the world. NAFLD can develop into nonalcoholic steatohepatitis (NASH), fibrosis, cirrhosis and even hepatocellular carcinoma (Browning et al., *J. Clin Invest.* 114:147-152, 2004). As a component of metabolic syndrome, NAFLD is tightly associated with obesity, insulin resistance/type 2 diabetes, and coronary heart disease and atherosclerosis (Bhatia et al., *Eur. Heart* 33:1190-1200, 2012). To date, the underlying molecular mechanism of NAFLD development remains largely unknown and the identification of novel targets for NAFLD therapy is of high priority.

The foregoing shows that there is an unmet need for antagonists of the FXR receptor and a method of treating obese patients to induce weight loss, insulin resistance, and NAFLD.

BRIEF SUMMARY OF THE INVENTION

The present invention provides inhibitors of the nuclear receptor farnesoid X receptor for treating or preventing obesity in mammals, particularly humans. Compounds embodying aspects of the invention inhibit the farnesoid X receptor and affect high fat diet-induced obesity through signal transduction mediated by the farnesoid X receptor. In accordance with the invention, the present invention provides compositions comprising these compounds and methods of using these compounds as therapeutic agents in the treatment or prevention of obesity.

The invention also provides a pharmaceutical composition comprising a compound or salt embodying the principles of the invention and a pharmaceutically acceptable carrier.

The invention further provides a method of inhibiting a farnesoid X receptor in a mammal, comprising administering to a mammal in need thereof a compound embodying the principles of the invention or a pharmaceutically acceptable salt thereof.

The invention additionally provides a method for treating or preventing obesity in a mammal, comprising administering to a mammal in need thereof a compound embodying the principles of the invention or a pharmaceutically acceptable salt thereof.

The invention also provides a method for treating or preventing obesity, insulin resistance and NAFLD in a mammal in need thereof, comprising administering to the mammal a compound embodying the principles of the invention or a pharmaceutically acceptable salt thereof. Desirably, the compounds inhibit the farnesoid X receptor in the intestine and affects obesity, insulin resistance and NAFLD through signal transduction mediated only by the intestinal farnesoid X receptor and not by the liver farnesoid X receptor. Preferably, the compounds have minimal systemic bioavailability so that the compounds do not inhibit the liver farnesoid X receptor which minimizes any systemic toxicity.

The invention further provides methods of synthesizing the compound embodiments of the invention.

BRIEF DESCRIPTION OF THE SEVERAL VIEWS OF THE DRAWING(S)

FIG. 10 depicts the structures of β-muricholic acid, tauro-β-muricholic acid (TβMCA), glycine-β-muricholic acid, chenodeoxycholic acid, taurochenodeoxycholic acid (TCA), and glycine-chenodeoxycholic acid.

Figure 12A:
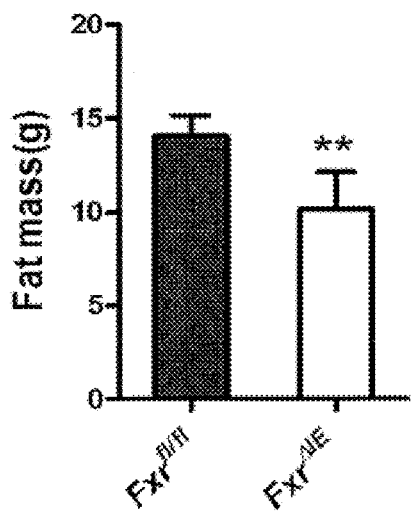
Figure 12B:
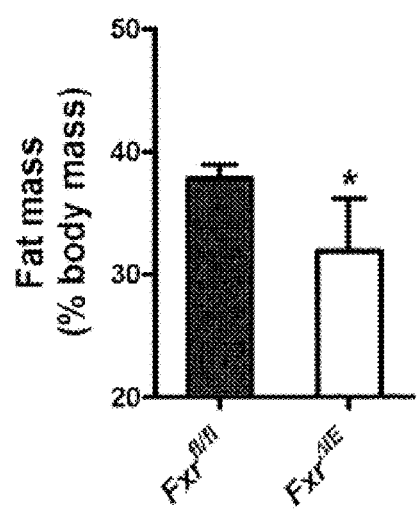

FIGS. 12A and B illustrate the fat mass in grams and as a percentage of body mass for $Fxr^{fl/fl}$ and $Fxr^{\Delta IE}$ mice after 14 weeks of a high fat diet.

Figure 13:
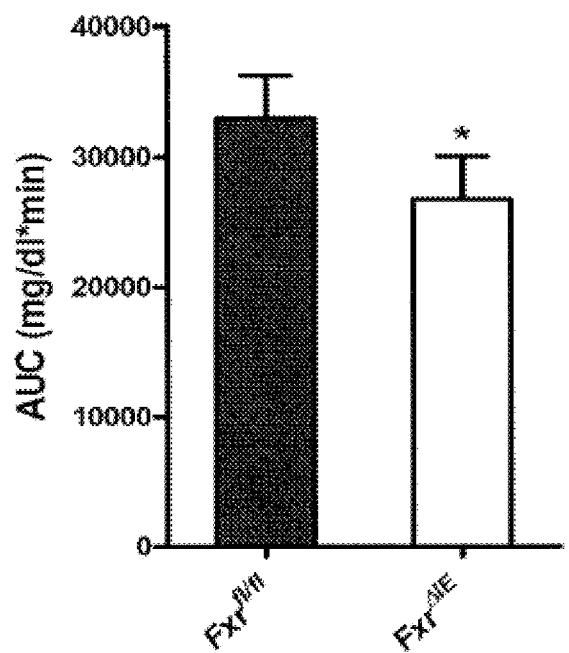

FIG. 13 illustrates the results of a glucose tolerance test (GTT) for $Fxr^{fl/fl}$ and $Fxr^{\Delta IE}$ mice after 7 weeks of a high fat diet.

FIG. 14 illustrates the results of an insulin tolerance test (ITT) for $Fxr^{fl/fl}$ and $Fxr^{\Delta IE}$ mice after 13 weeks of a high fat diet.

Figure 15C:
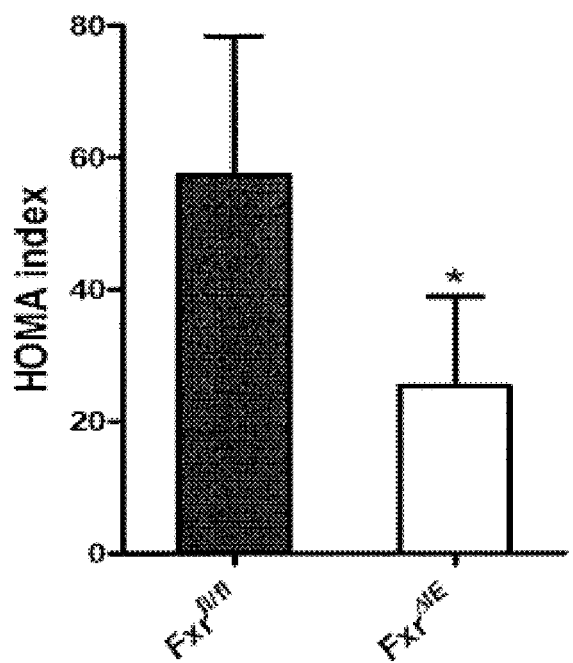

FIGS. 15A-C illustrate the fasted glucose, fasted serum insulin, and HOMA index for $Fxr^{fl/fl}$ and $Fxr^{\Delta IE}$ mice after 15 weeks of a high fat diet.

Figure 16A:
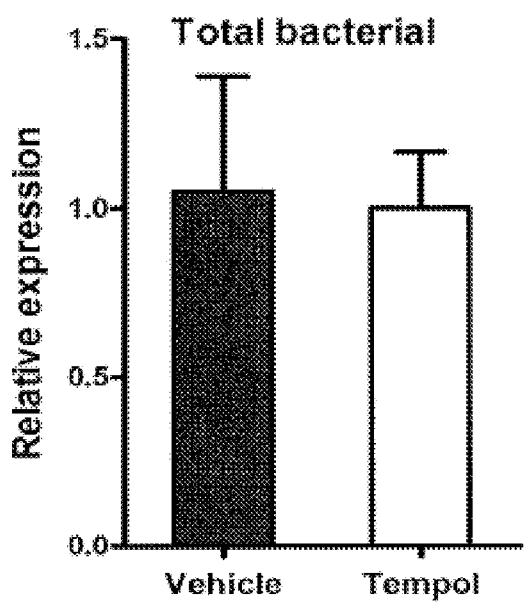
Figures 18A, 18B, 18C, 18D:
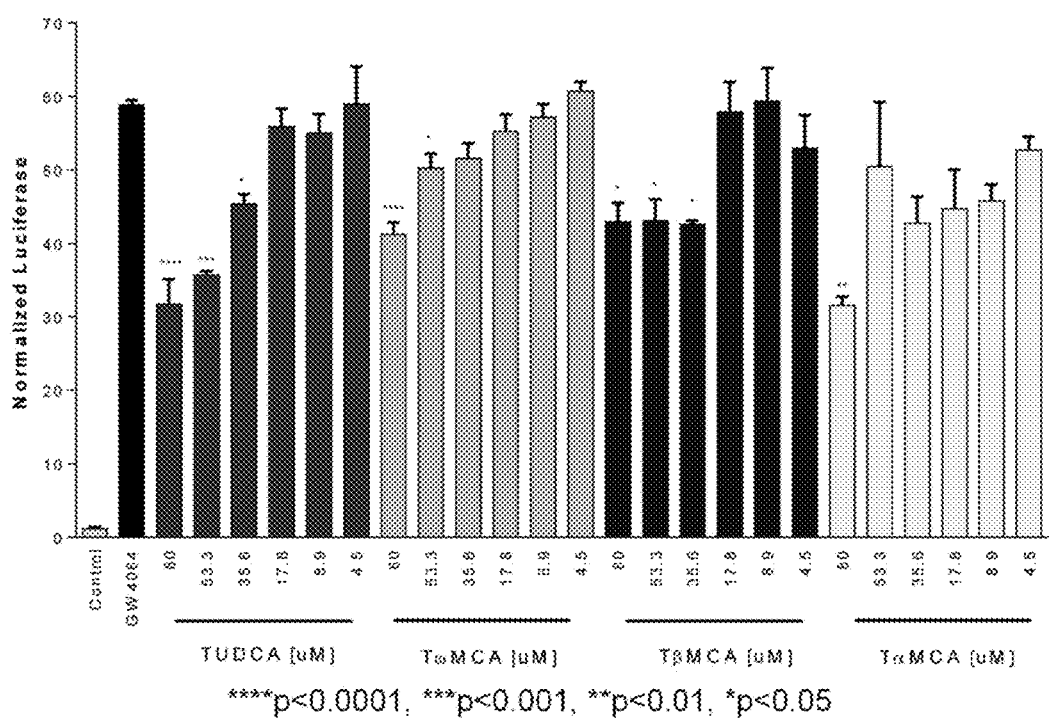

FIGS. 16A and B depict the shift from Firmicutes to Bacteroidetes in mice being fed a normal chow diet upon treatment with tempol.

FIGS. 17A and B depict a comparison of the ratio of Firmicutes to Bacteroidetes and the bile salt hydrolase enzymatic activity in the feces of mice on a normal chow diet and treated with vehicle or tempol.

FIGS. 18A-D illustrate a human FXR competition assay using the synthetic agonist GW4064 and varied doses of TUDCA, TωMCA, TβMCA, TαMCA. Results were normalized to *Renilla* expression.

Figure 19A:
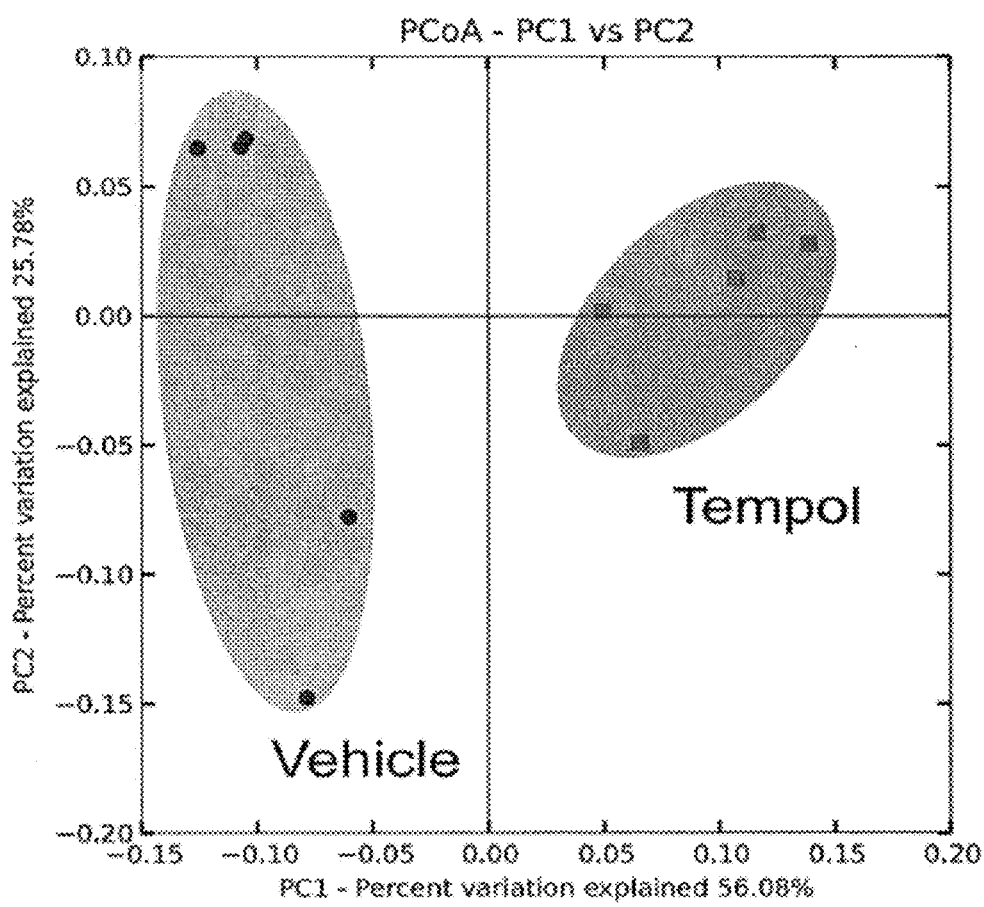
Figure 19B:
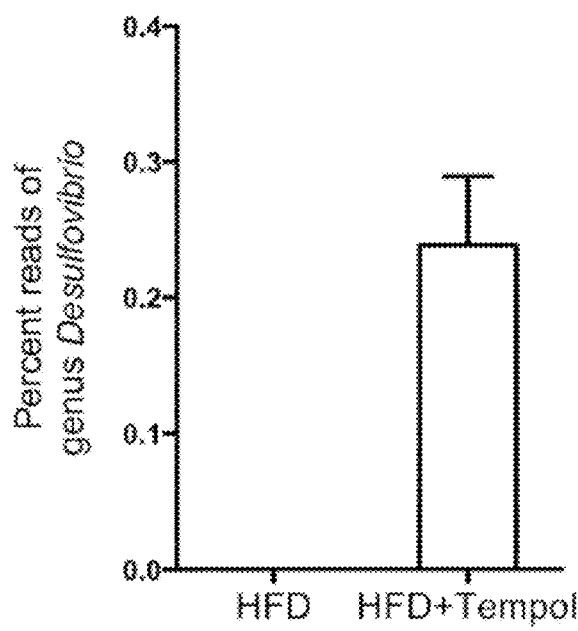
Figure 19C:
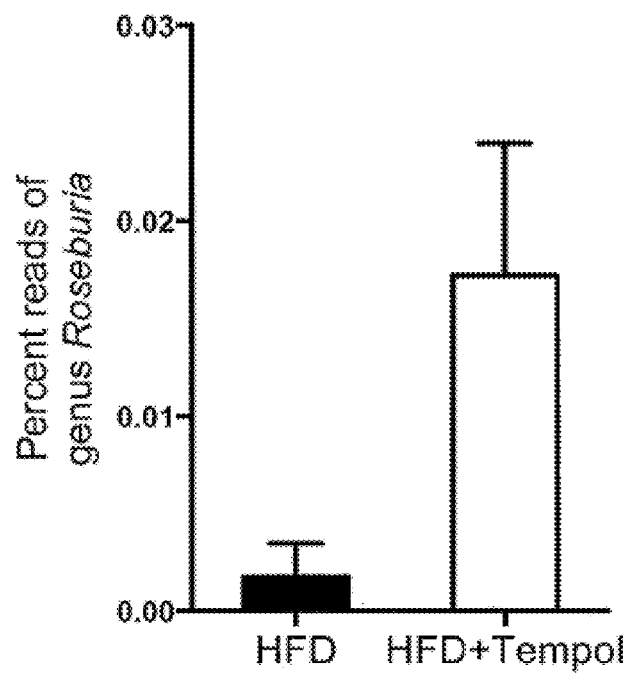
Figure 19D:
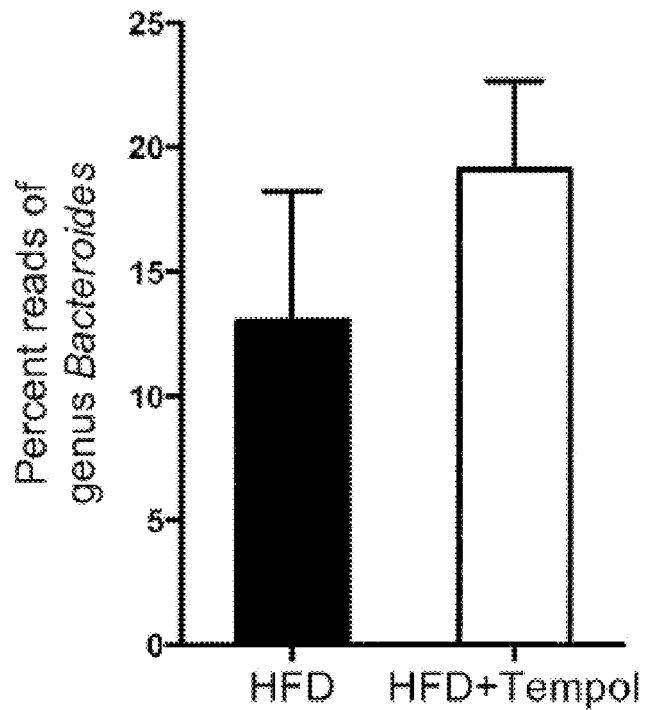
Figure 19E:
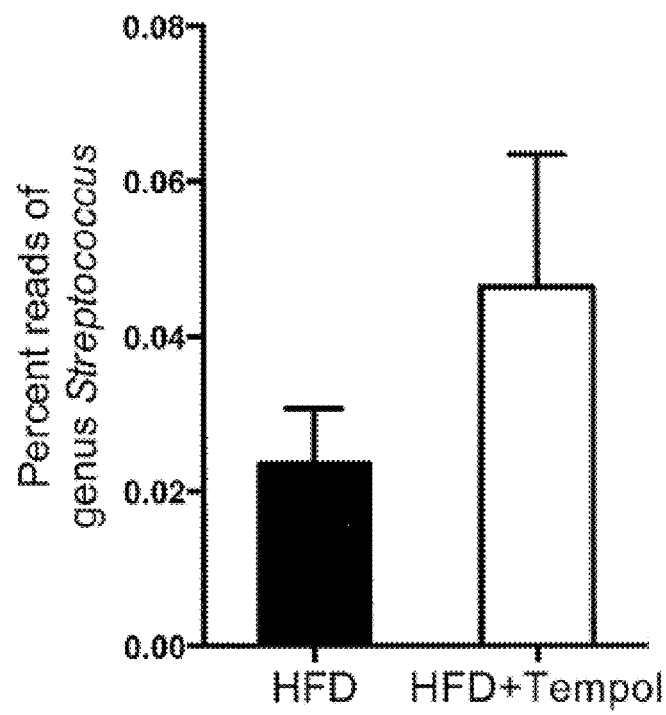
Figure 19F:
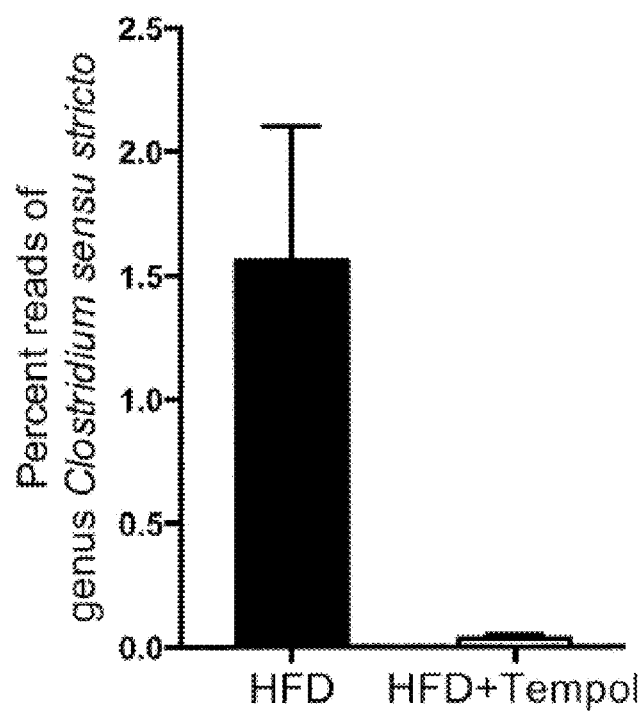
Figure 19G:
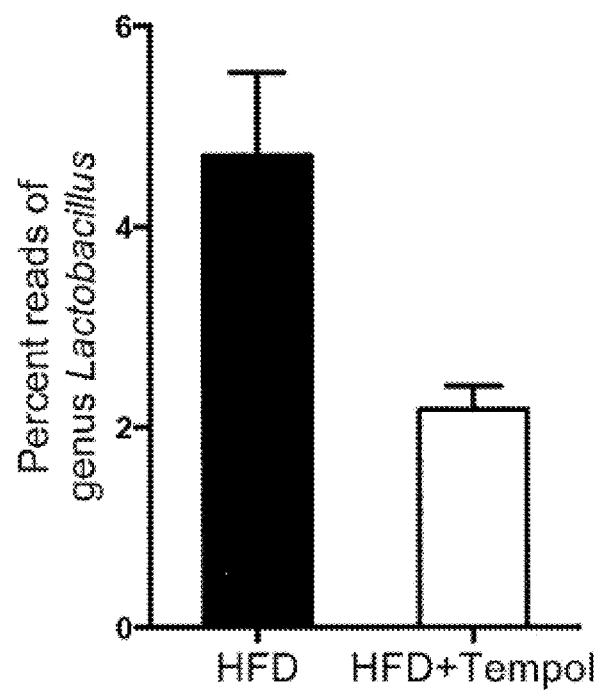

FIG. 19A shows a principal coordinates analysis plot of weighted UniFrac distances. Circles represent cecal communities in vehicle-treated mice and squares represent cecal communities in tempol-treated mice. Both groups were fed a high-fat diet for 10 weeks.

FIG. 19B-G shows 16S rRNA gene sequencing analysis of genus levels of cecum content. Data are presented as mean±SD.

Figure 20A:
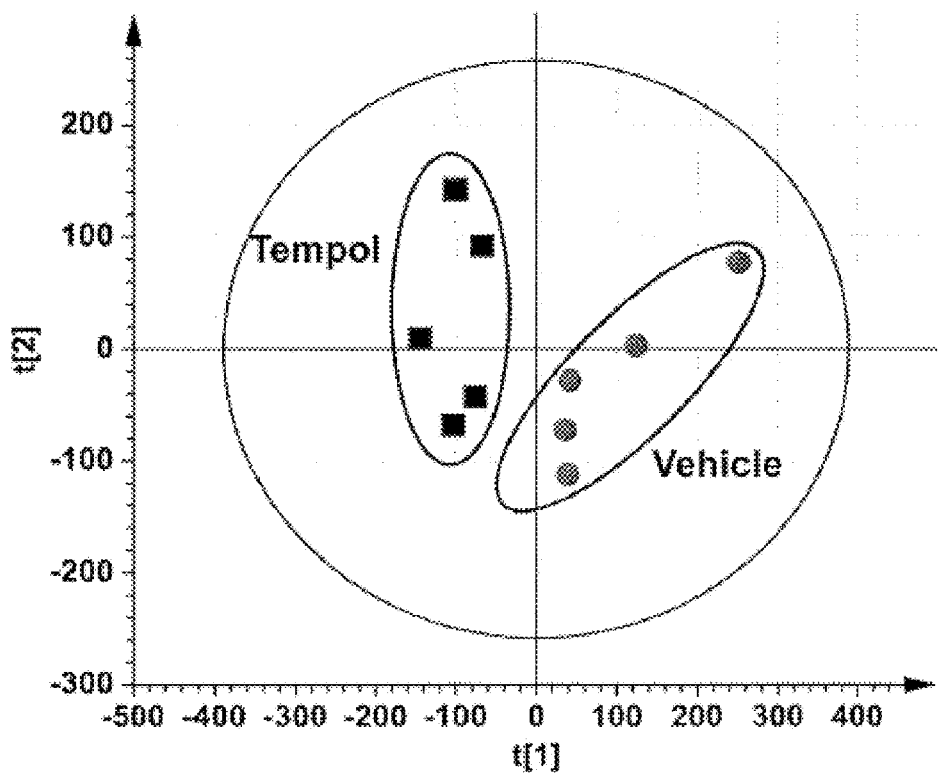

FIG. 20A shows a scores scatter plot of a principal components analysis (PCA) model of urine ions in vehicle- and tempol-treated mice fed a high-fat diet for 14 weeks.

Figure 20B:
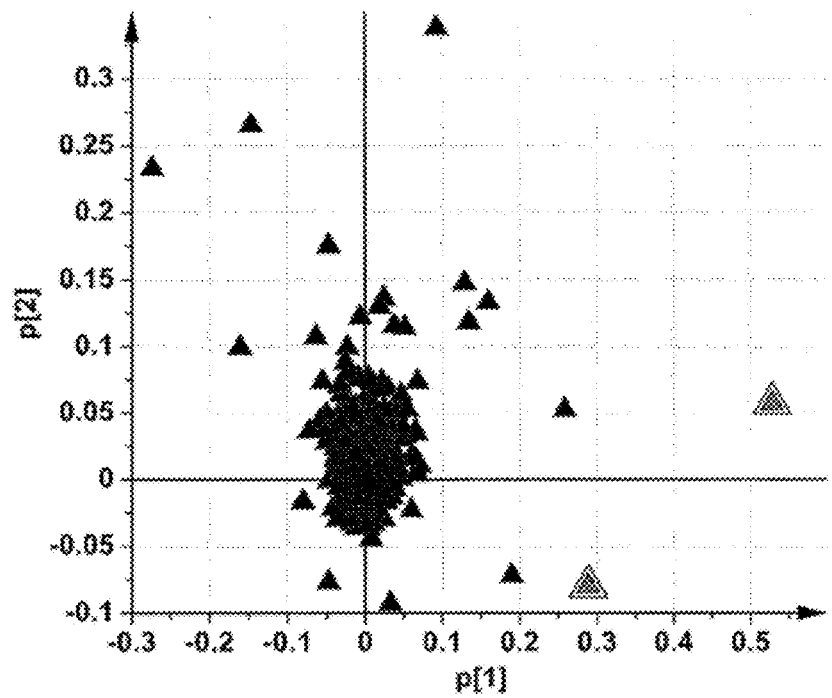

FIG. 20B shows a loadings scatter plot of all detected urine ions in the PCA model. The p[1] and p[2] values represent the contributing weights of each ion to principal components 1 and 2. The identities of two ions with the highest loading values are annotated in the plot. All the data were obtained in electrospray inoization negative mode (ESI⁻).

Figure 20C:
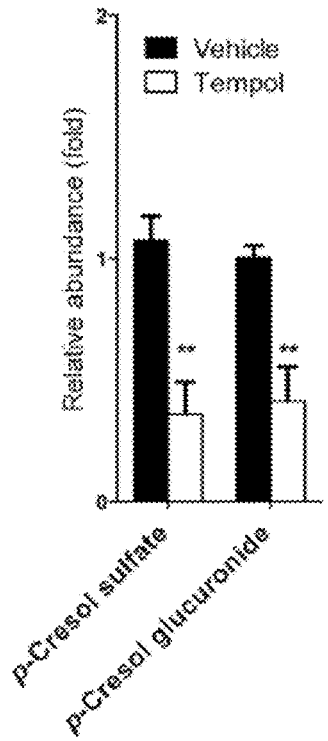

FIG. 20C shows urine levels of p-cresol sulfate and p-cresol glucuronide. Values were normalized to those of vehicle-treated mice and were expressed as relative abundance.

Figure 20D:
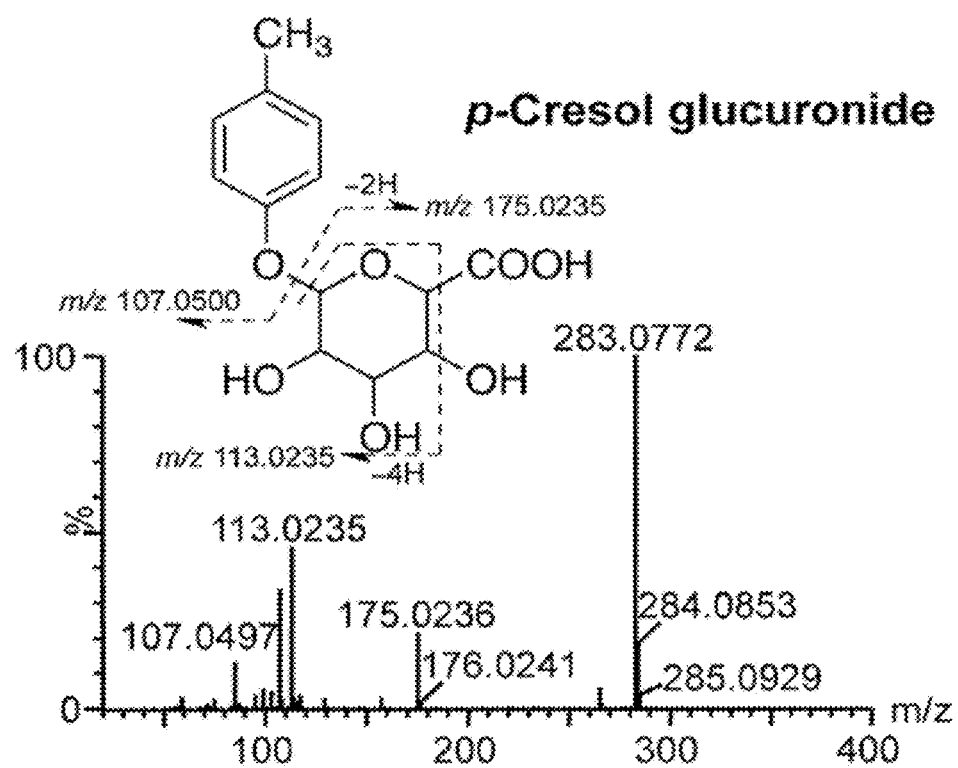
Figure 20E:
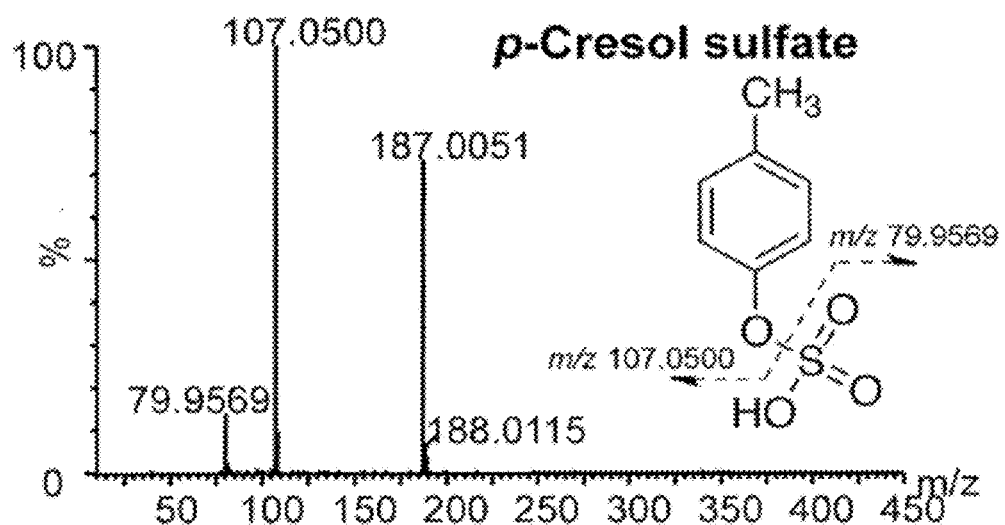

FIGS. 20D and E show tandem MS and chemical structures of p-cresol sulfate (20D) and p-cresol glucuronide (20E).

Figure 21A:
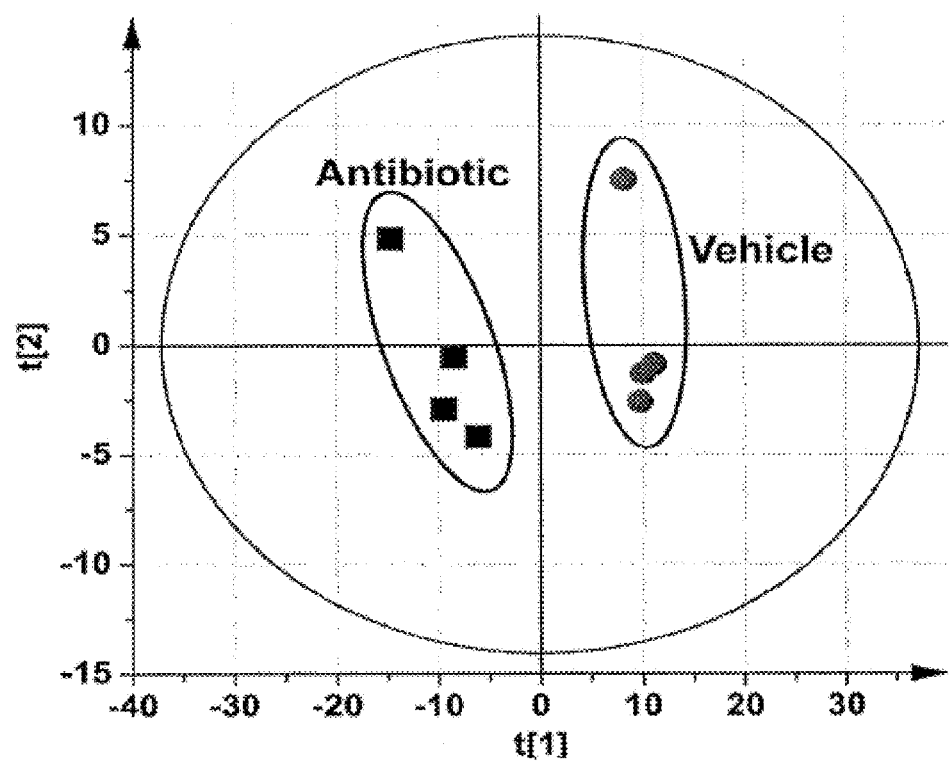

FIG. 21A shows scores scatter plot of a PCA model of urine ions in vehicle- and tempol-treated mice after 14 weeks of high-fat diet treatment.

Figure 21B:
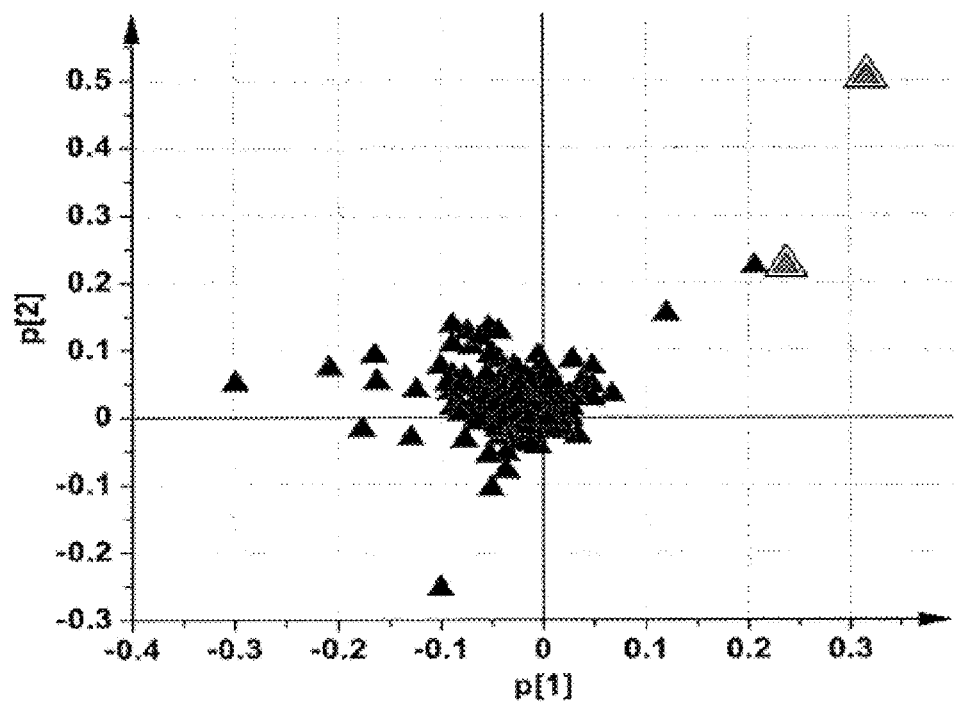

FIG. 21B shows loadings scatter plot of a PCA model of urine ions in vehicle- and antibiotic-treated mice after 14 weeks of HFD. The p[1] and p[2] values represent the contributing weights of each ion to principal components 1 and 2. The identities of two ions with the highest loading values are annotated in the plot. All the data were obtained in negative mode (ESI⁻).

Figure 21C:
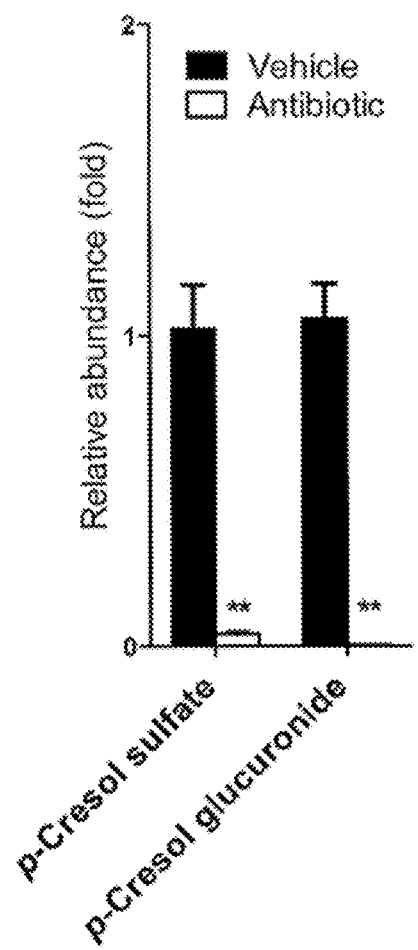

FIG. 21C shows urine levels of p-cresol sulfate and p-cresol glucuronide in vehicle- and antibiotic-treated mice after 14 weeks of high-fat diet treatment. Values were normalized to those of vehicle-treated mice and were expressed as relative abundance. n=5 mice per group. All data are presented as mean±SD. Analysis of variance followed by two-tailed Student's t-test. *P<0.05, **P<0.01 compared to vehicle-treated mice.

Figure 22A:
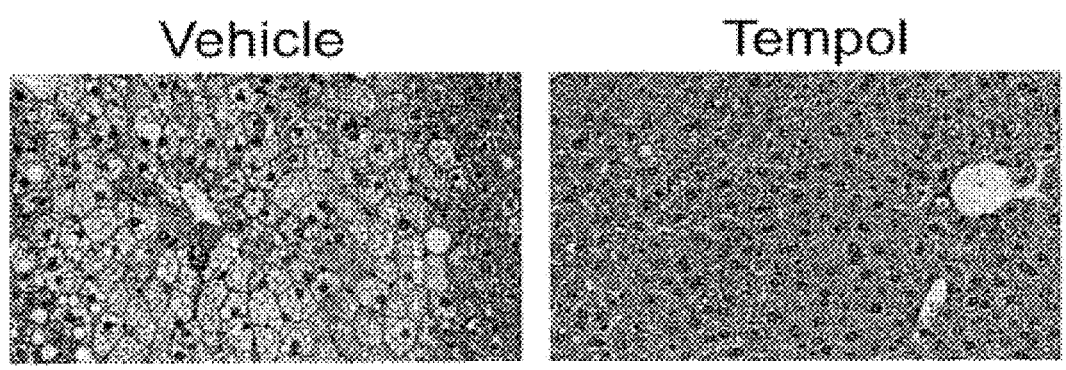

FIG. 22A shows representative H&E staining of liver sections from vehicle- and tempol-treated mice fed a high-fat diet for 14 weeks.

Figure 22B:
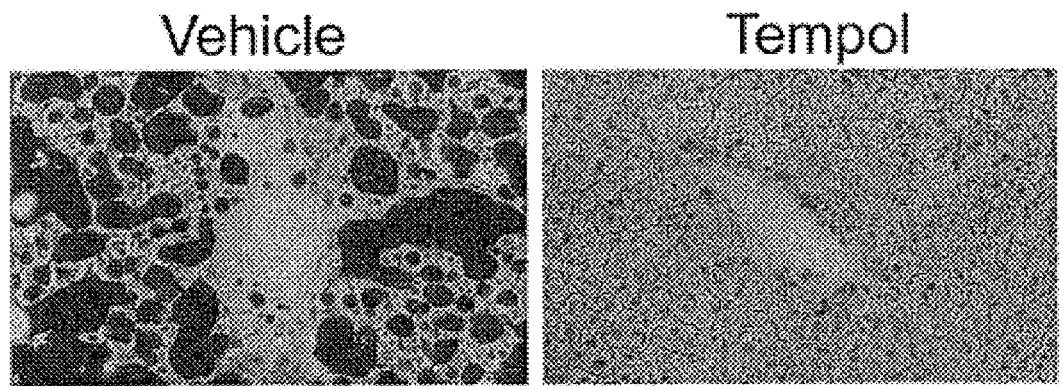

FIG. 22B shows representative Oil Red 0 staining of lipid droplets in liver sections from vehicle- and tempol-treated mice fed a high-fat diet for 14 weeks.

Figure 22C:
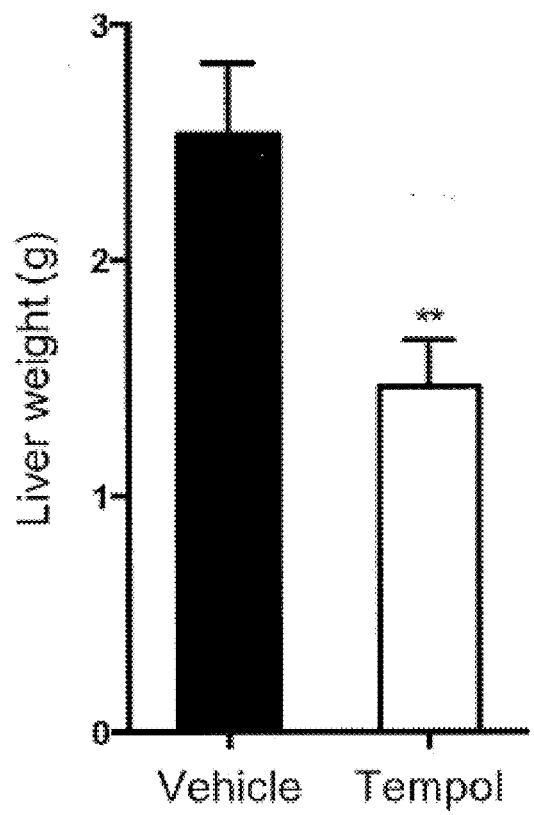

FIG. 22C shows liver weights from vehicle- and tempol-treated mice fed a high-fat diet for 16 weeks.

Figure 22D:
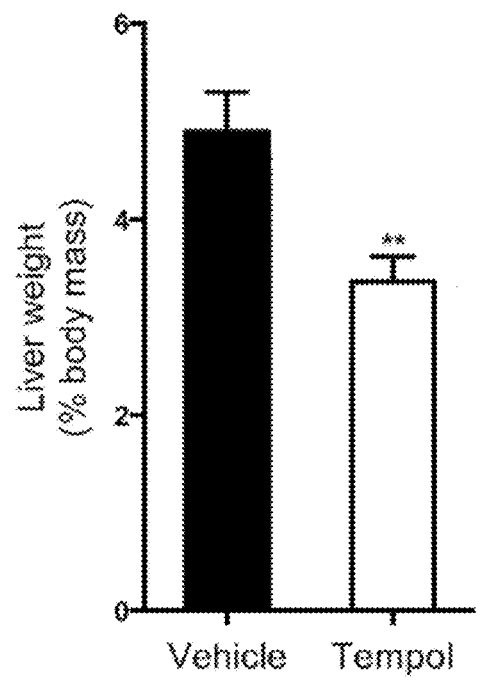

FIG. 22D shows liver weight to body weight ratios in vehicle- and tempol-treated mice fed a high-fat diet for 16 weeks.

Figure 22E:
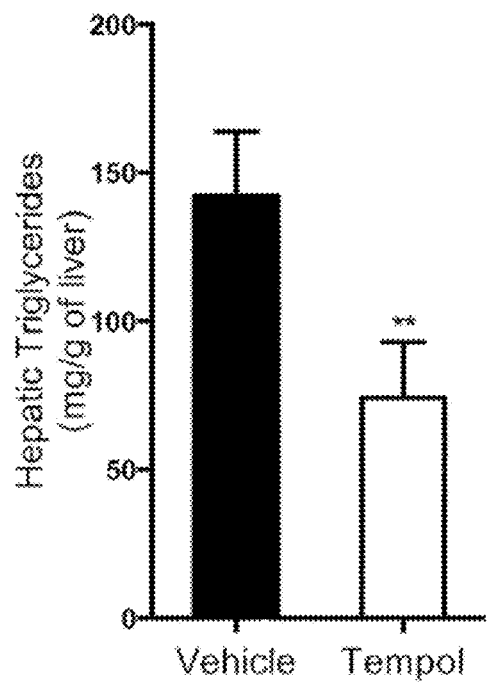

FIG. 22E shows liver triglyceride (TG) contents from vehicle- and tempol-treated mice fed a high-fat diet for 16 weeks.

Figure 23A:
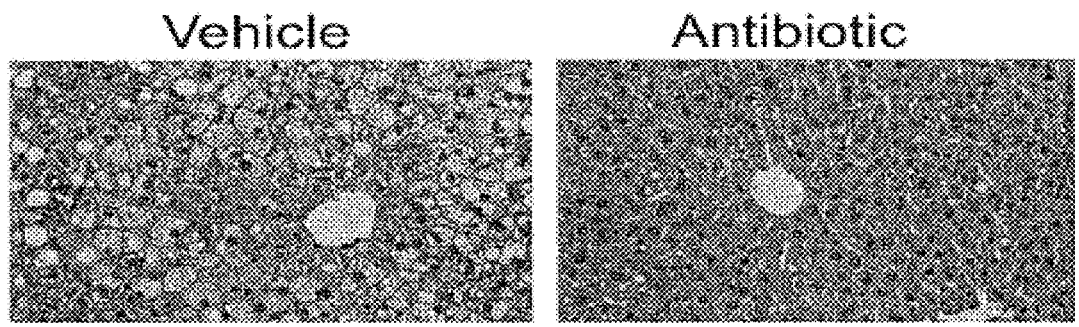

FIG. 23A shows representative H&E staining of liver sections from vehicle- and tempol-treated mice fed a high-fat diet for 16 weeks.

Figure 23B:
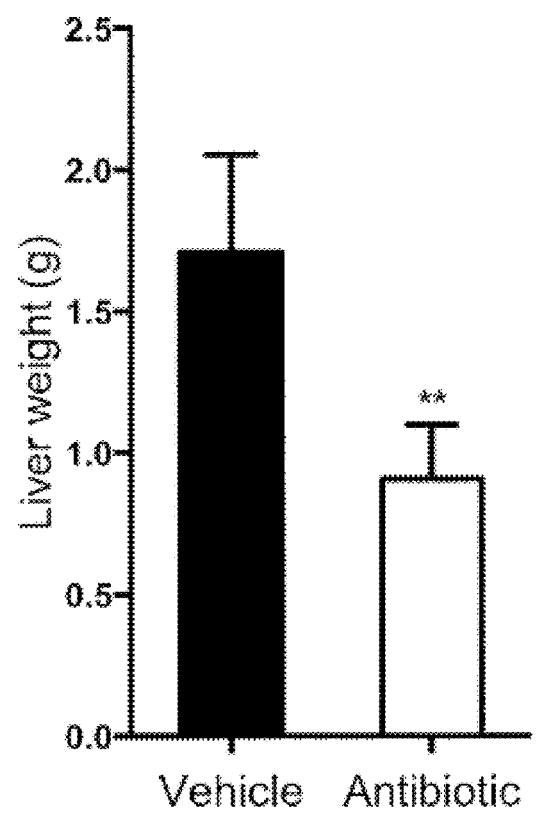

FIG. 23B shows liver weights from vehicle- and tempol-treated mice fed a high-fat diet for 16 weeks.

Figure 23C:
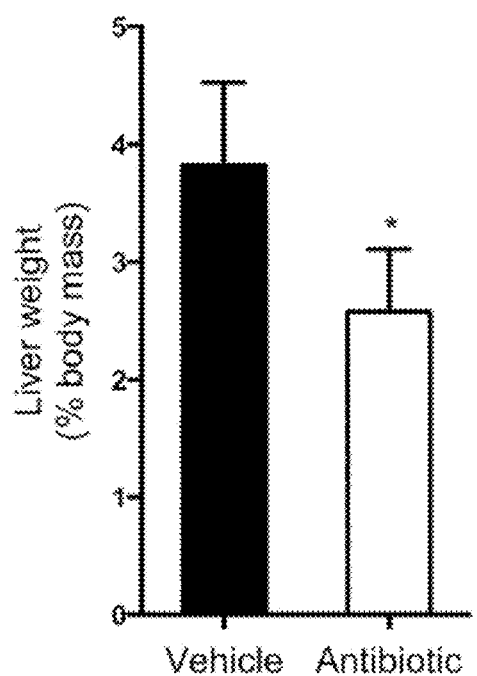

FIG. 23C shows liver weight to body weight ratios from vehicle- and tempol-treated mice fed a high-fat diet for 16 weeks.

Figure 23D:
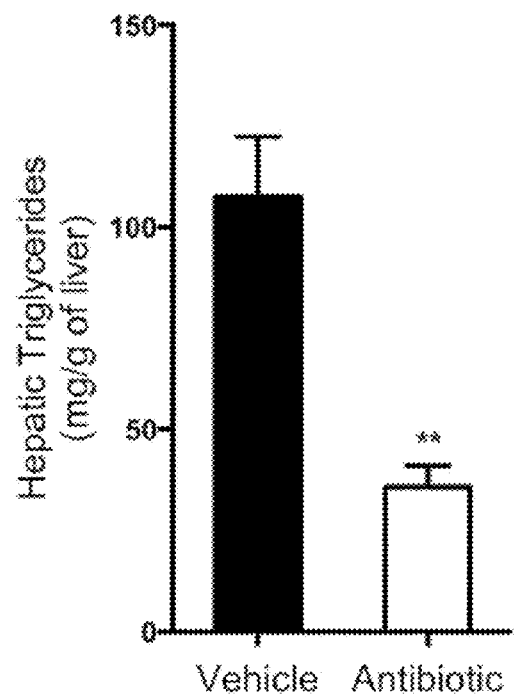

FIG. 23D shows liver TG contents from vehicle- and antibiotic-treated fed a high-fat diet for 16 weeks.

Figure 24A:
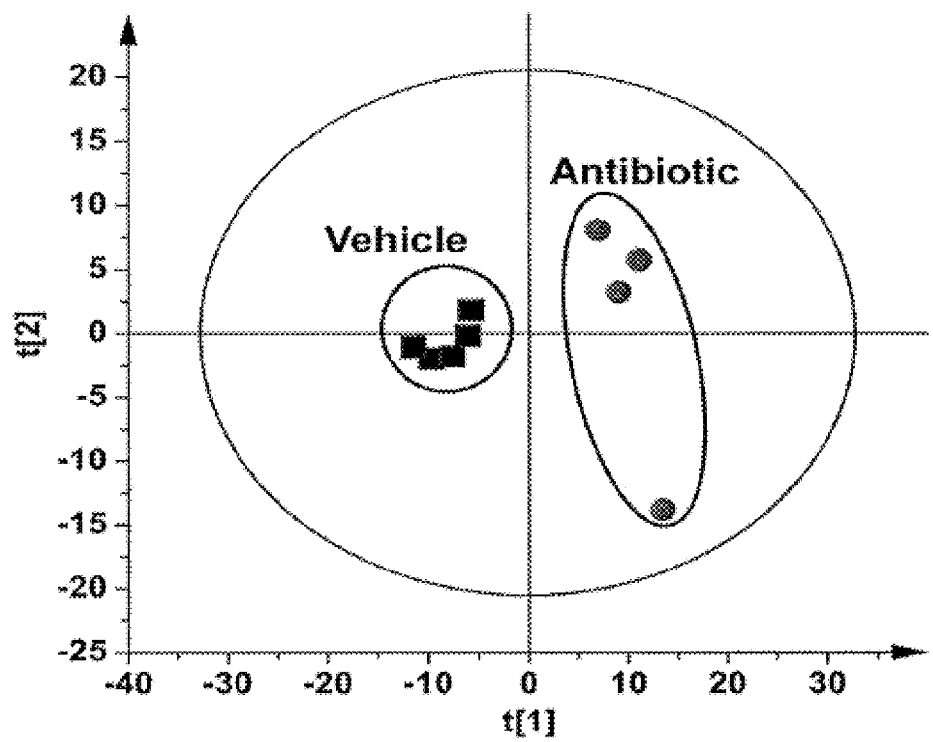

FIG. 24A shows a scores scatter plot of a PCA model of ileum ions from vehicle- and antibiotic-treated mice fed a high-fat diet for 7 weeks.

Figure 24B:
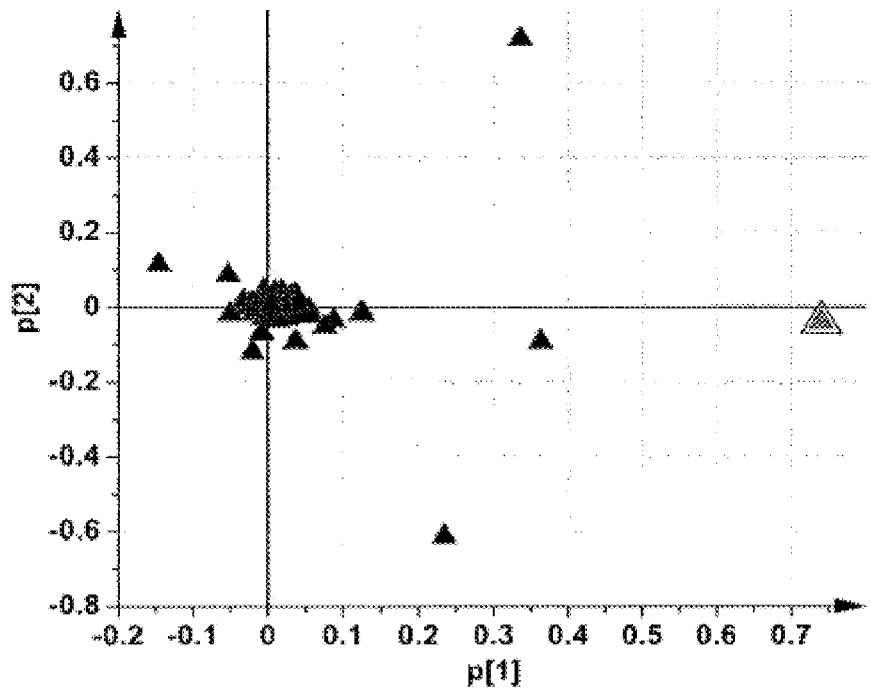

FIG. 24B shows loadings scatter plot of a PCA model of ileum ions in vehicle- and antibiotic-treated mice fed a high-fat diet for 7 weeks. The p[1] and p[2] values represent the contributing weights of each ion to principal components 1 and 2. The identities of two ions with the highest loading values are annotated in the plot. All the data were obtained in negative mode (ESI⁻).

Figure 25A:
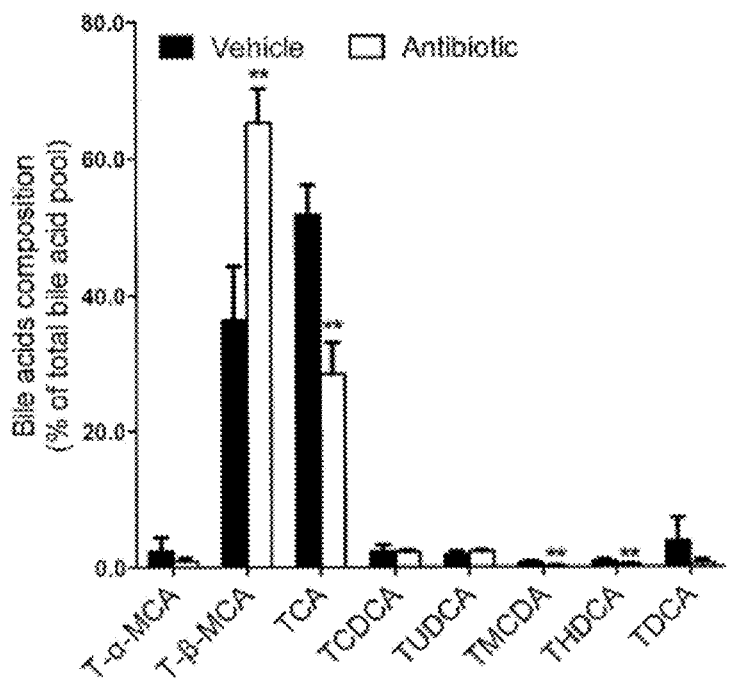

FIG. 25A shows the ratio of individual taurine-conjugated bile acids to total bile acids in the ileum from vehicle- and antibiotic-treated mice fed a high-fat diet for 14 weeks.

Figure 25B:
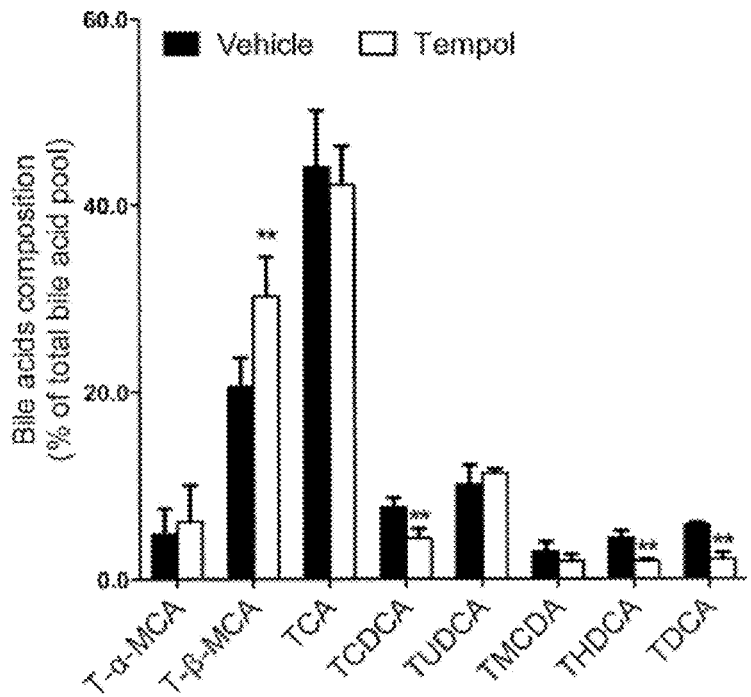

FIG. 25B shows the ratio of individual taurine-conjugated bile acids to total bile acids in the ileum from vehicle- and tempol-treated mice fed a high-fat diet for 7 weeks.

Figure 26A:
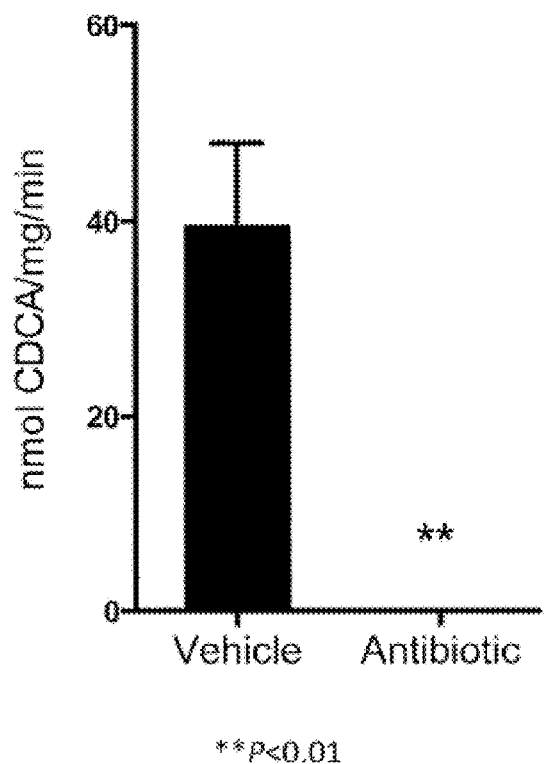

FIG. 26A shows fecal BSH enzyme activity from vehicle- and antibiotic-treated mice fed a high-fat diet for 7 weeks. n=4-5 mice per group.

Figure 26B:
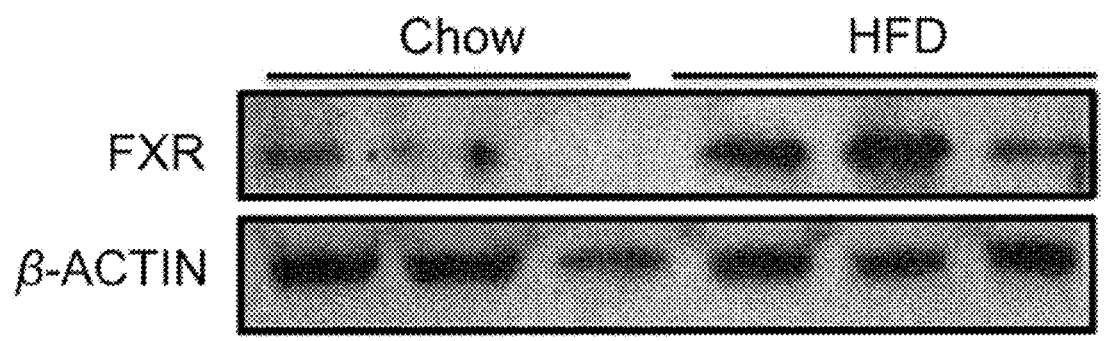

FIG. 26B shows western blot analysis of ileum FXR expression in mice fed a high-fat diet for 12 weeks. Each lane represents one mouse.

Figure 26C:
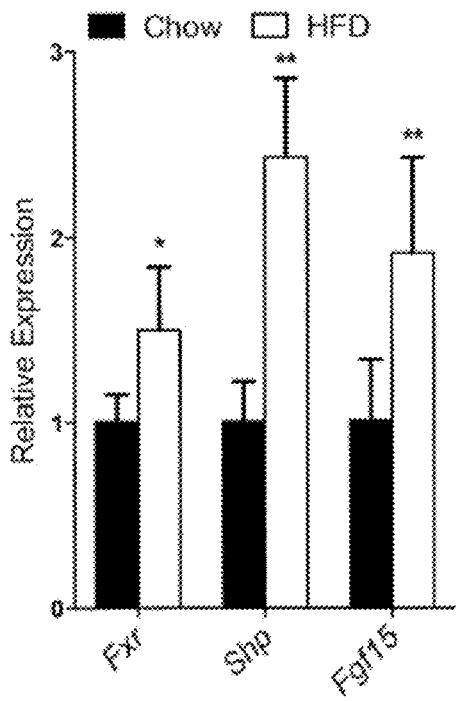

FIG. 26C shows Fxr mRNA levels and mRNA levels of the FXR target genes Shp and Fgf15 in the ileum from mice fed a high-fat diet for 12 weeks. n=3 mice per group.

Figure 26D:
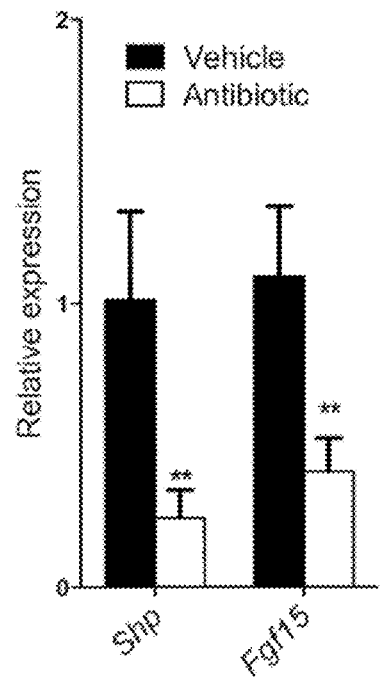

FIG. 26D shows mRNA levels of the FXR target genes Shp and Fgf15 in the ileum from vehicle- and antibiotic-treated mice fed a high-fat diet for 7 weeks. n=3 mice per group.

Figure 26E:
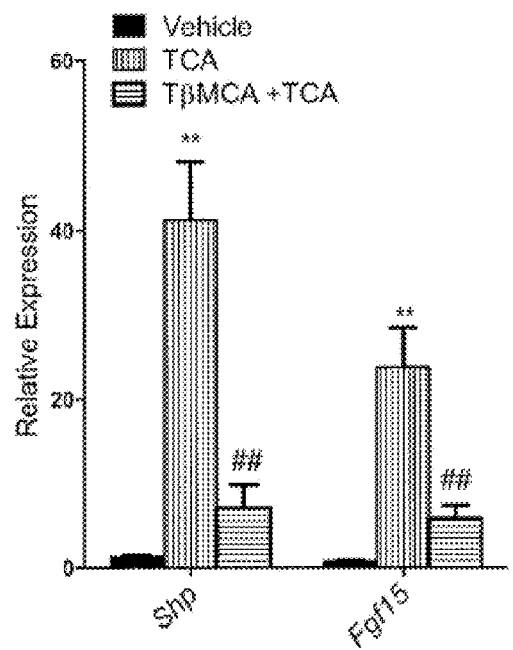

FIG. 26E shows mRNA levels of the FXR target genes Shp and Fgf15 in the ileum after 24 hours of treatment of mice fed a high-fat diet for 7 weeks with vehicle, taurocholic acid (TCA), and taurine-β-muricholic acid (TβMCA) with TCA. n=3 mice per group.

Figure 27A:
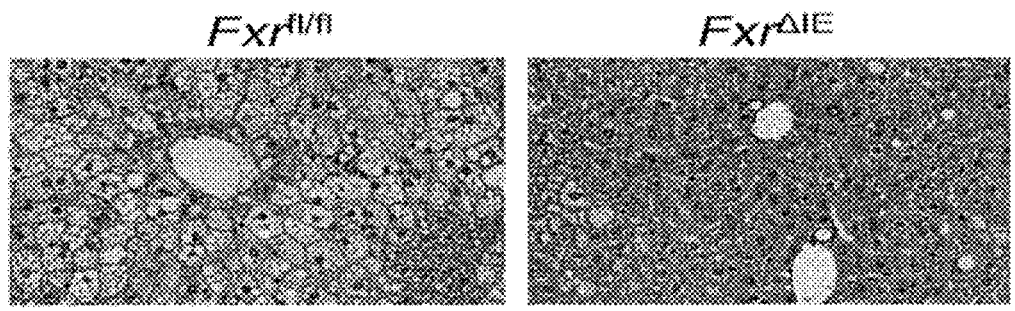

FIG. 27A shows a representative H&E staining of liver sections from control-floxed ($Fxr^{fl/fl}$) mice and intestine-specific knockout mice ($Fxr^{ΔIE}$) mice fed a high-fat diet for 14 weeks.

Figure 27B:
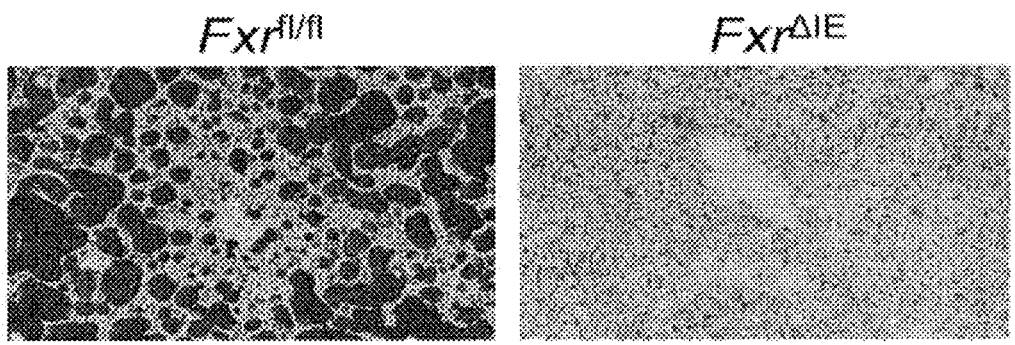

FIG. 27B shows a representative Oil Red 0 staining of lipid droplets in liver sections from $Fxr^{fl/fl}$ and $Fxr^{ΔIE}$ mice fed a high-fat diet for 14 weeks.

Figure 27C:
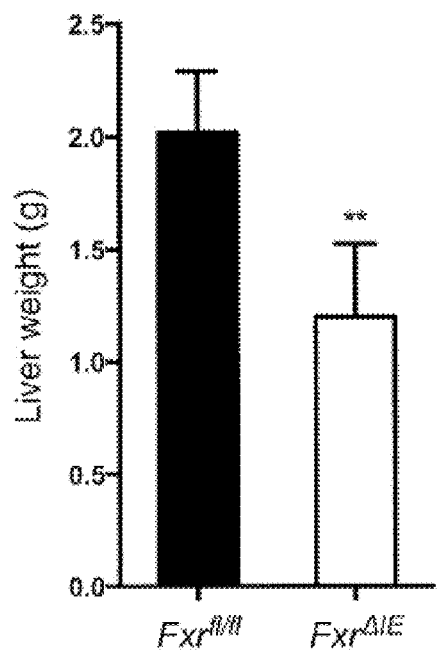

FIG. 27C shows liver weights from $Fxr^{fl/fl}$ and $Fxr^{ΔIE}$ mice fed a high-fat diet for 14 weeks.

Figure 27D:
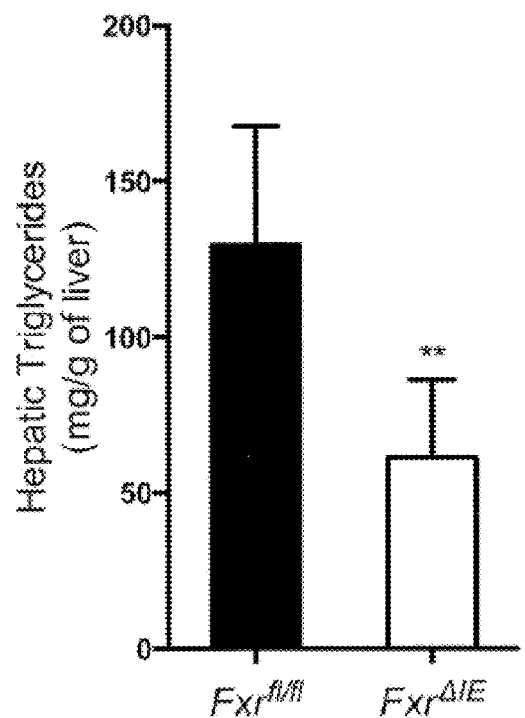

FIG. 27D shows liver triglyceride contents from $Fxr^{fl/fl}$ and $Fxr^{ΔIE}$ mice fed a high-fat diet for 14 weeks.

Figure 28A:
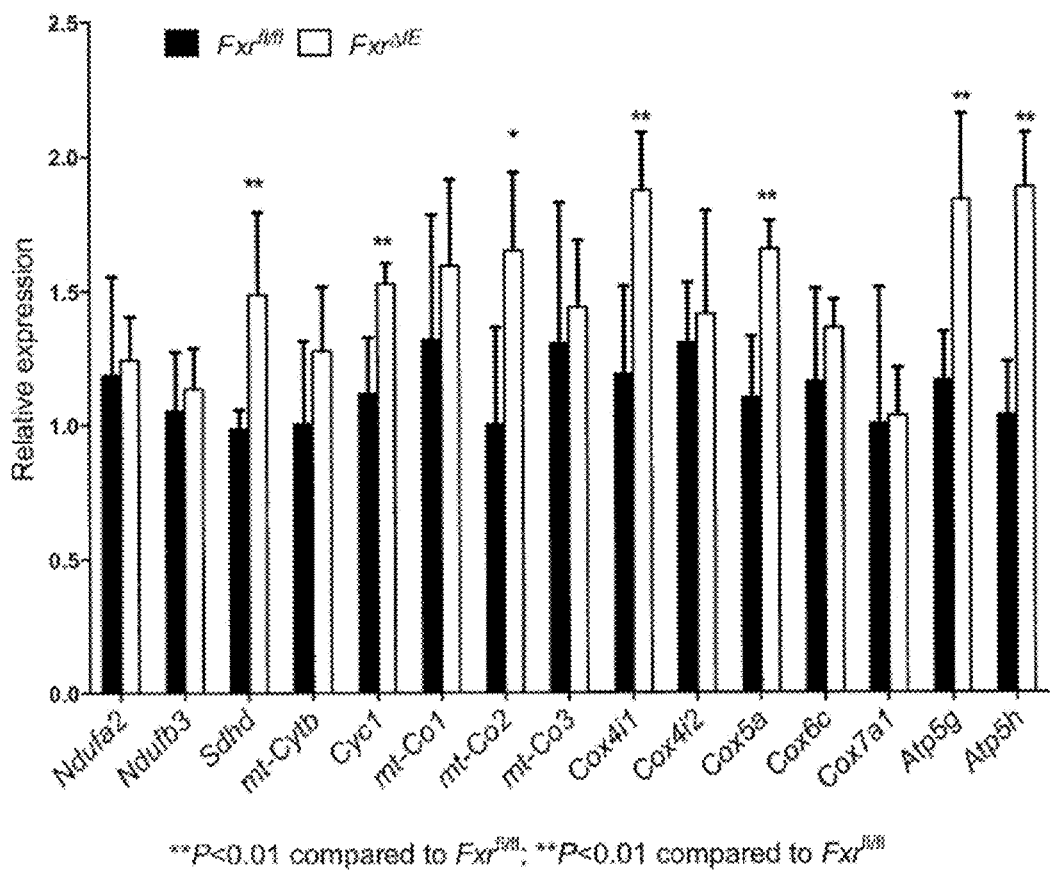

FIG. 28A shows mRNA levels of mitochondrial oxidative phosphorylation (OXPHOS) related enzymes from the ileum mucosa from $Fxr^{fl/fl}$ and $Fxr^{ΔIE}$ mice fed a high-fat diet for 14 weeks.

Figure 28B:
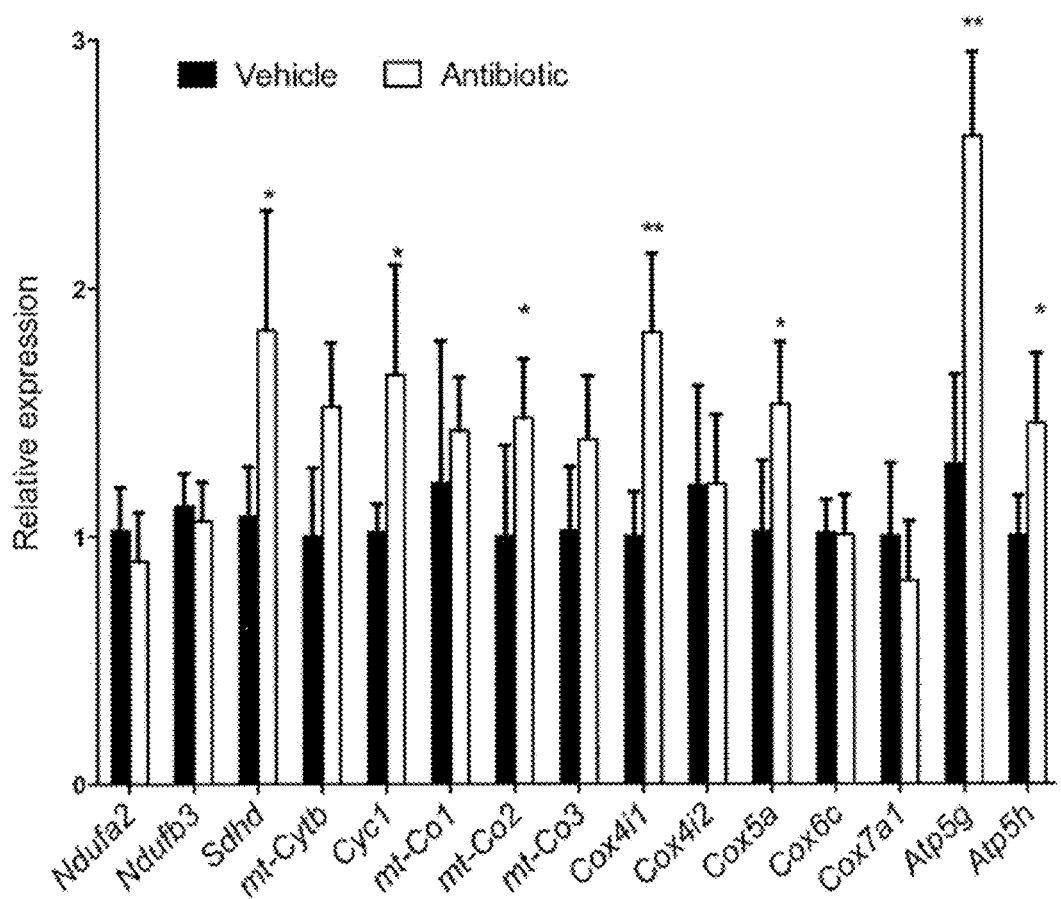

FIG. 28B shows mRNA levels of mitochondrial oxidative phosphorylation (OXPHOS)-related genes from ileum mucosa of vehicle- and antibiotic-treated mice fed a high-fat diet for 7 weeks. n=3 mice per group.

Figure 28C:
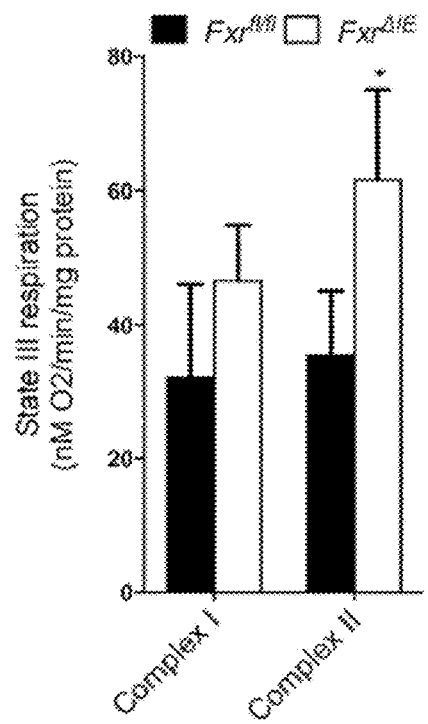

FIG. 28C shows measured state III respiration for complex-I- and complex-II-dependent respiration from the ileum mucosa from $Fxr^{fl/fl}$ and $Fxr^{ΔIE}$ mice fed a high-fat diet for 12 weeks.

Figure 28D:
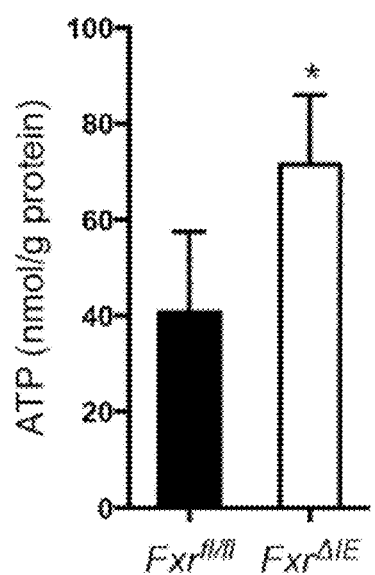

FIG. 28D shows ATP levels in the ileum mucosa of $Fxr^{fl/fl}$ mice and $Fxr^{ΔIE}$ mice fed a high-fat diet for 7 weeks.

Figure 29A:
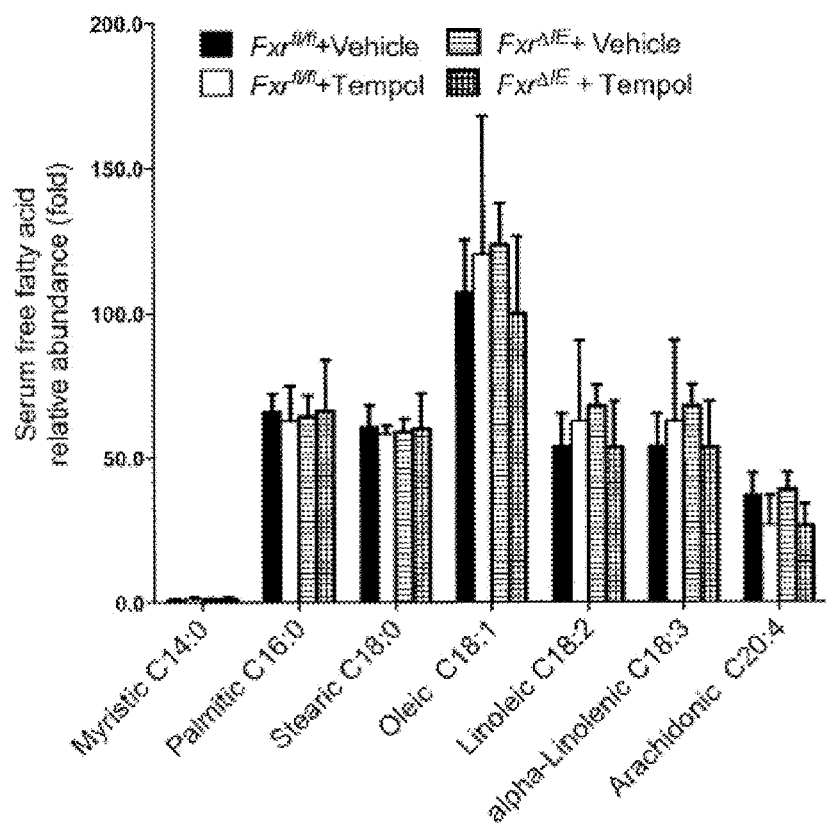

FIG. 29A shows serum free fatty acids. The bars for each fatty acid, from left to right, are from vehicle-treated $Fxr^{fl/fl}$ mice, tempol-treated $Fxr^{fl/fl}$ mice, vehicle-treated $Fxr^{ΔIE}$ mice and tempol-treated $Fxr^{ΔIE}$ mice.

Figure 29B:
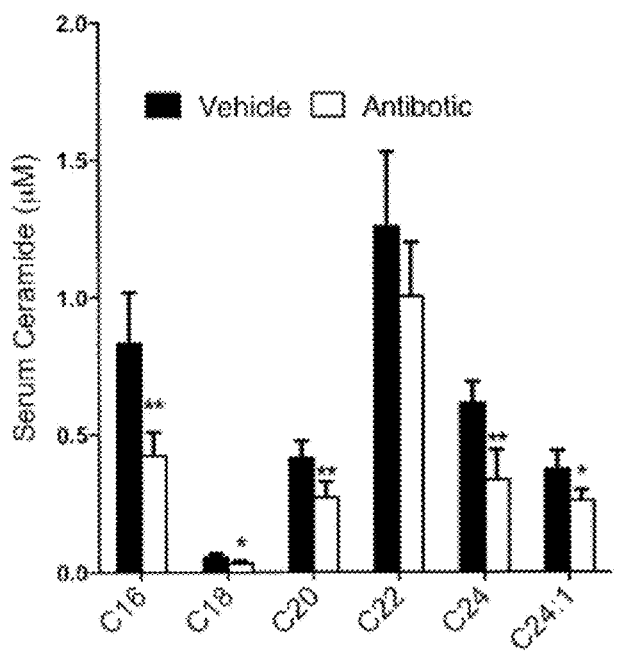

FIG. 29B shows serum ceramides from vehicle- and antibiotic-treated mice fed a high-fat diet for 7 weeks. n=3 mice per group.

Figure 29C:
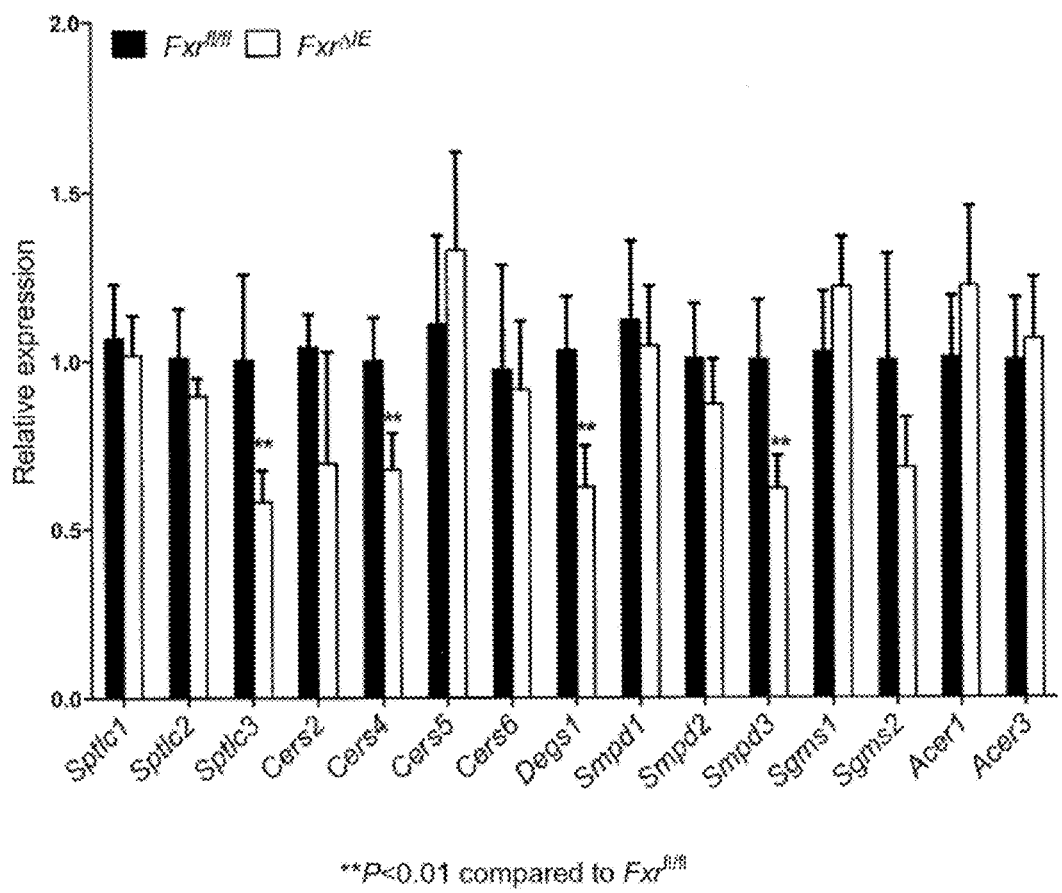

FIG. 29C shows expression of mRNAs encoding ceramide synthesis- and catabolism-related enzymes in the ileum from $Fxr^{fl/fl}$ and $Fxr^{ΔIE}$ mice fed a high-fat diet for 14 weeks.

Figure 29D:
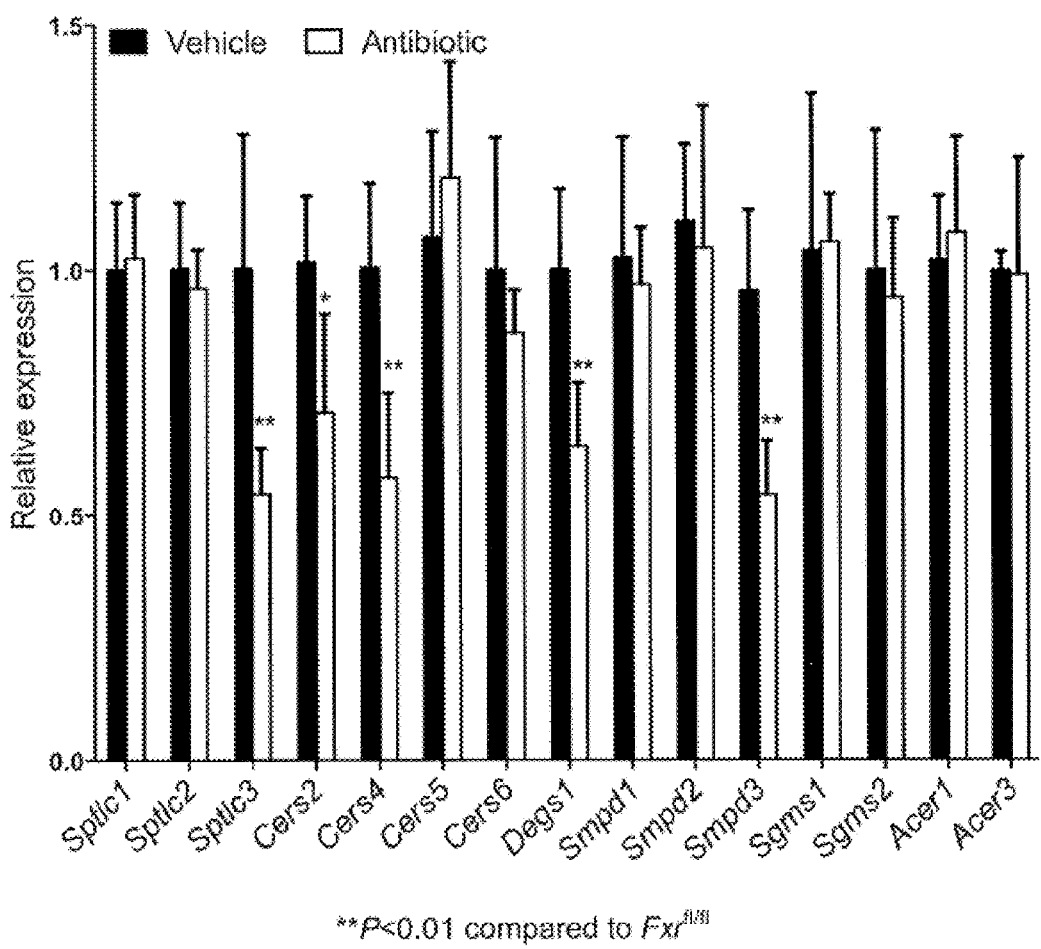

FIG. 29D shows levels of mRNAs encoding ceramide synthesis- and catabolism-related enzymes in the ileum after 7 weeks antibiotic of treatment of mice fed a high-fat diet for 14 weeks.

Figure 30A:
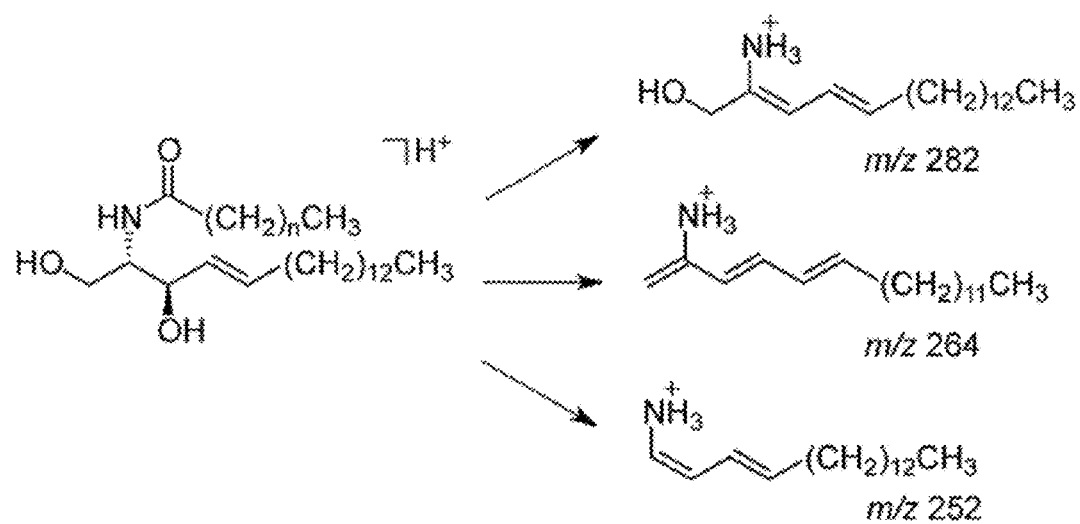
Figure 30B:
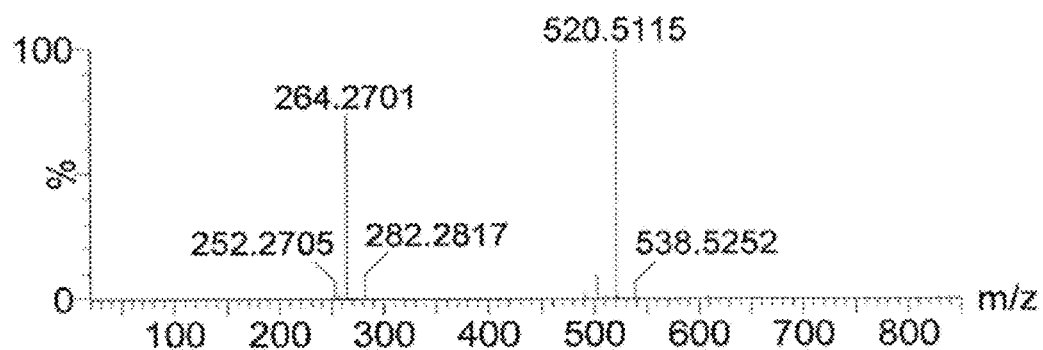
Figure 30C:
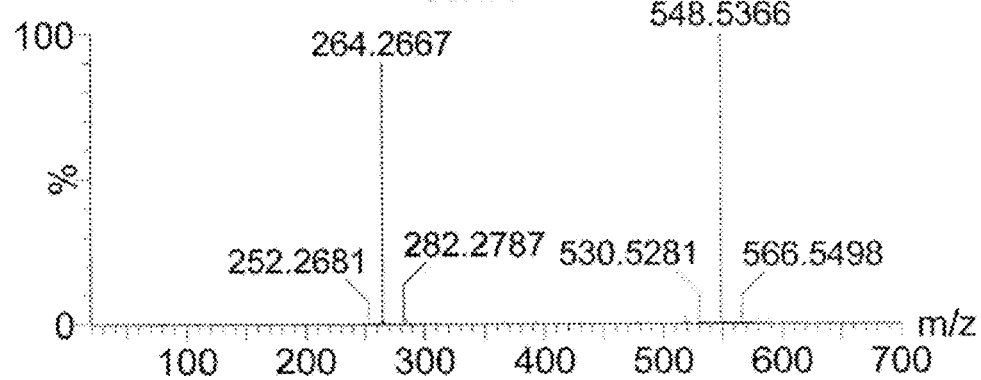
Figure 30D:
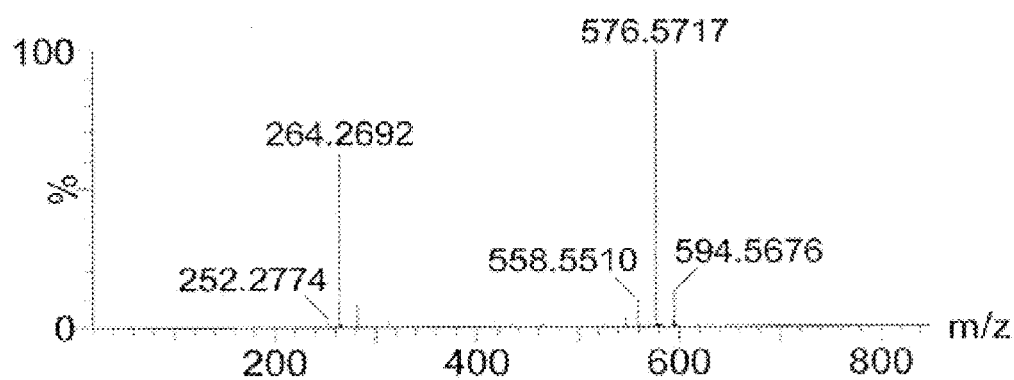
Figure 30E:
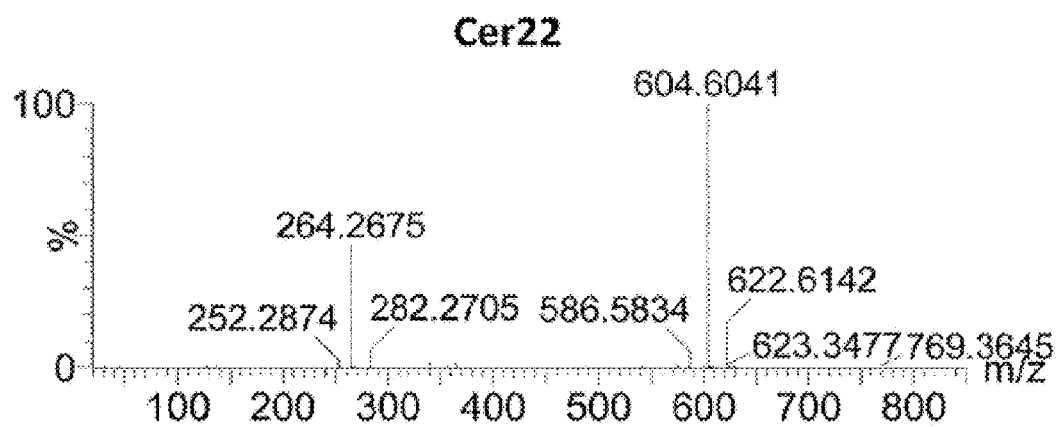
Figure 30F:
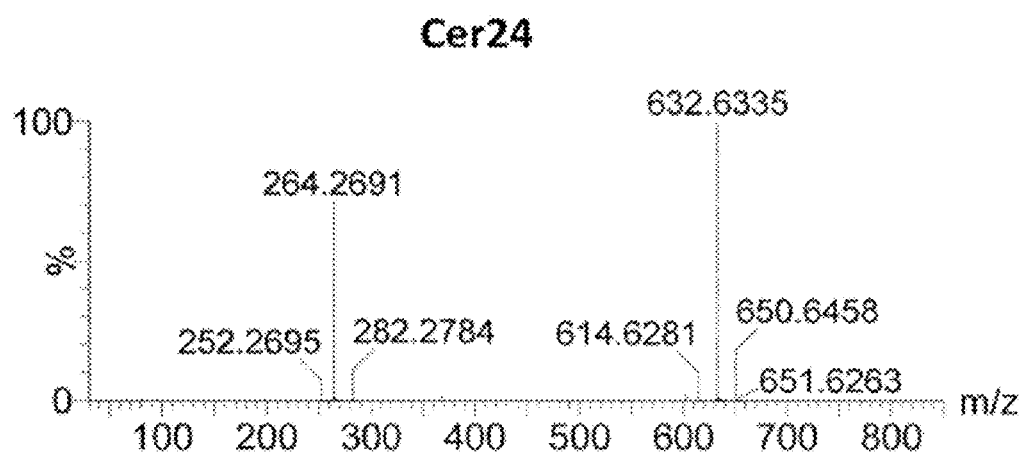
Figure 30G:
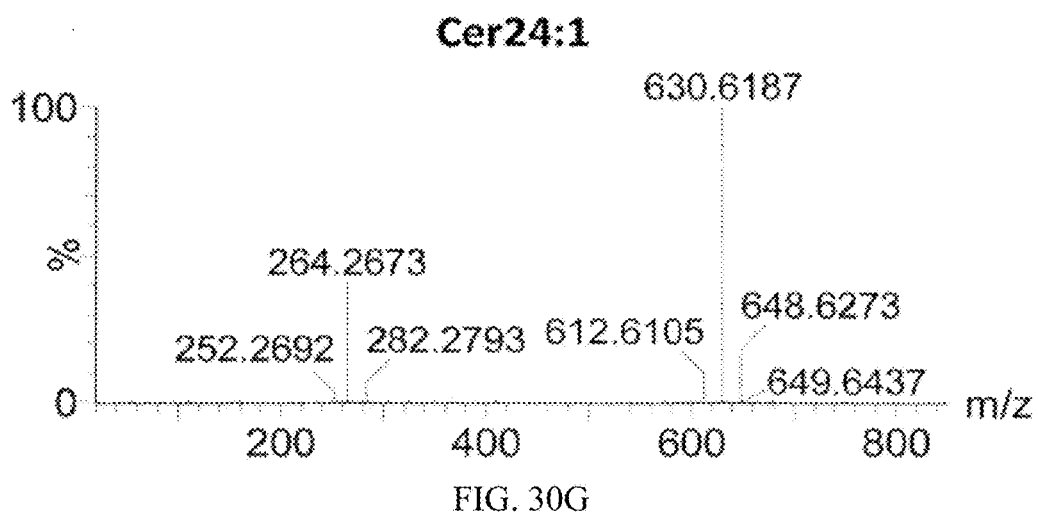

FIG. 30A shows the structure of MS fragments derived from ceramides and

FIG. 30B-30G shows tandem MS and chemical structures of the various ceramides.

Figure 31A:
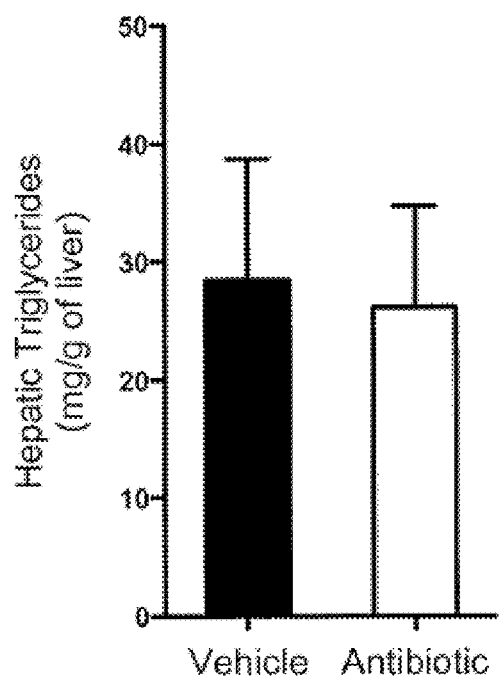

FIG. 31A shows liver TG contents in vehicle- and antibiotic-treated mice fed a high-fat diet for 3 days.

Figure 31B:
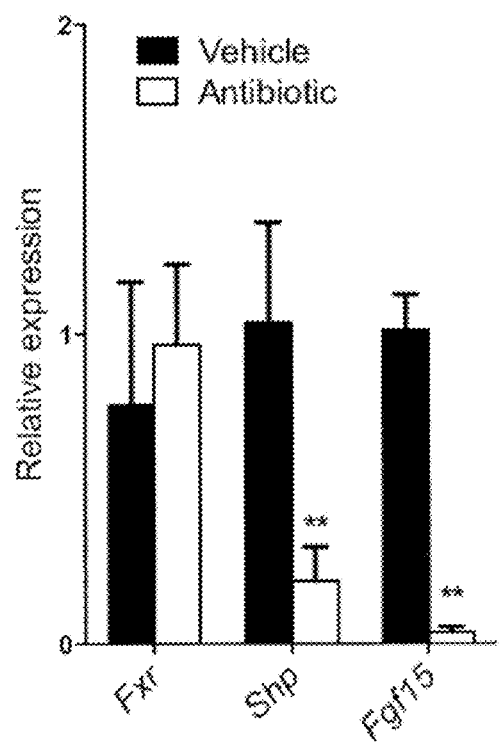

FIG. 31B shows Fxr, Shp and Fgf15 mRNA levels in the ileum of mice fed a high-fat diet for 14 weeks and then treated with vehicle or antibiotic for 3 days.

Figure 31C:
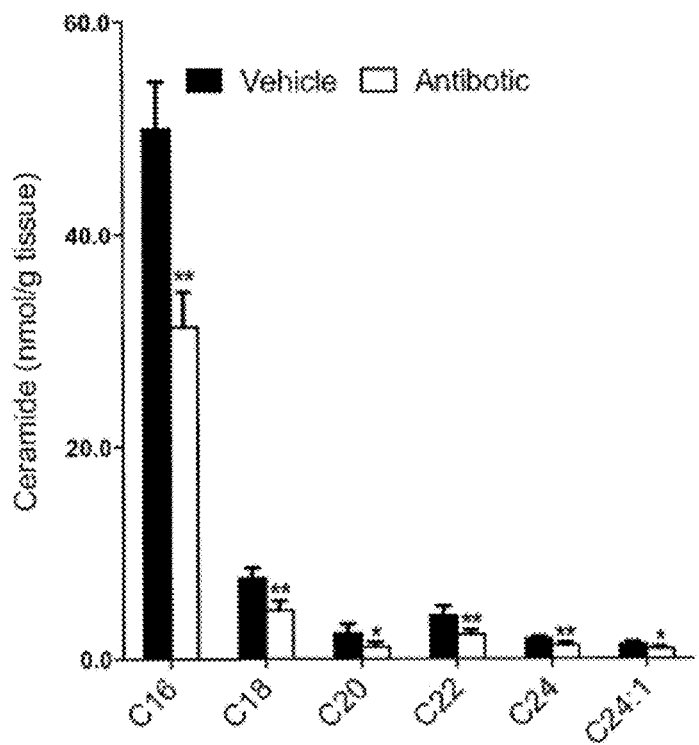

FIG. 31C shows the profile of ceramides from ileum from mice fed a high-fat diet for 14 weeks, and then treated with vehicle or antibiotic for 3 days.

Figure 31D:
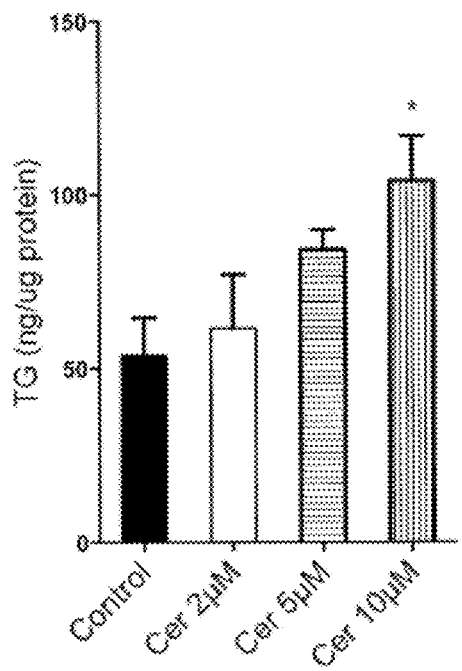

FIG. 31D shows primary hepatocyte triglyceride (TG) content after 24 hours of incubation with vehicle and 2 μM, 5 μM and 10 μM ceramide (n=4).

Figure 31E:
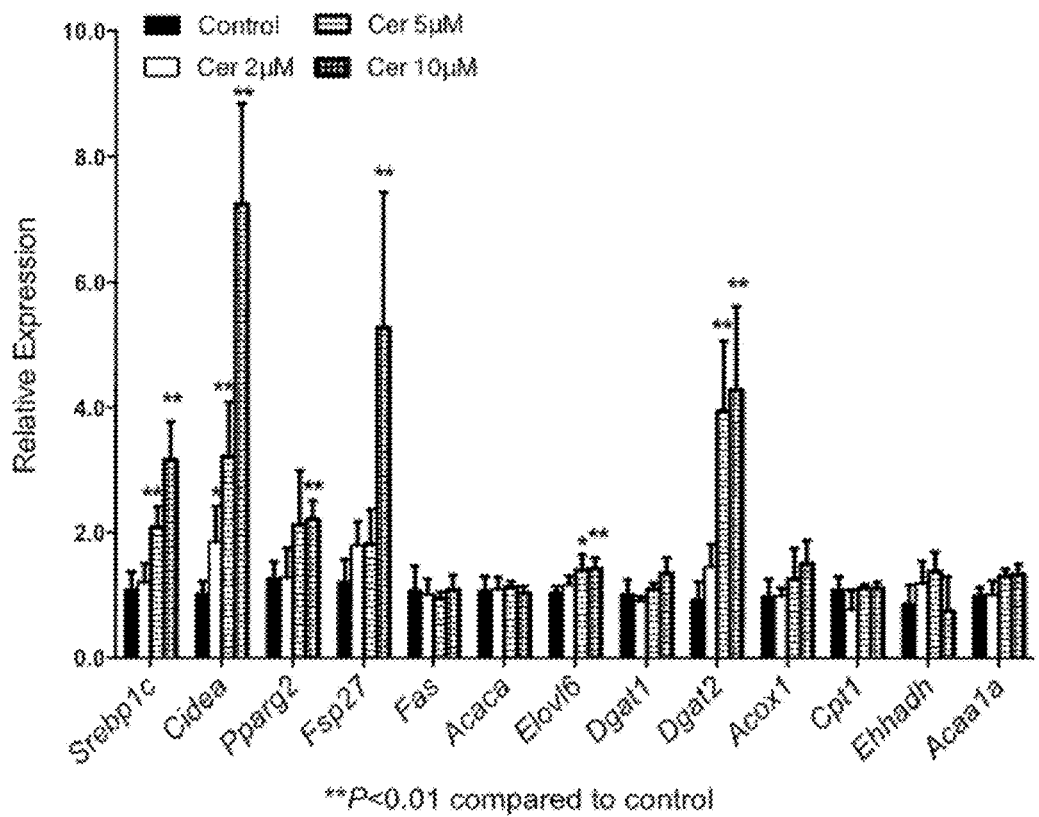

FIG. 31E shows mRNA levels of fatty acid synthesis, triglyceride synthesis, and fatty acid catabolism related genes in primary hepatocytes after 16 hours of incubation with vehicle and 2 μM, 5 μM and 10 μM ceramide (left to right bar for each mRNA, respectively, n=5).

Figure 31F:
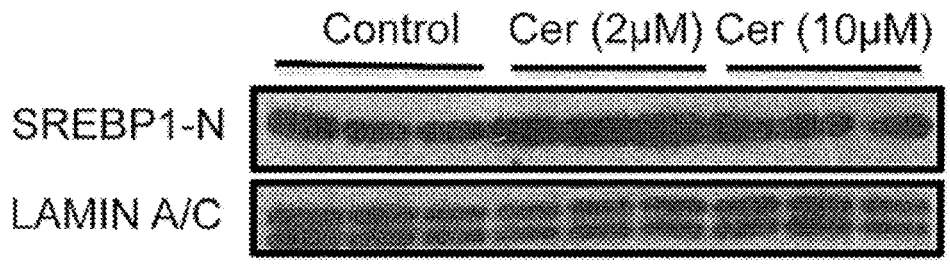

FIG. 31F shows western blot analysis of nuclear SREBP1-N expression in primary hepatocytes after 24 hours of incubation with vehicle, and 2 μM and 10 μM ceramide (n=3).

Figure 31G:
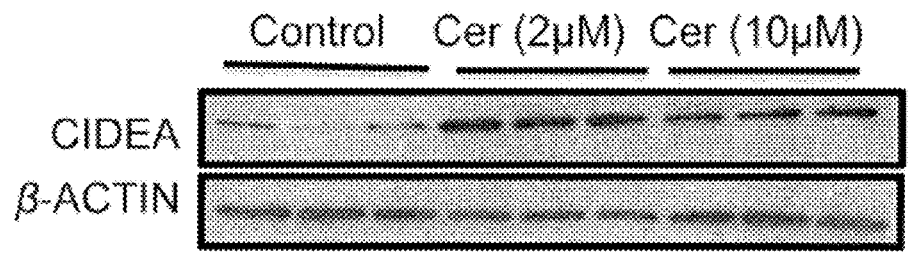

FIG. 31G shows western blot analysis of CIDEA expression in primary hepatocytes after 24 hours of incubation with vehicle, and 2 μM and 10 μM ceramide (n=3).

Figure 32A:
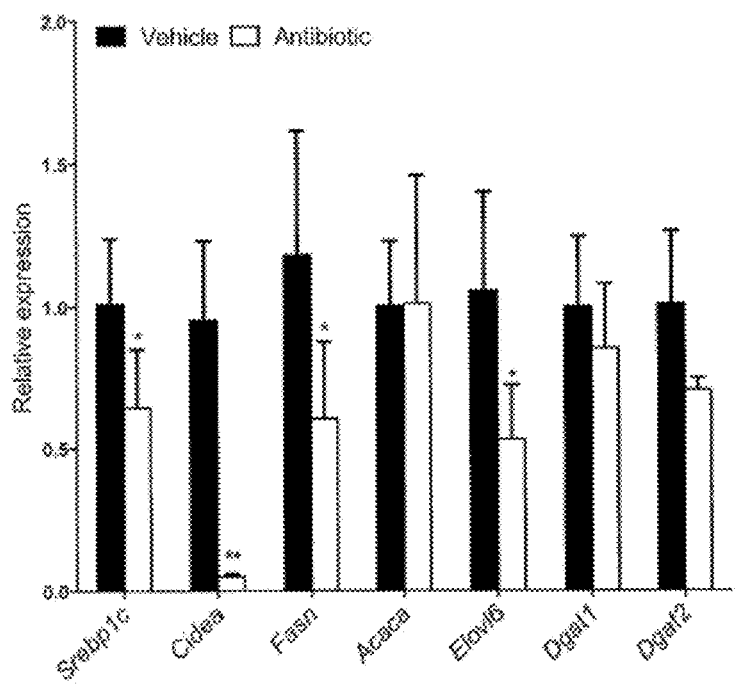

FIG. 32A shows levels of mRNAs encoding fatty acid synthesis and triglyceride synthesis related enzymes in the livers from vehicle- and antibiotic-treated mice fed a high-fat diet for 14 weeks.

Figure 32B:
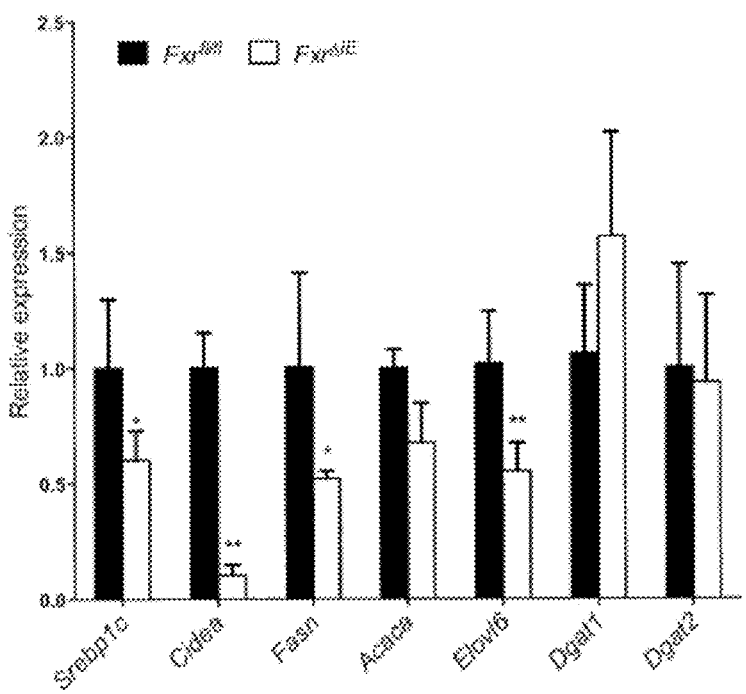

FIG. 32B shows expression of mRNAs encoding enzymes involved in fatty acid and triglyceride synthesis in the livers of $Fxr^{fl/fl}$ and $Fxr^{\Delta IE}$ mice fed a high-fat diet for 14 weeks.

Figure 32C:
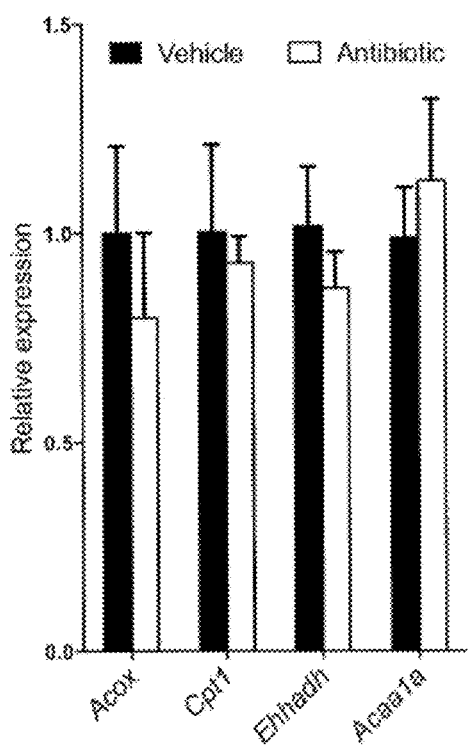

FIG. 32C shows mRNA levels of fatty acid oxidation-related genes in the livers from mice fed a high-fat diet for 7 weeks.

Figure 32D:
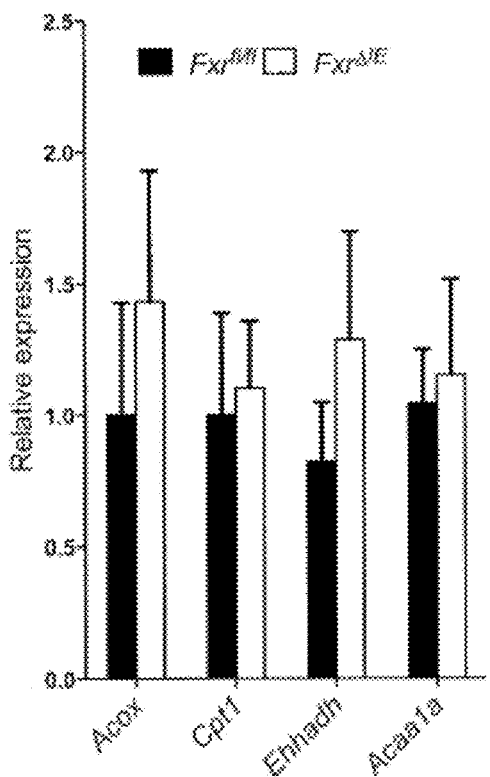

FIG. 32D shows mRNA levels of fatty acid oxidation-related genes in the livers from $Fxr^{fl/fl}$ mice and $Fxr^{\Delta IE}$ mice fed a high-fat diet for 14 weeks.

Figure 32E:
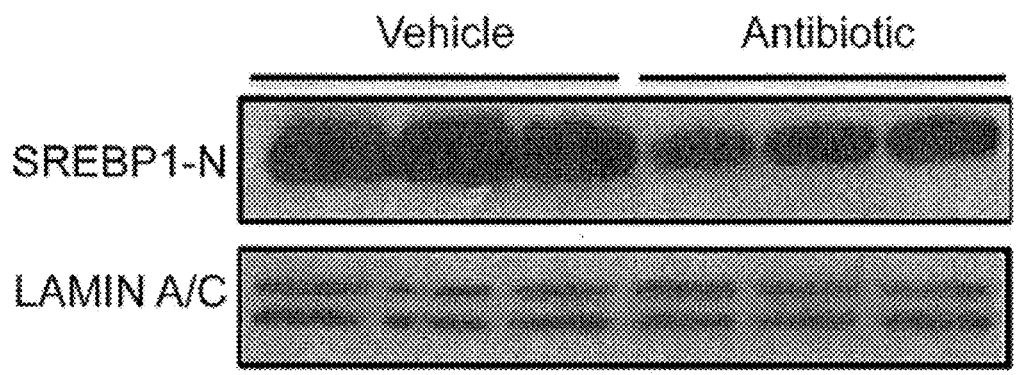

FIG. 32E shows western blot analysis of SREBP1-N protein expression in livers from vehicle- and antibiotic-treated mice fed a high-fat diet for 7 weeks. LAMIN A/C is used as a loading control (n=3).

Figure 32F:
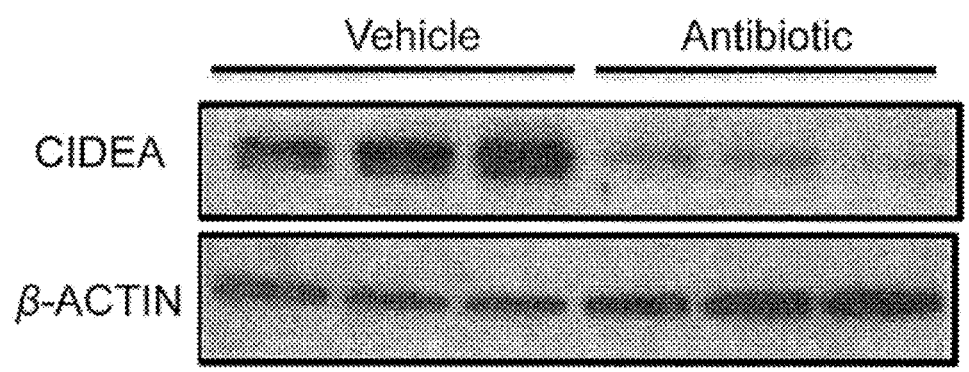

FIG. 32F shows western blot analysis of CIDEA protein expression in livers of vehicle- and antibiotic-treated mice fed a high-fat diet for 7 weeks. β-ACTIN is used as a loading control (n=3).

Figure 32G:
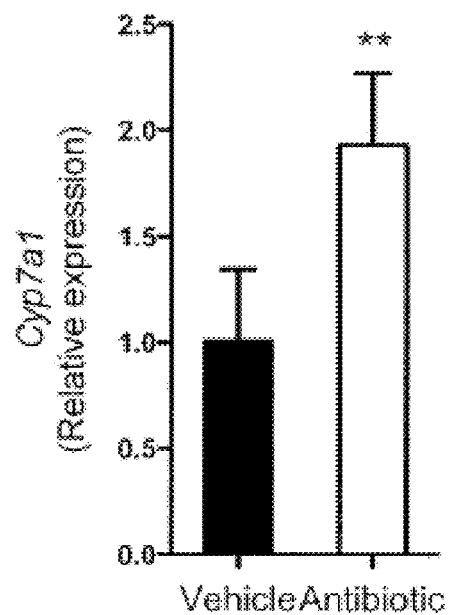

FIG. 32G shows Cyp7a1mRNA levels in the livers of vehicle- and antibiotic-treated mice fed a high-fat diet for 7 weeks (n=3).

Figure 32H:
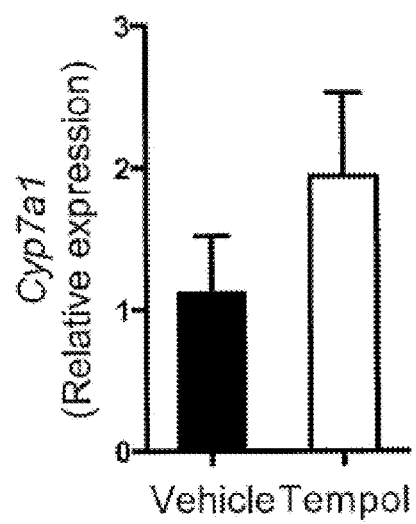

FIG. 32H shows Cyp7a1mRNA levels in the livers of vehicle- and tempol-treated mice fed a high-fat diet for 7 weeks (n=3).

Figure 32I:
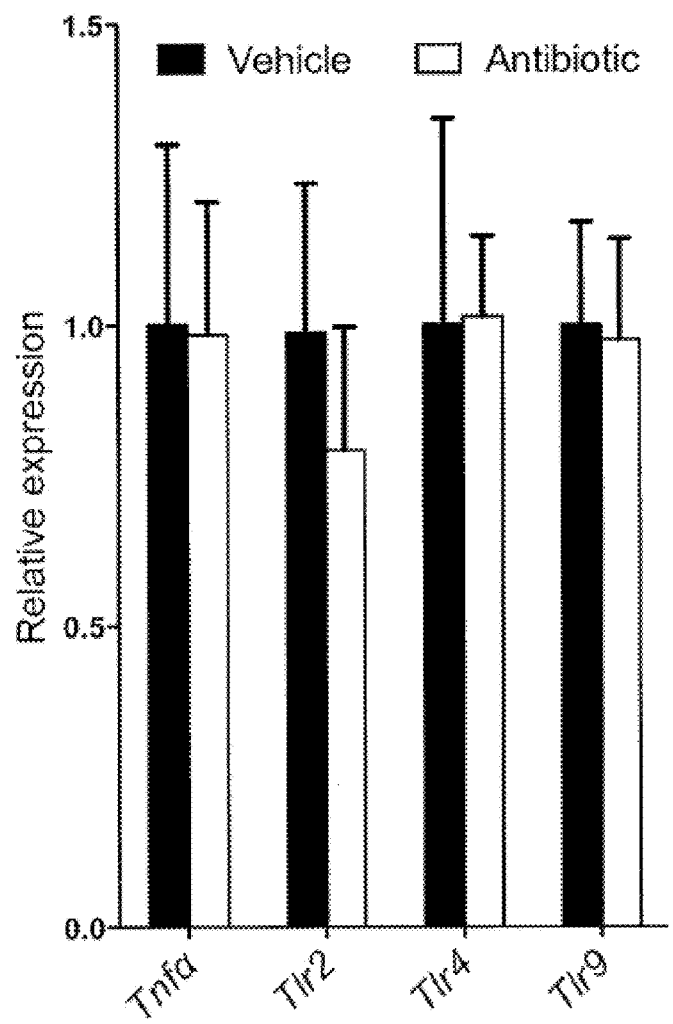

FIG. 32I shows mRNA levels of inflammation related genes in the livers of vehicle- and antibiotic-treated fed a high-fat diet for 7 weeks. (n=3).

Figure 32J:
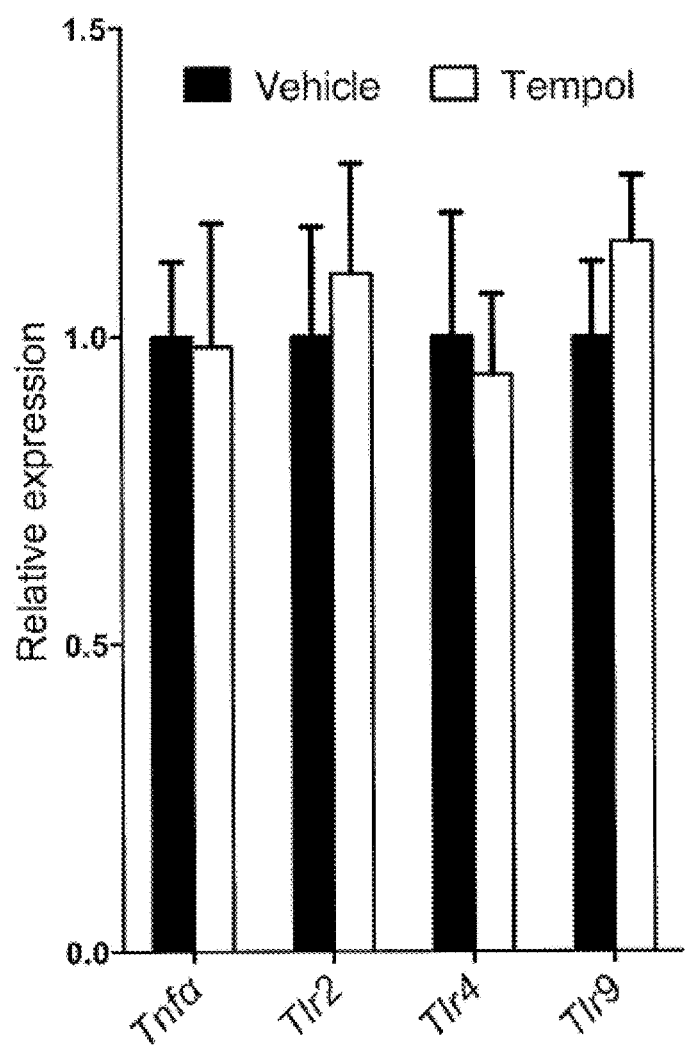

FIG. 32J shows mRNA levels of inflammation related genes in the livers of vehicle- and tempol-treated mice fed a high-fat diet for 7 weeks (n=3).

Figure 33A:
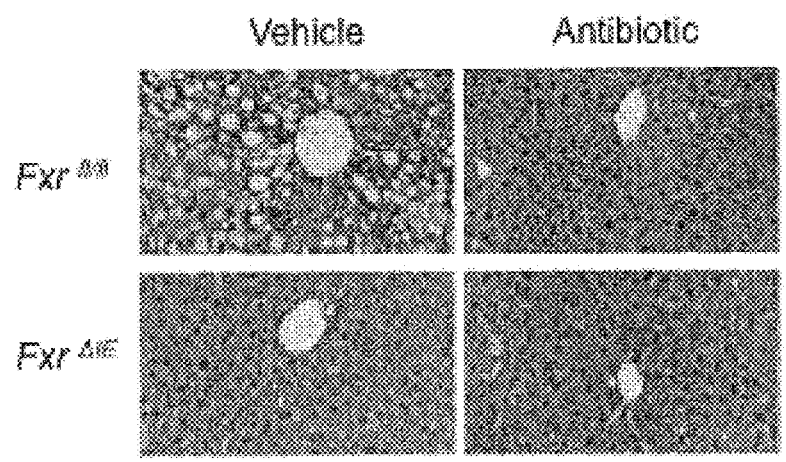

FIG. 33A shows a representative H&E staining of liver sections from vehicle- and antibiotic-treated $Fxr^{fl/fl}$ and $Fxr^{\Delta IE}$ mice fed a high-fat diet for 14 weeks.

Figure 33B:
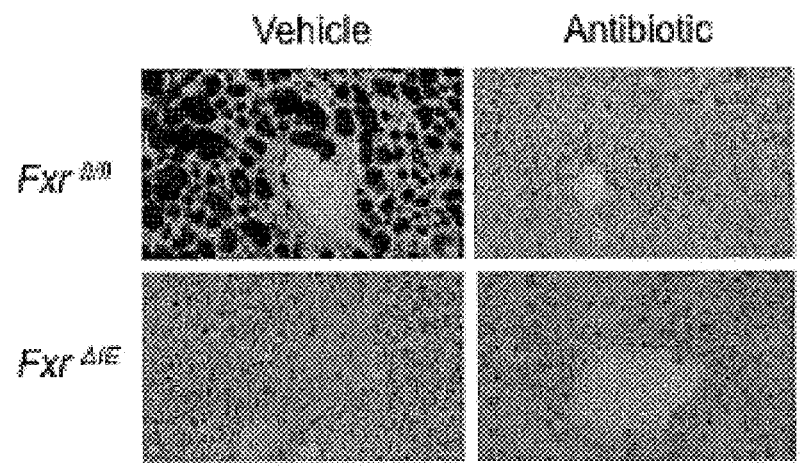

FIG. 33B shows Oil red 0 staining of lipid droplets in liver sections from vehicle- and antibiotic-treated $Fxr^{fl/fl}$ and $Fxr^{\Delta IE}$ mice fed a high-fat diet for 14 weeks.

Figure 33C:
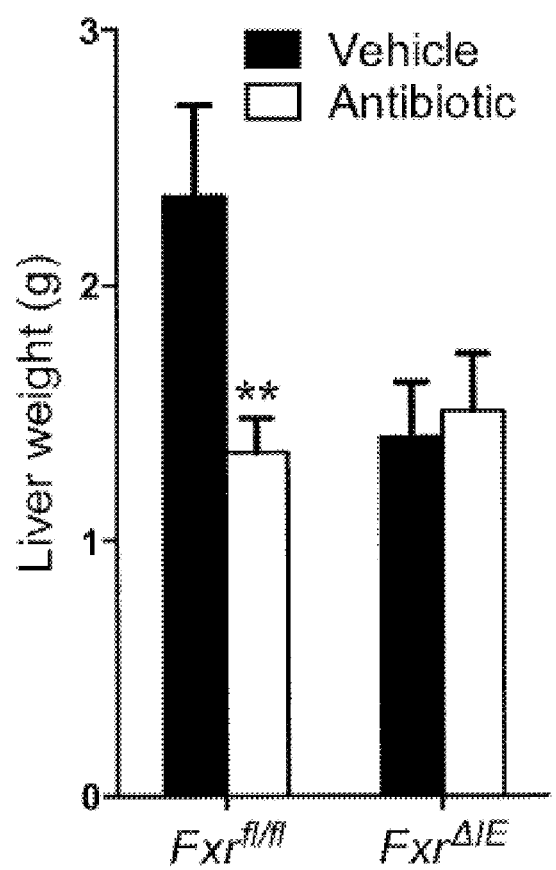

FIG. 33C shows liver weights of vehicle- and antibiotic-treated $Fxr^{fl/fl}$ and $Fxr^{\Delta IE}$ mice fed a high-fat diet for 14 weeks.

Figure 33D:
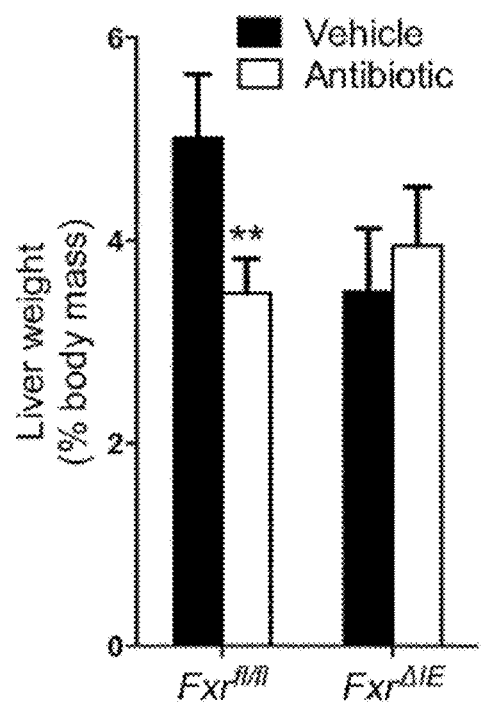

FIG. 33D shows liver weight to body weight ratios of vehicle- and antibiotic-treated $Fxr^{fl/fl}$ and $Fxr^{\Delta IE}$ mice fed a high-fat diet for 14 weeks.

Figure 33E:
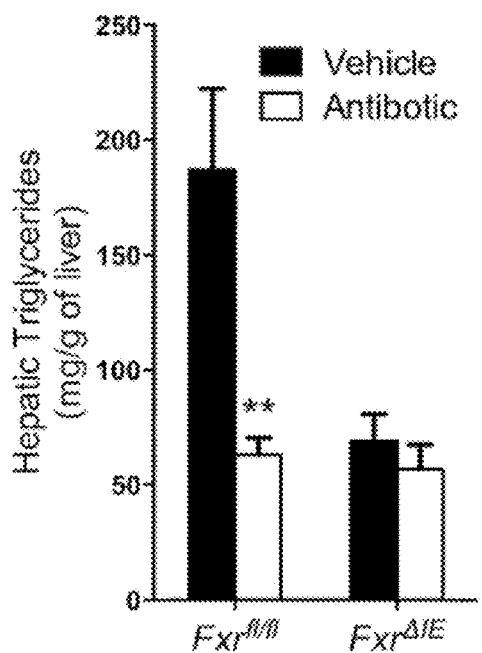

FIG. 33E shows liver triglyceride contents of vehicle and antibiotic-treated $Fxr^{fl/fl}$ and $Fxr^{\Delta IE}$ mice fed a high-fat diet for 14 weeks.

Figure 33F:
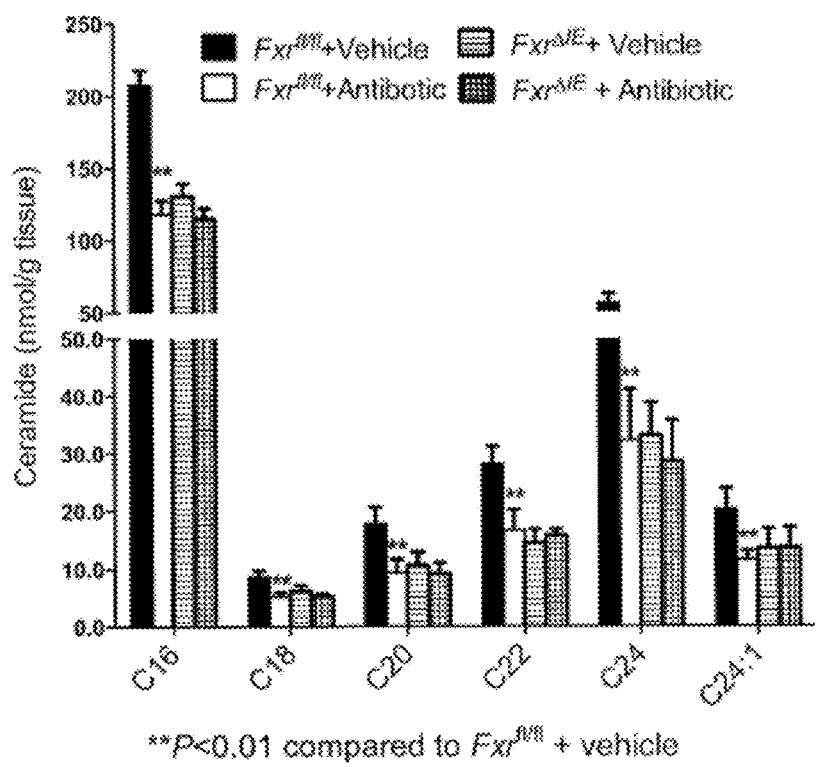

FIG. 33F shows lipidomics profile of ceramides in ileum of vehicle- and antibiotic-treated $Fxr^{fl/fl}$ and $Fxr^{\Delta IE}$ mice fed a high-fat diet for 14 weeks (bars from left to right for each ceramide, respectively).

Figure 33G:
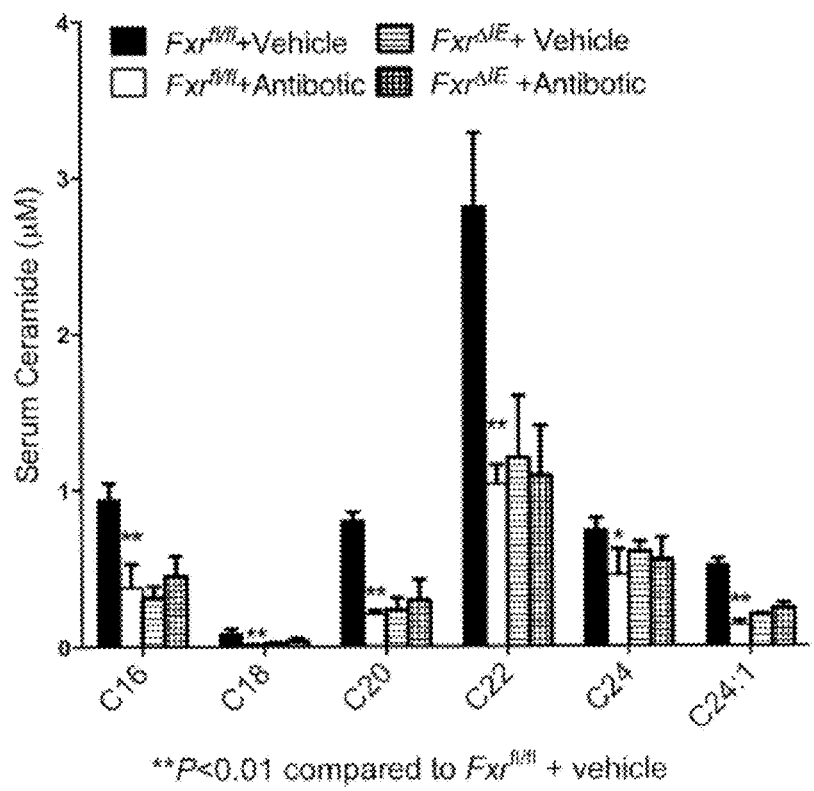

FIG. 33G shows serum ceramides levels from vehicle- and antibiotic-treated $Fxr^{fl/fl}$ and $Fxr^{\Delta IE}$ mice fed a high-fat diet for 14 weeks (bars from left to right for each ceramide, respectively).

Figure 34A:
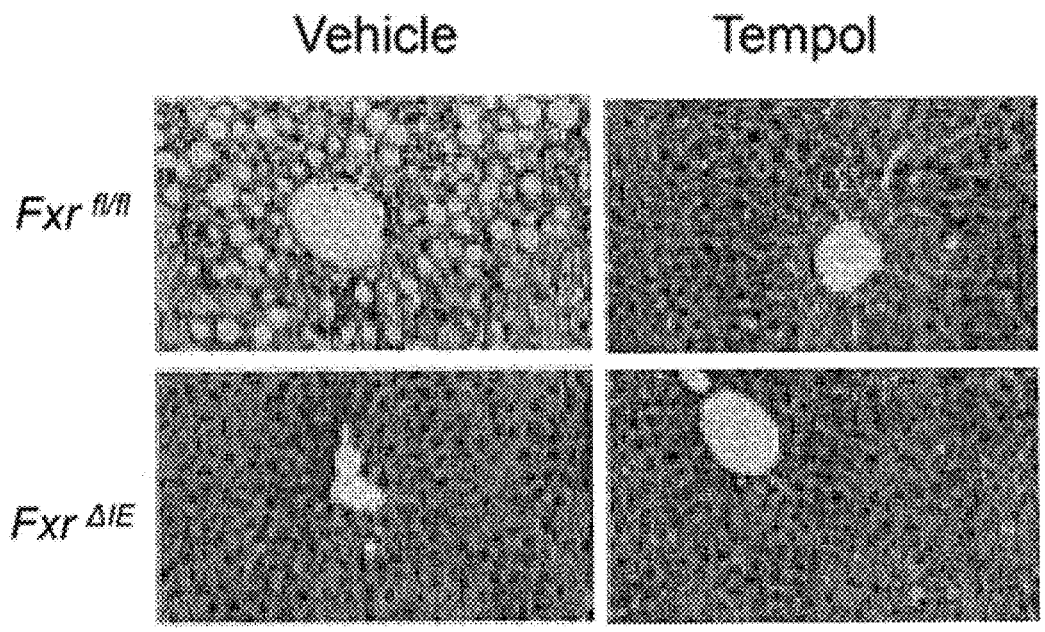

FIG. 34A shows representative H&E staining of liver sections from vehicle- and tempol-treated $Fxr^{fl/fl}$ and $Fxr^{\Delta IE}$ mice fed a high-fat diet for 14 weeks.

Figure 34B:
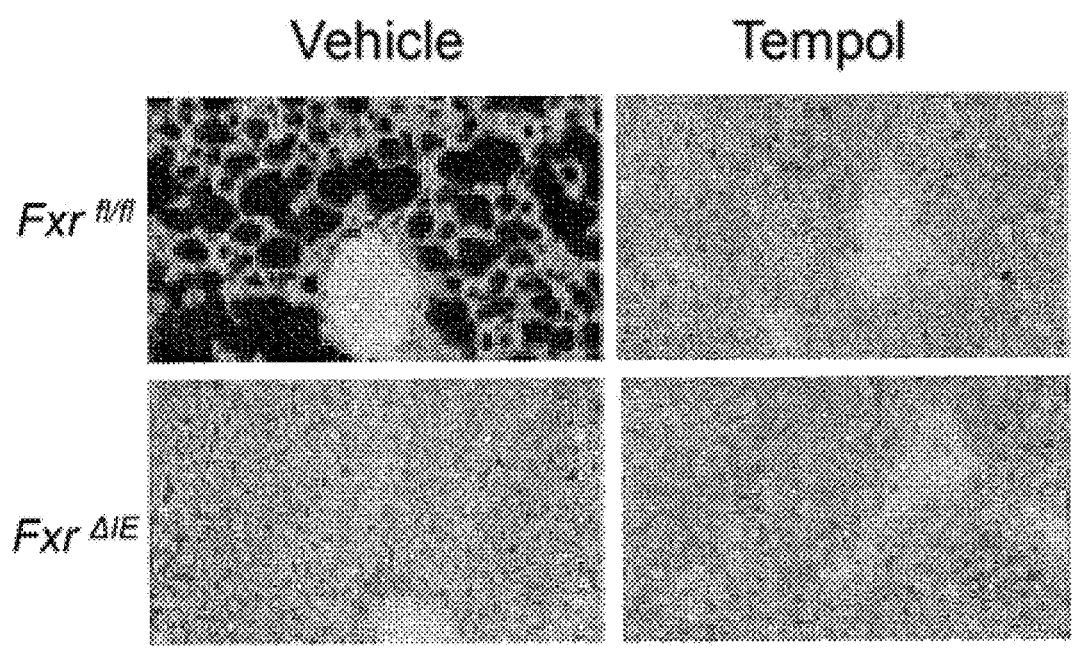

FIG. 34B shows Oil red 0 staining of lipid droplets in liver sections from vehicle and tempol-treated $Fxr^{fl/fl}$ mice and $Fxr^{\Delta IE}$ mice on a high-fat diet for 14 weeks.

Figure 34C:
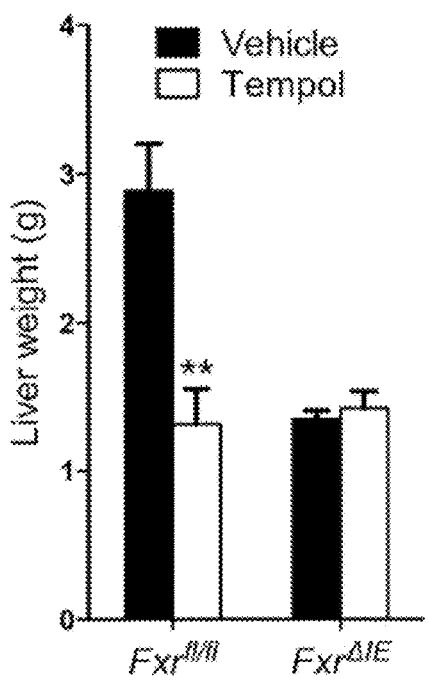

FIG. 34C shows liver weights-of vehicle and tempol-treated $Fxr^{fl/fl}$ mice and $Fxr^{\Delta IE}$ mice on a high-fat diet for 14 weeks.

Figure 34D:
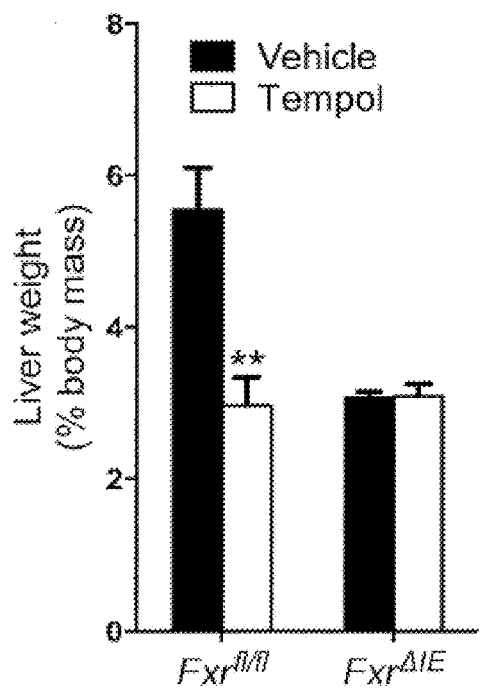

FIG. 34D shows liver weight to body weight ratios from vehicle- and tempol-treated $Fxr^{fl/fl}$ mice and $Fxr^{\Delta IE}$ mice on a high-fat diet for 14 weeks.

Figure 34E:
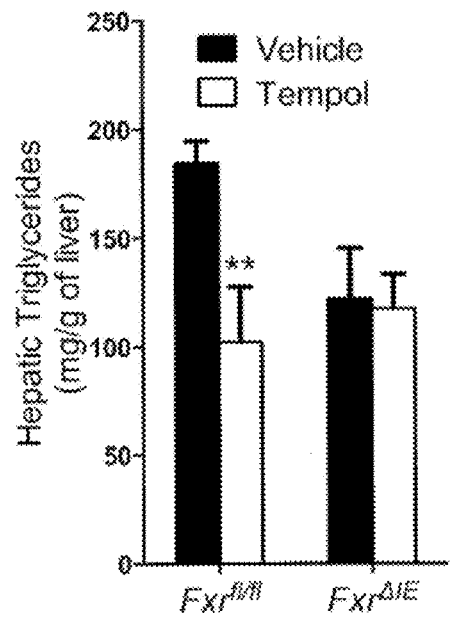

FIG. 34E shows liver triglyceride levels from vehicle- and tempol-treated $Fxr^{fl/fl}$ mice and $Fxr^{\Delta IE}$ mice on a high-fat diet for 14 weeks.

Figure 34F:
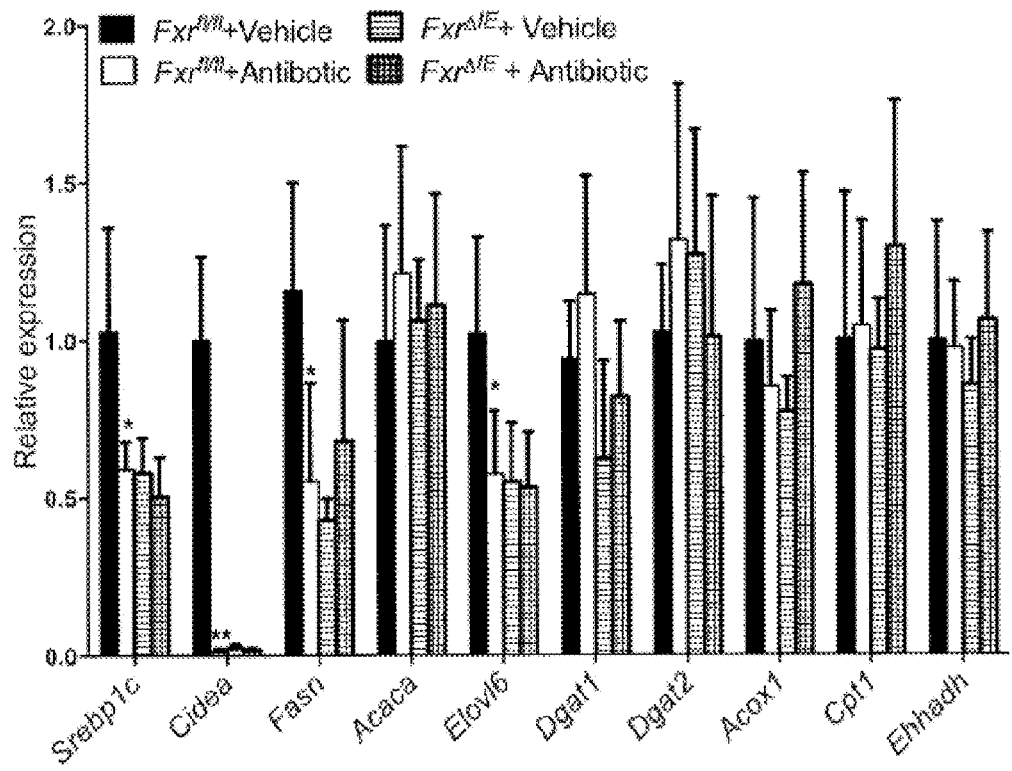

FIG. 34F shows mRNA levels of fatty acid synthesis, triglyceride synthesis, and fatty acid catabolism related genes in livers from vehicle and tempol-treated $Fxr^{fl/fl}$ mice and $Fxr^{\Delta IE}$ mice on a high-fat diet for 14 weeks. The bars under each mRNA from left to right are vehicle-treated $Fxr^{fl/fl}$, tempol-treated $Fxr^{fl/fl}$, vehicle-treated $Fxr^{\Delta IE}$ tempol-treated $Fxr^{\Delta IE}$ mice.

Figure 34G:
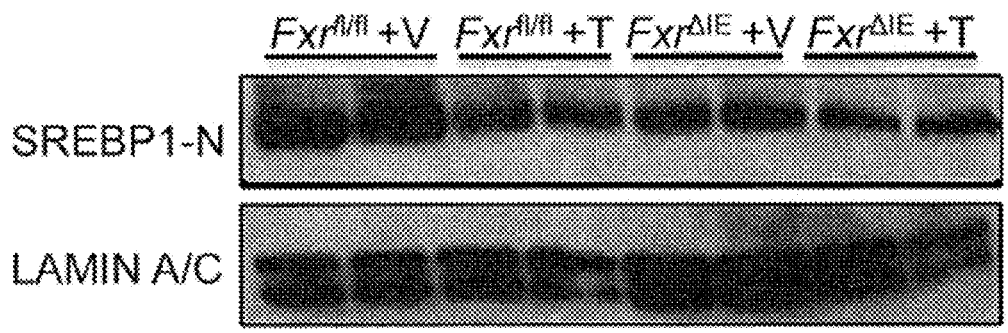

FIG. 34G shows western blot analysis of liver nuclear SREBP1-N expression after tempol treatment of $Fxr^{fl/fl}$ and $Fxr^{\Delta IE}$, mice on a high-fat diet for 16 weeks. Each lane represents an individual mouse.

Figure 34H:
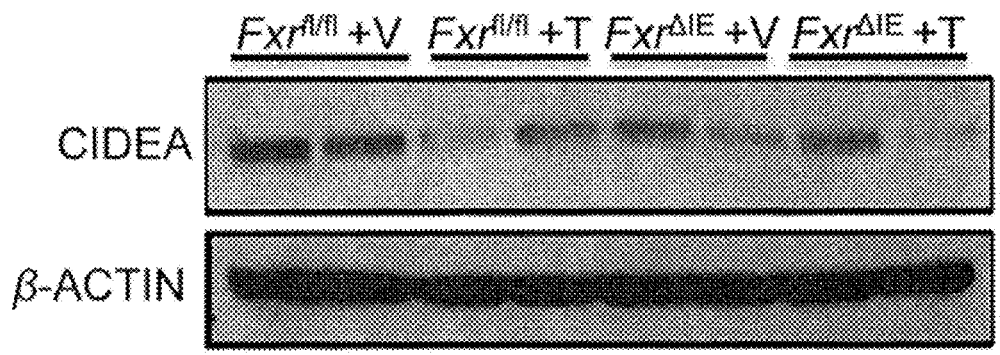

FIG. 34H shows western blot analysis of liver CIDEA expression after tempol treatment of $Fxr^{fl/fl}$ and $Fxr^{\Delta IE}$, mice on a high-fat diet for 16 weeks. Each lane represents an individual mouse.

Figure 35:
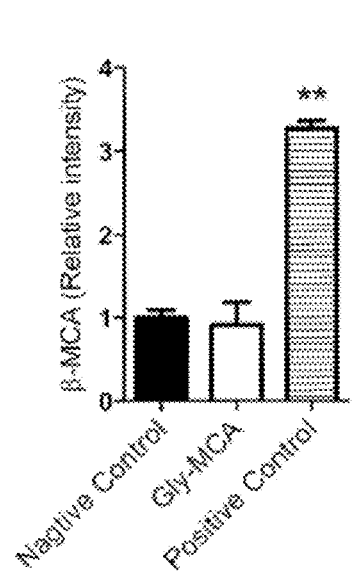

FIG. 35 shows the metabolism of the positive control tauro-β-muricholic acid (TβMCA) and glycine-β-muricholic acid (Gly-MCA) to the product β-muricholic acid (TβMCA) after incubation with fecal protein containing intestinal bacteria.

Figure 36:
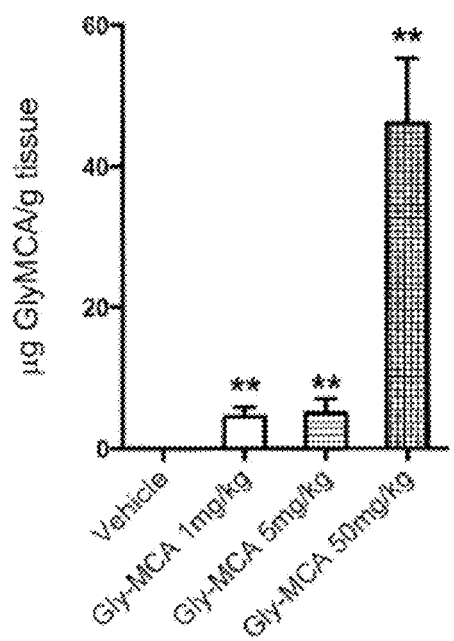

FIG. 36 shows concentrations of Gly-MCA in mouse ileum after oral gavage of 0, 1, 5, and 50 mg/kg of Gly-MCA.

Figure 37A:
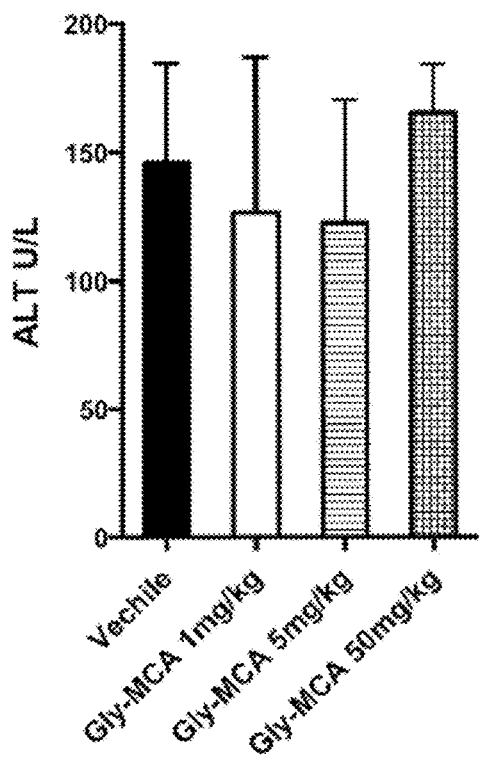

FIG. 37A shows serum aminotransferase (ALT) levels in mice after 24 hours of treatment with Gly-MCA.

Figure 37B:
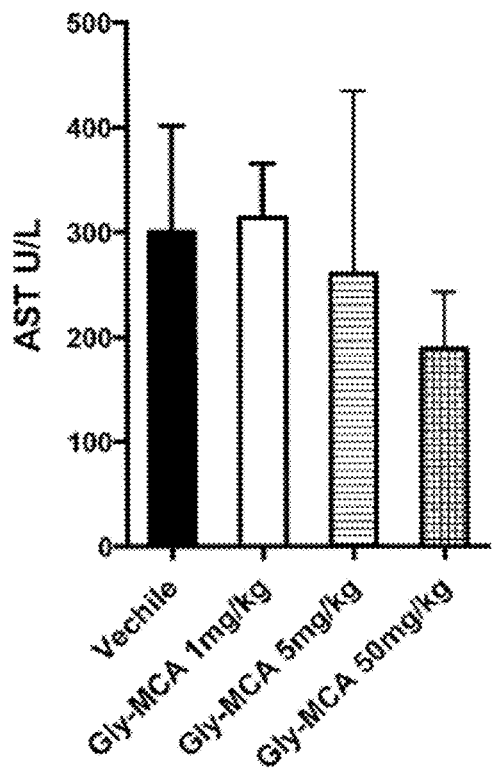

FIG. 37B shows aspartate aminotransferase (ALT) levels in mice after 24 hours of treatment with Gly-MCA.

Figure 38:
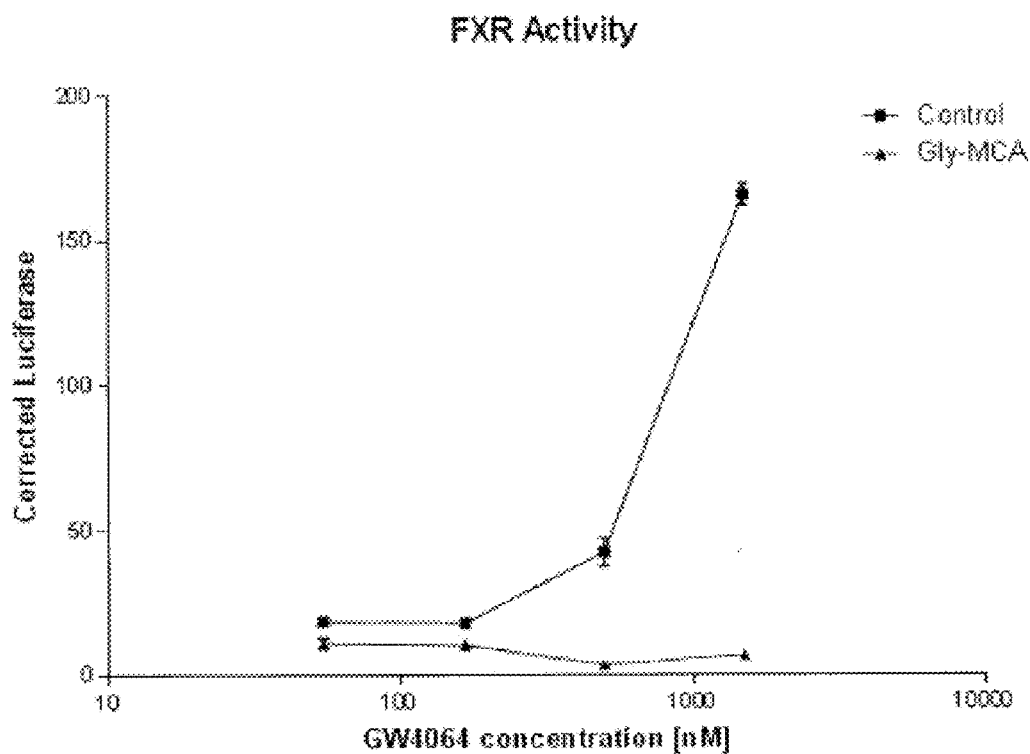

FIG. 38 shows luciferase activity observed in HEK293T fibroblasts transiently co-transfected with a chimeric receptor construct as a function of concentration of the added FXR agonist GW4064 in the presence and absence of Gly-MCA.

Figure 39:
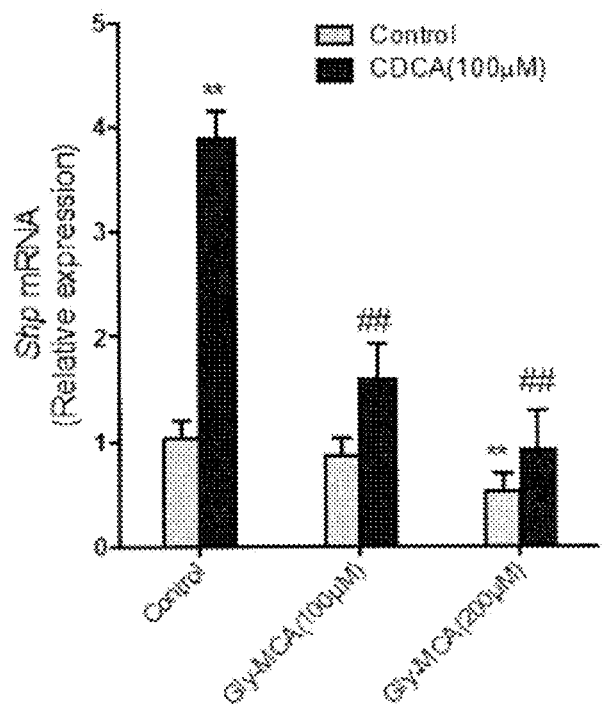

FIG. 39 shows Shp mRNA expression in differentiated Caco-2 cells treated with 100 μM CDCA and vehicle (control), or 100 μM and 200 μM Gly-MCA with 100 μM CDCA (n=3).

Figure 40A:
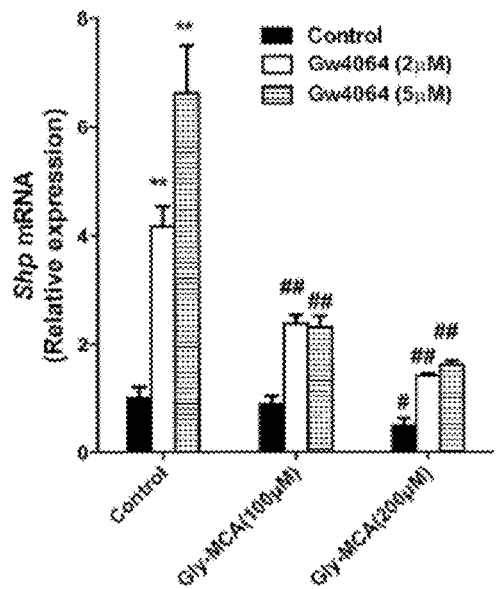

FIG. 40A shows levels of Shp mRNA in differentiated Caco-2 cells after treatment with 100 μM and 200 μM Gly-MCA and with 2 μM GW4064 or 5 μM GW4064 (n=3). For each dosage of Gly-MCA from left to right is shown further treatment with no GW4064, 2 μM GW4064, and 5 μM GW4064.

Figure 40B:
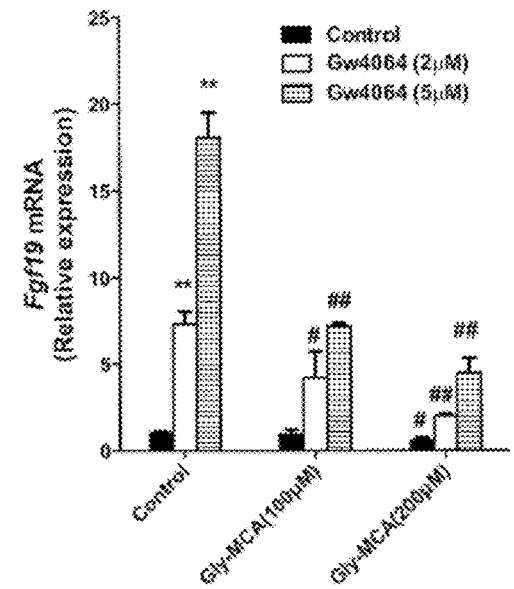

FIG. 40B shows levels of Fgf19 mRNA in differentiated Caco-2 cells after treatment with 100 μM and 200 μM Gly-MCA and with 2 μM GW4064 or 5 μM GW4064 (n=3). For each dosage of Gly-MCA from left to right is shown further treatment with no GW4064, 2 μM GW4064, and 5 μM GW4064.

Figure 40C:
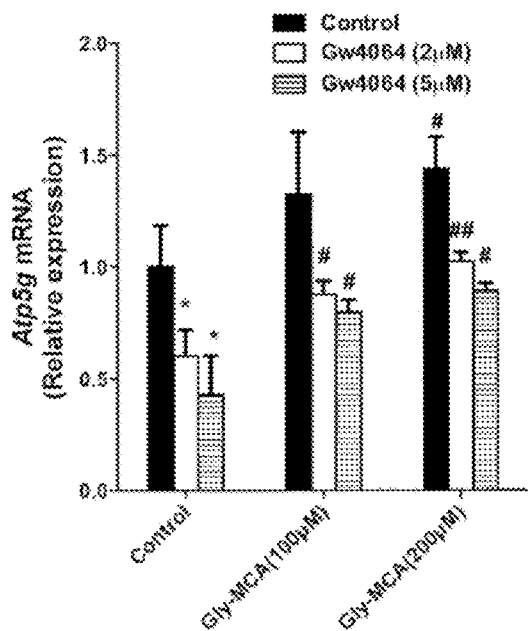

FIG. 40C shows levels of Atp5g mRNAs in differentiated Caco-2 cells after treatment with 100 μM and 200 μM Gly-MCA and with 2 μM or 5 μM GW4064 (n=3). For each dosage of Gly-MCA from left to right is shown treatment with no GW4064, 2 μM GW4064, and 5 μM GW4064.

Figure 41A:
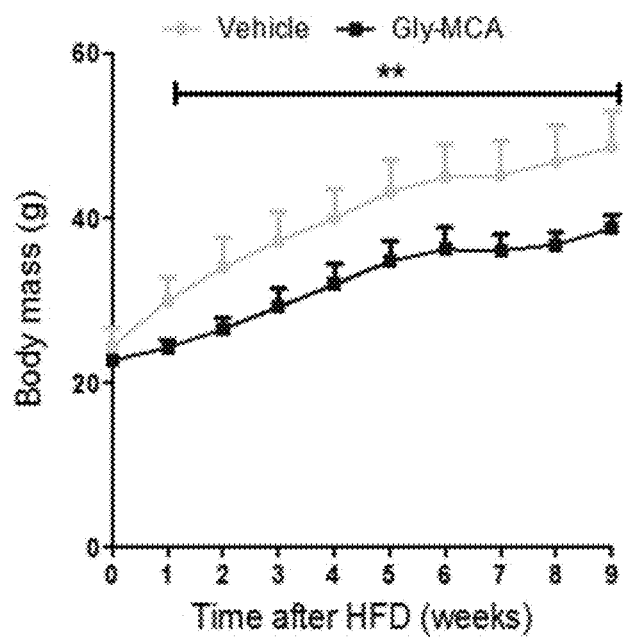
Figure 41B:
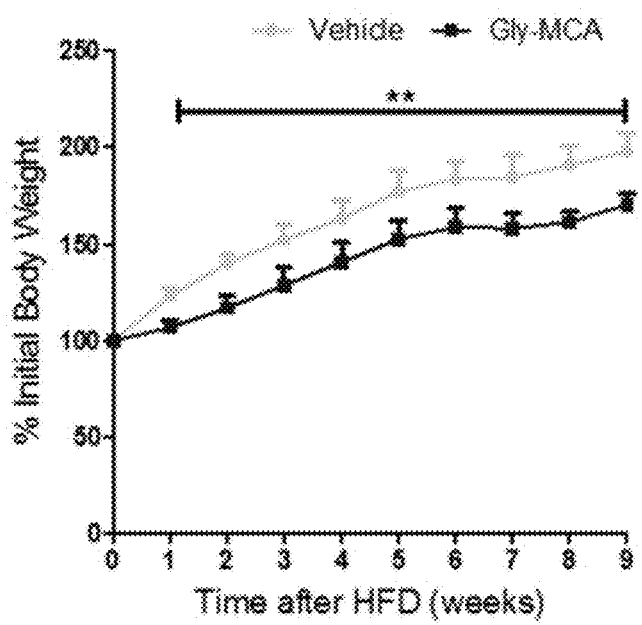

FIGS. 41A and 41B show growth curves of changes in body mass (A) and % changes in initial body weight (B), over the course of 9 weeks, of vehicle- and Gly-MCA-treated mice, respectively, fed a high-fat diet. n=5 mice per group.

Figure 41C:
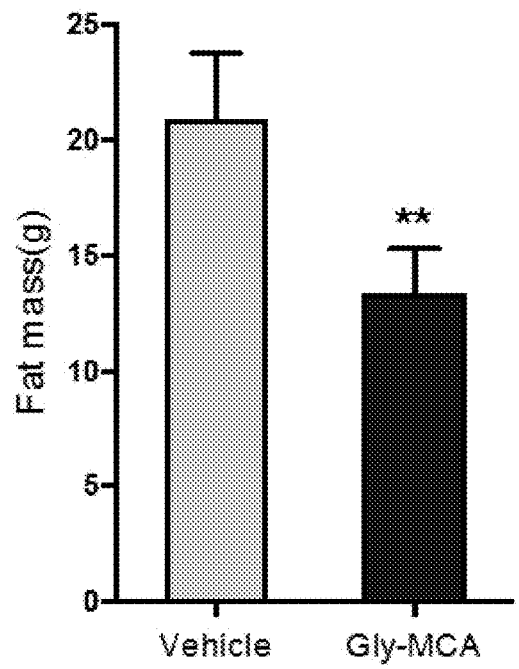
Figure 41D:
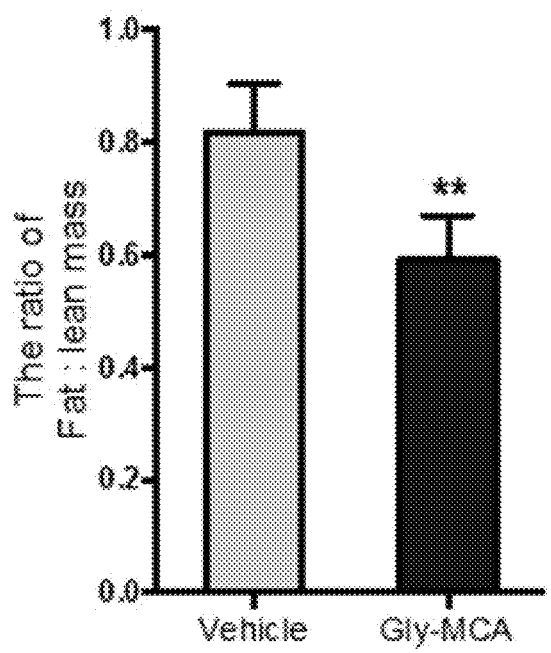

FIGS. 41C and 41D show body composition as determined by NMR to show the fat mass (C) and fat mass to lean mass ratio (D) in vehicle and Gly-MCA-treated mice, respectively, after 9 weeks on a high-fat diet. n=5 mice per group.

Figure 42A:
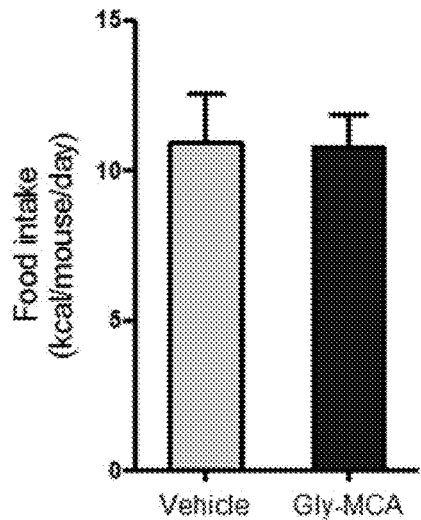

FIG. 42A shows cumulative food intake per day averaged over a period of 1 week (from 6 to 7 weeks) in vehicle- and Gly-MCA-treated mice fed a high-fat diet.

Figure 42B:
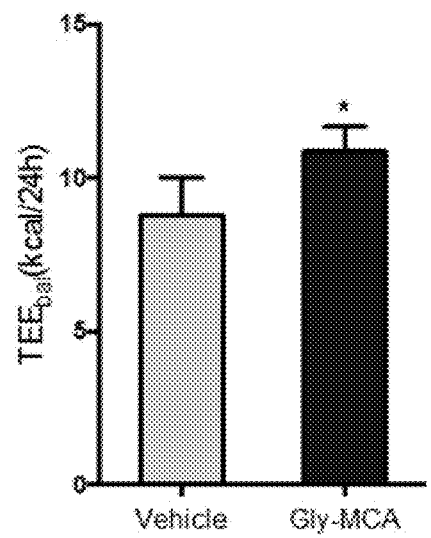

FIG. 42B shows 24 h energy expenditure using an indirect energy balance ($TEE_{bal}$) for an average period of 1 week (from 6 to 7 weeks) in vehicle- and Gly-MCA-treated mice fed a high-fat diet. n=5 mice per group.

Figure 43A:
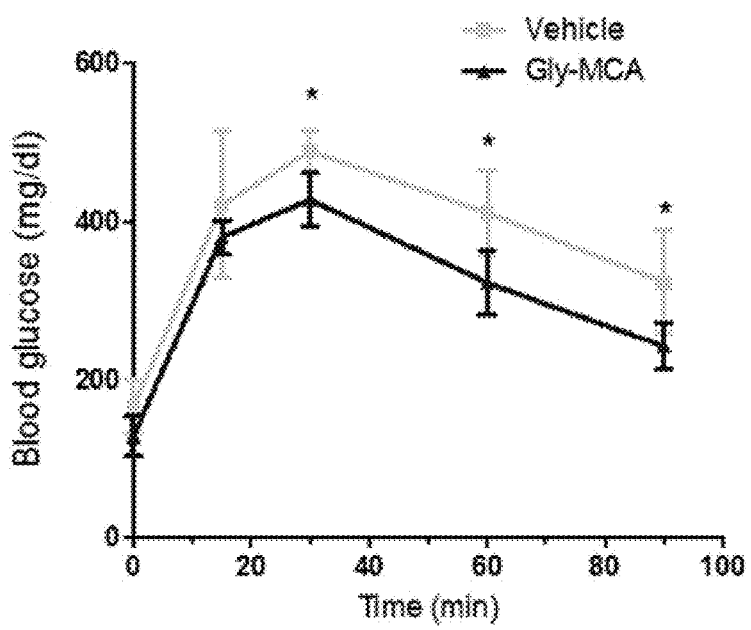

FIG. 43A shows the glucose tolerance test (GTT) in vehicle- and Gly-MCA-treated mice after 6 to 7 weeks of feeding a high-fat diet. n=5 mice per group.

Figure 43B:
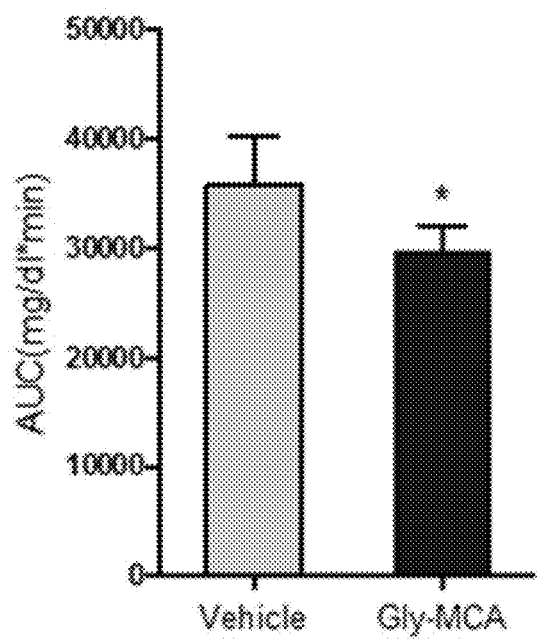
Figure 45A:
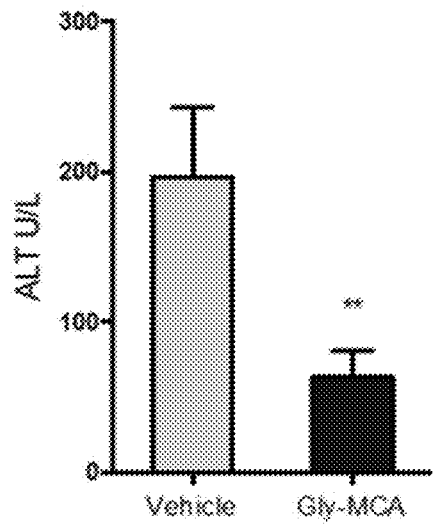

FIG. 43B shows the area under the curve (AUC) of the glucose tolerance test depicted in FIG. 45A.

Figure 43C:
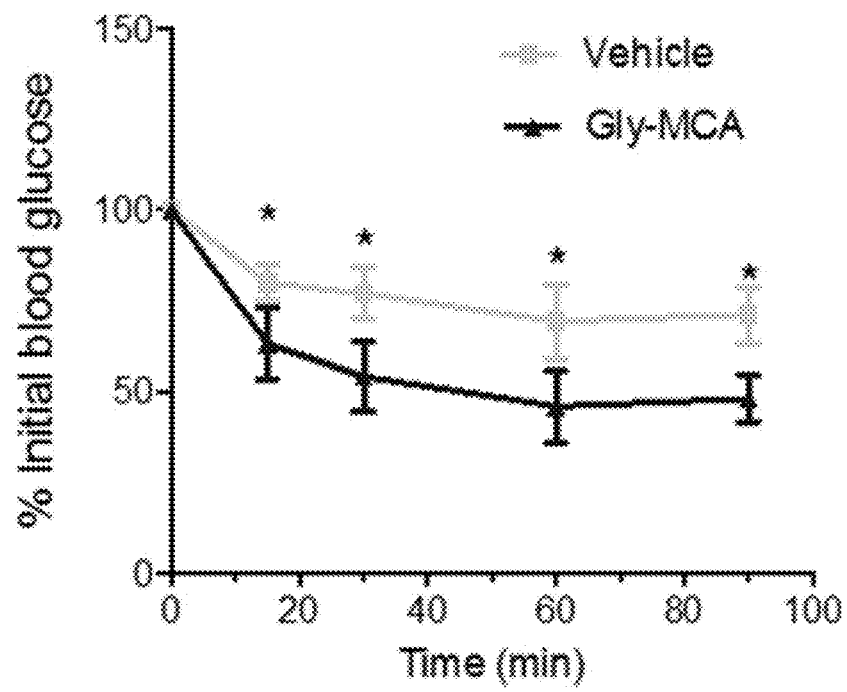

FIG. 43C shows the insulin tolerance test (ITT) in vehicle- and Gly-MCA-treated mice after 6 to 7 weeks of feeding a high-fat diet. n=5 mice per group.

Figure 44A:
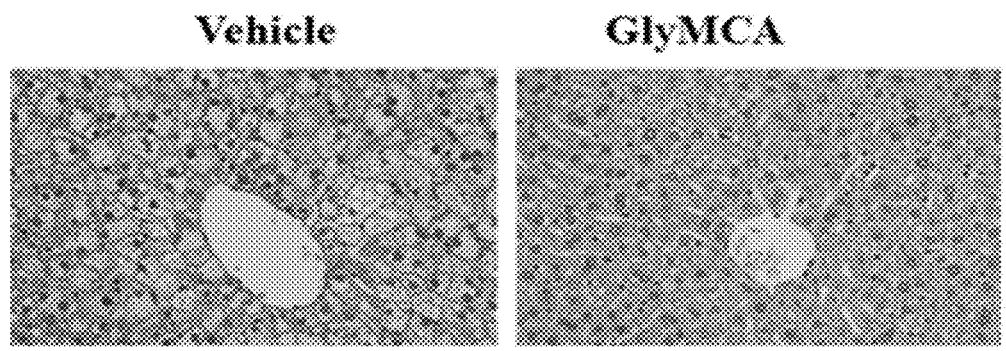

FIG. 44A shows representative H&E staining of liver sections in vehicle- and Gly-MCA-treated mice fed a high-fat diet for 7 weeks.

Figure 44B:
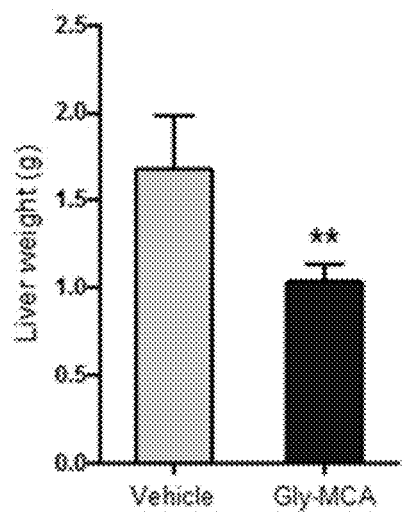

FIG. 44B shows liver weights in vehicle- and Gly-MCA-treated mice fed a high-fat diet for 7 weeks. n=5 mice per group.

Figure 44C:
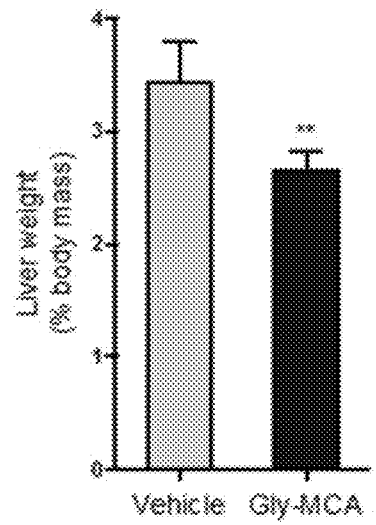

FIG. 44C shows liver weight to body weight ratios in vehicle- and Gly-MCA-treated mice fed a high-fat diet for 7 weeks. n=5 mice per group.

Figure 44D:
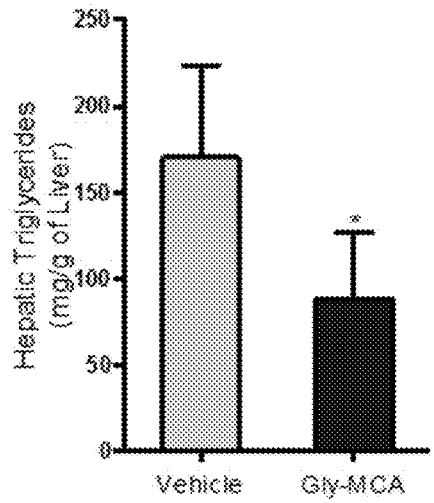

FIG. 44D shows liver triglyceride content of vehicle- and Gly-MCA-treated mice fed a high-fat diet for 9 weeks. n=5 mice per group.

Figure 45B:
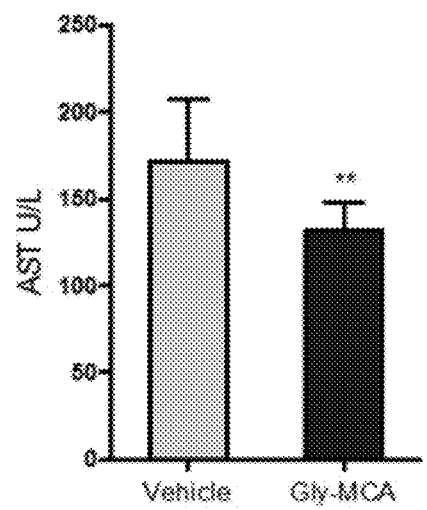

FIGS. 45A and 45B show serum alanine aminotransferase (ALT) and aspartate aminotransferase (AST) levels of vehicle- and Gly-MCA-treated mice, respectively, fed a high-fat diet for 9 weeks. n=5 mice per group.

Figure 46A:
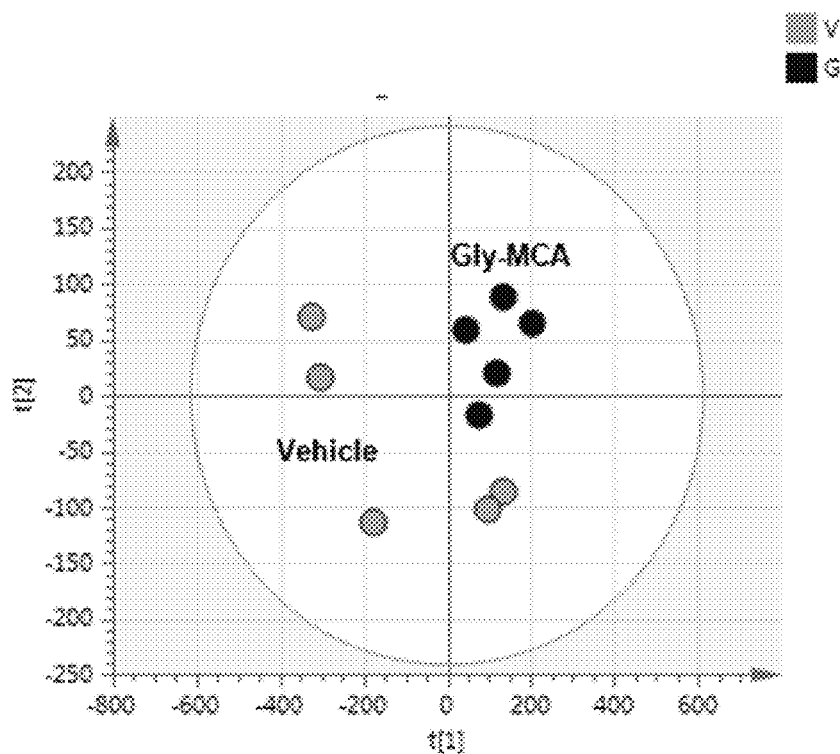

FIG. 46A shows a scores scatter plot of a PCA model of feces ions from vehicle- and Gly-MCA-treated mice fed a high-fat diet for 9 weeks.

Figure 46B:
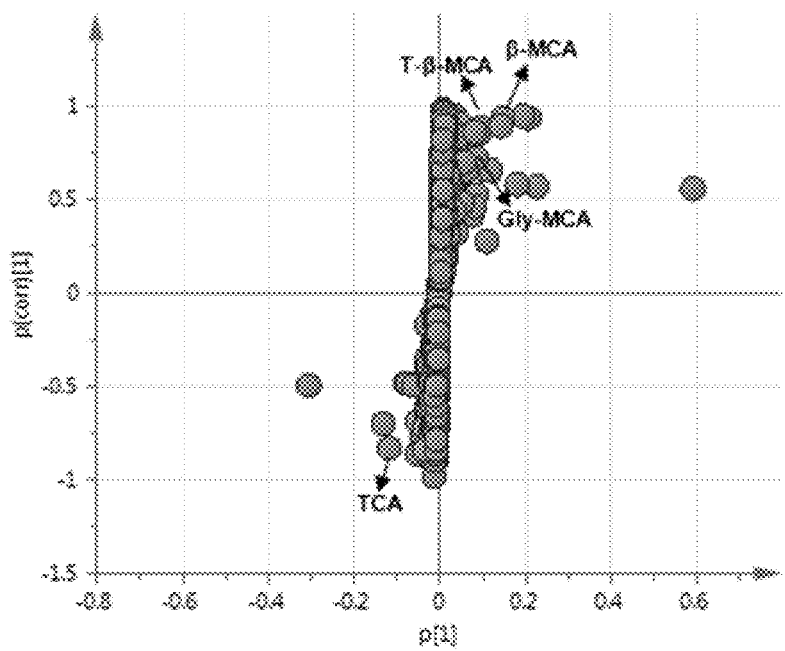

FIG. 46B shows a scatter plot of partial least squares discriminant analysis (PLS-DA) of feces ions from vehicle and Gly-MCA-treated mice fed a high-fat diet for 9 weeks. Each point represents an individual mouse feces ion. The labeled ions are identified as β-MCA, TβMCA, taurocholic acid (TCA) and Gly-MCA, which are affected by Gly-MCA treatment. The p(corr)[1]P values represent the interclass difference and p[1]P values represent the relative abundance of the ions. Data were obtained in negative ionization mode (ESI−).

Figure 46C:
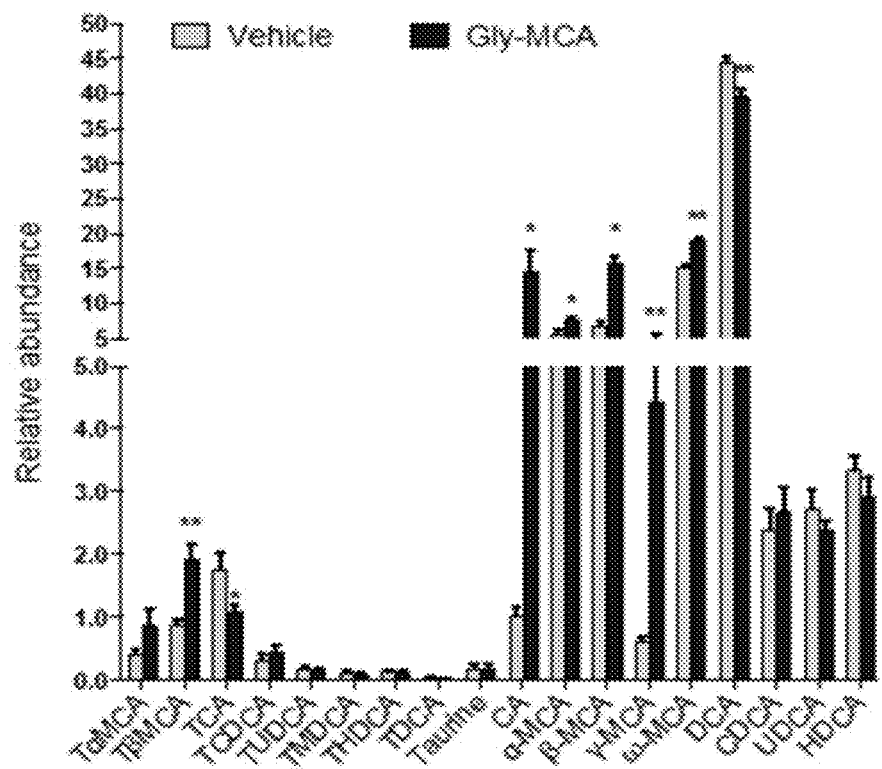

FIG. 46C shows individual bile acid compositions in feces ions from vehicle- and Gly-MCA-treated mice fed a high-fat diet for 9 weeks.

Figure 46D:
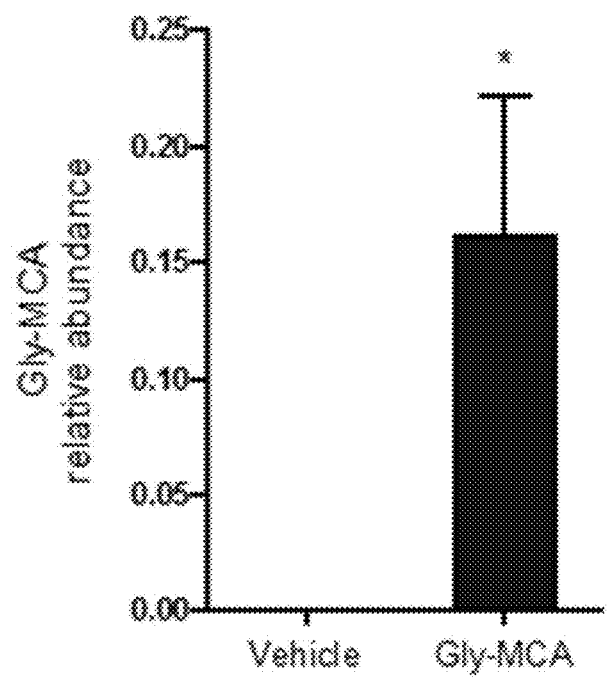

FIG. 46D shows Gly-MCA levels in feces of vehicle- and Gly-MCA-treated mice fed a high-fat diet for 9 weeks. n=5 mice per group. All data are presented as mean±SD.

Figure 47A:
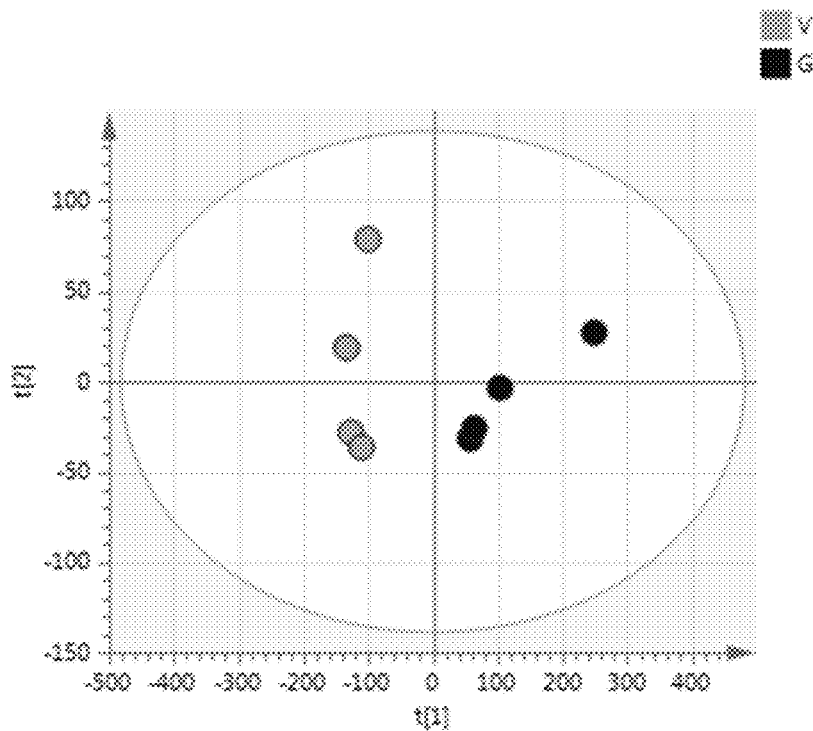

FIG. 47A shows a scores scatter plot of a PCA model of ileum ions in vehicle- and Gly-MCA-treated mice fed a high-fat diet for 9 weeks.

Figure 47B:
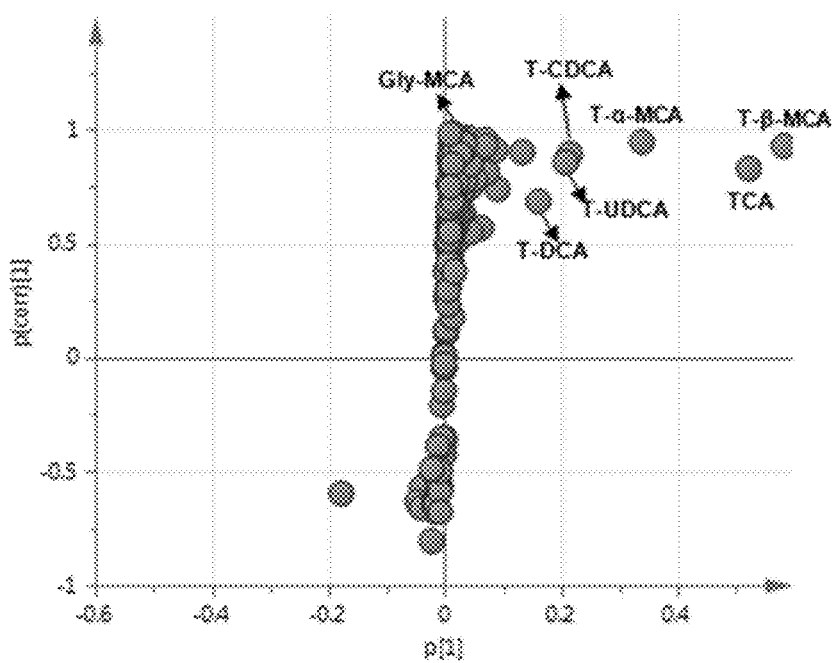

FIG. 47B shows a scatter plot of PLS-DA of ileum ions from vehicle and Gly-MCA-treated mice fed a high-fat diet for 9 weeks. Each point represents an individual mouse feces ion. The labeled ions are identified as T-α-MCA, TβMCA, taurocholic acid (TCA), tauroursodeoxycholic acid (TCDCA), taurodeoxycholic acid (TDCA) and taurochenodeoxycholic acid (TCDCA) and Gly-MCA, which are induced by Gly-MCA treatment. The p(corr)[1]P values represent the interclass difference and p[1]P values represent the relative abundance of the ions. All the data are obtained in negative mode (ESI−).

Figure 47C:
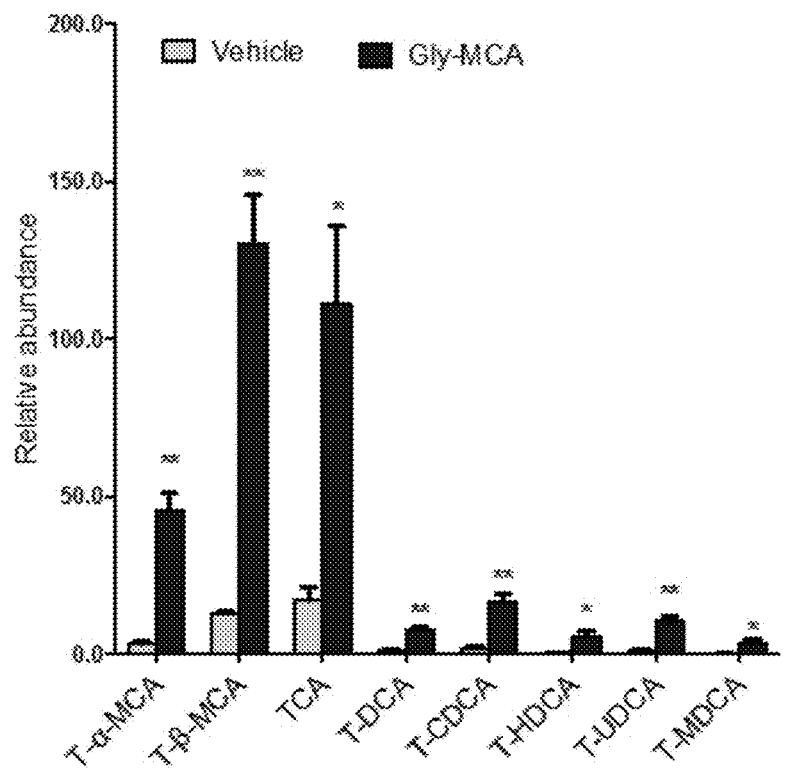

FIG. 47C shows the bile acid composition in ileum from vehicle and Gly-MCA-treated mice fed a high-fat diet for 9 weeks.

Figure 47D:
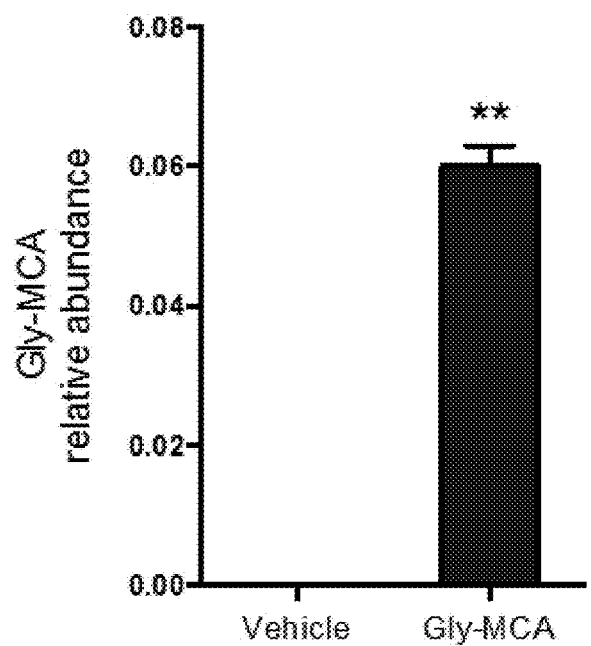

FIG. 47D shows Gly-MCA levels in ileum of vehicle- and Gly-MCA-treated mice fed a high-fat diet for 9 weeks. n=5 mice per group. All data are presented as mean±SD.

Figure 48A:
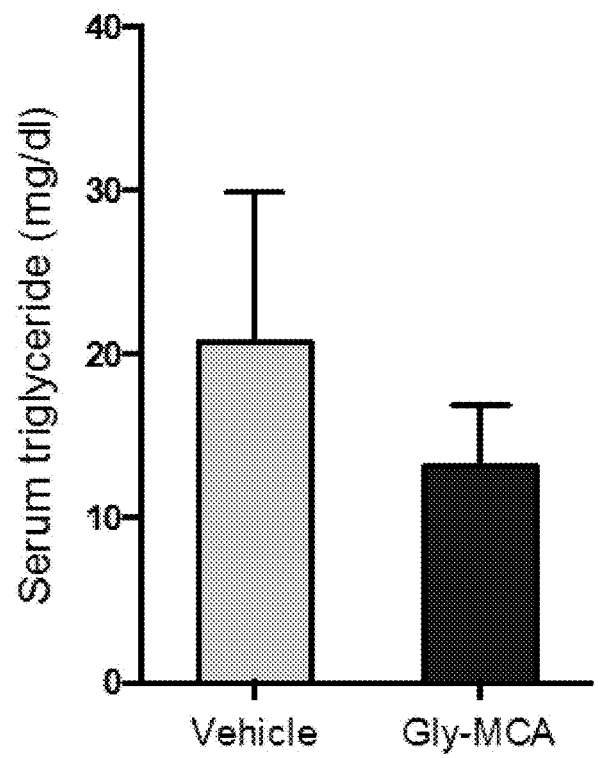

FIG. 48A shows serum total triglyceride levels of vehicle- and Gly-MCA-treated mice fed a high-fat diet for 9 weeks. n=5 mice per group.

Figure 48B:
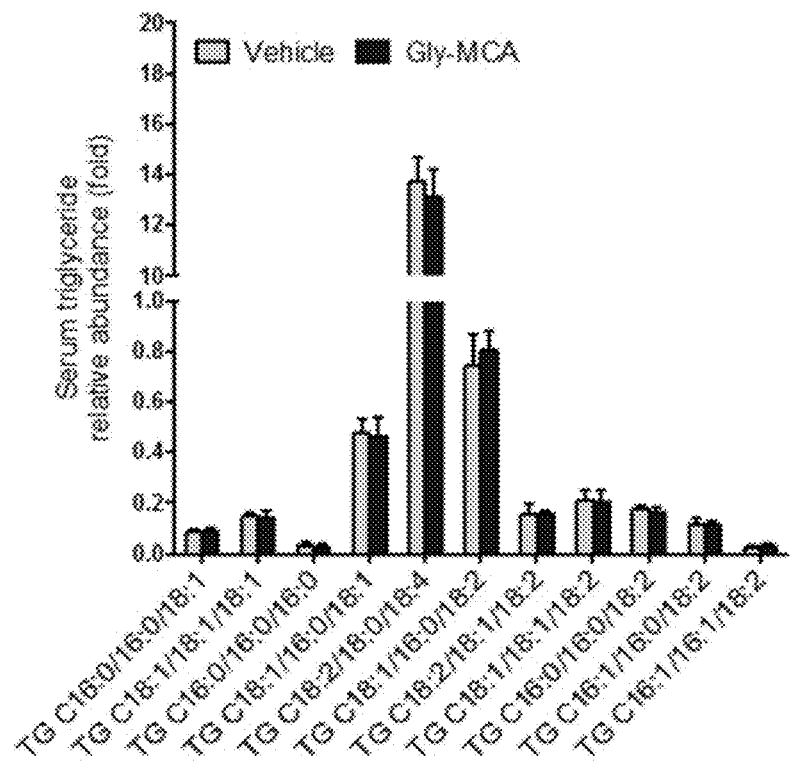

FIG. 48B shows the profile of serum triglyceride species from vehicle- and Gly-MCA-treated mice fed a high-fat diet for 9 weeks. n=5 mice per group. All data are presented as mean±SD.

Figure 49A:
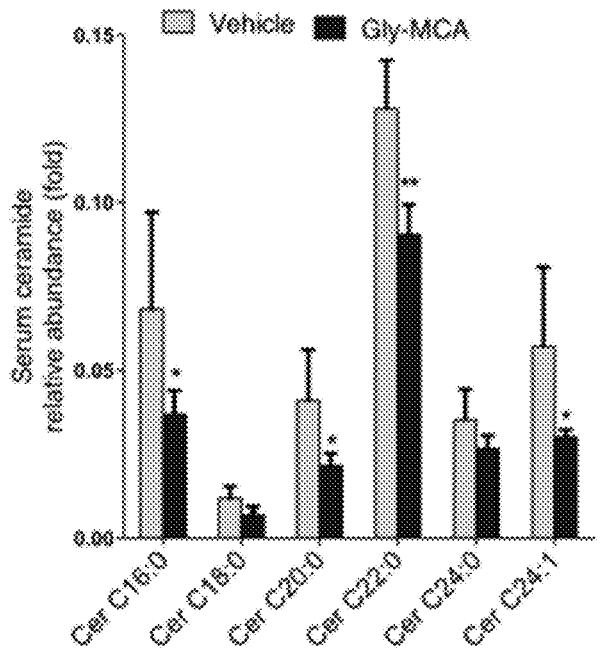

FIG. 49A shows profiles of serum ceramides from vehicle- and Gly-MCA-treated mice fed a high-fat diet for 9 weeks. n=5 mice per group.

Figure 49B:
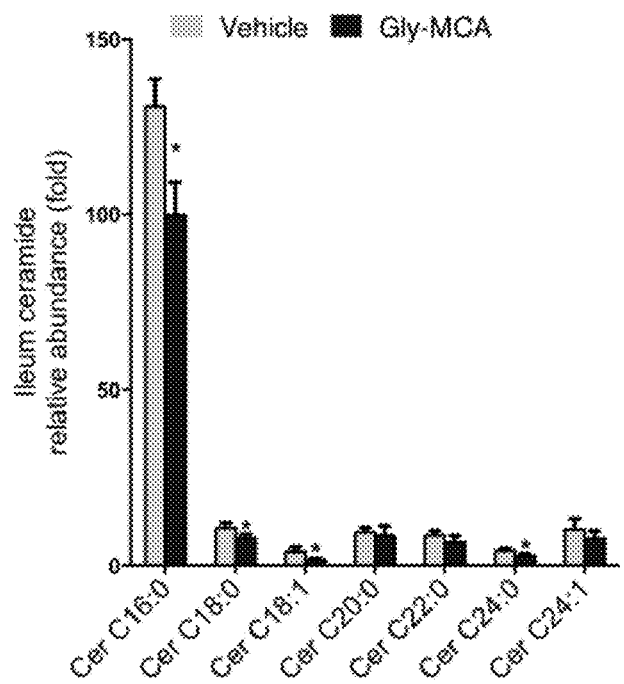

FIG. 49B shows profiles of ileum ceramides from vehicle- and Gly-MCA-treated mice fed a high-fat diet for 9 weeks. n=5 mice per group. All data are presented as mean±SD.

Figure 50A:
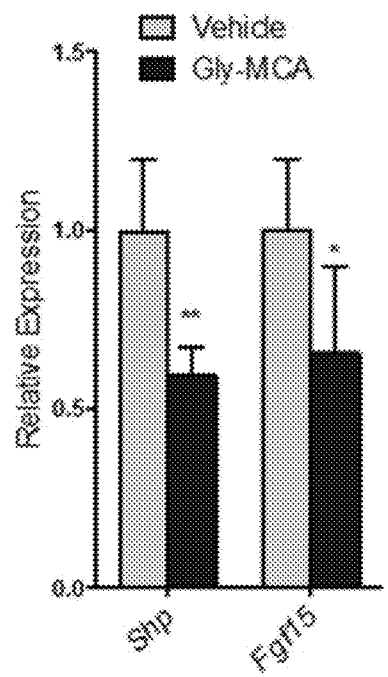

FIG. 50A shows mRNA levels of FXR target genes Shp and Fgf15 in the ileum of vehicle- and Gly-MCA-treated mice fed a high-fat diet for 9 weeks. n=5 mice per group.

Figure 50B:
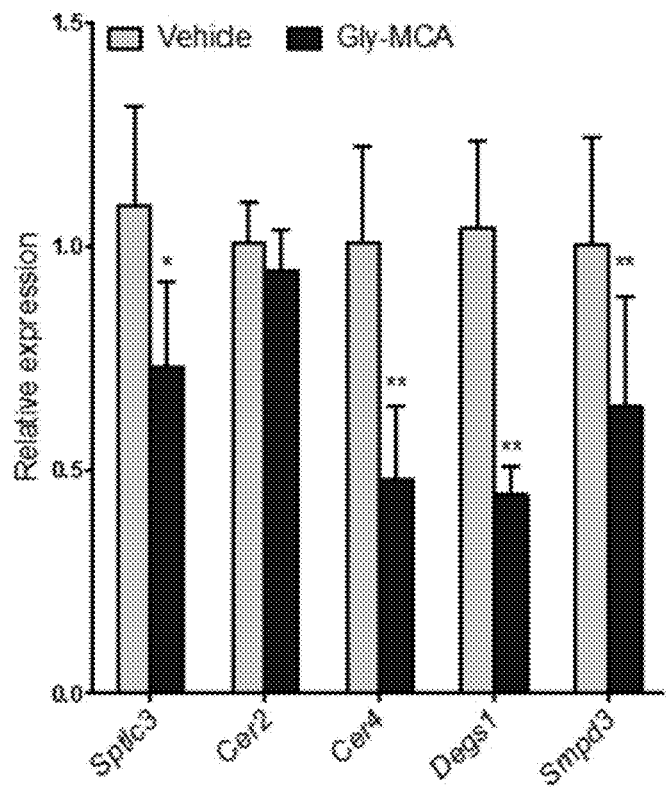

FIG. 50B shows levels of mRNAs encoding genes involved in ceramide metabolism in ileum from vehicle- and Gly-MCA-treated mice fed a high-fat diet for 9 weeks. n=5 mice per group. All data are presented as mean±SD.

Figure 51A:
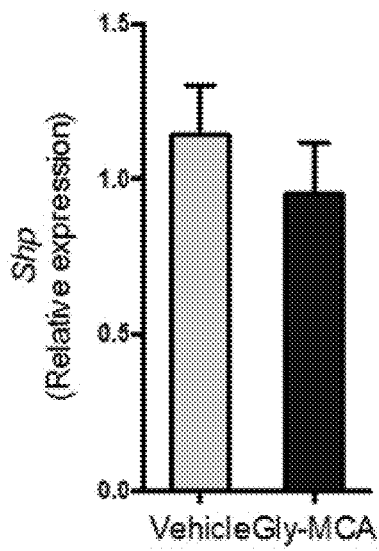

FIG. 51A shows mRNA levels of the FXR target gene Shp in the liver of vehicle- and Gly-MCA-treated mice fed a high-fat diet for 9 weeks. n=5 mice per group.

Figure 51B:
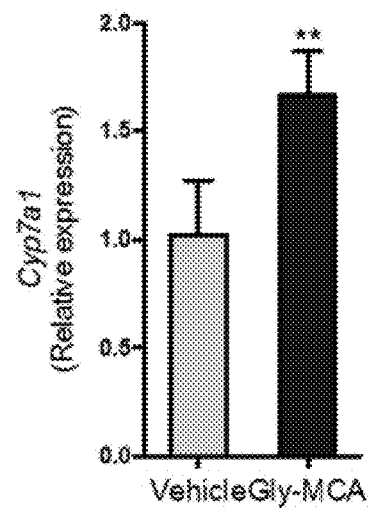

FIG. 51B shows mRNA levels of Cyp7a1 in the liver of vehicle- and Gly-MCA-treated mice fed a high-fat diet for 9 weeks. n=5 mice per group. All data are presented as mean±SD.

Figure 52:
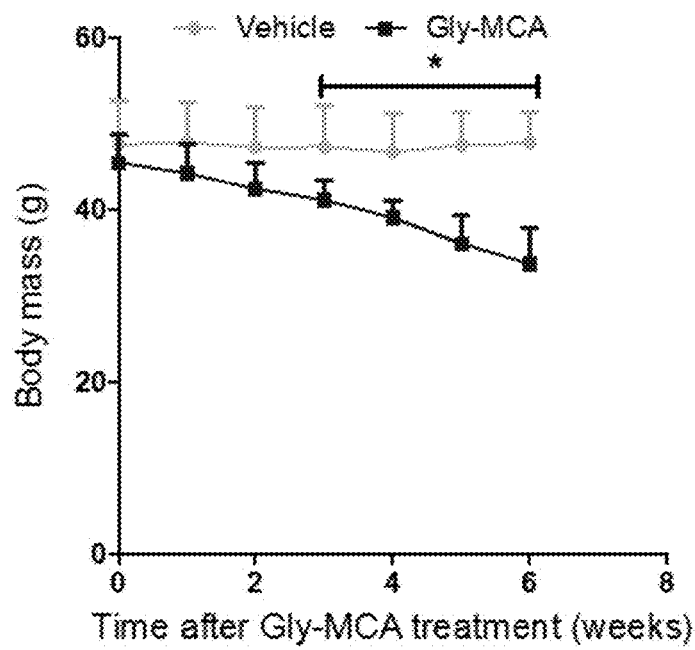

FIG. 52 shows growth curves of genetically obese leptin receptor-deficient (db/db) treated with vehicle and Gly-MCA for 6 weeks. n=5 mice per group. All data are presented as mean±SD.

Figure 53A:
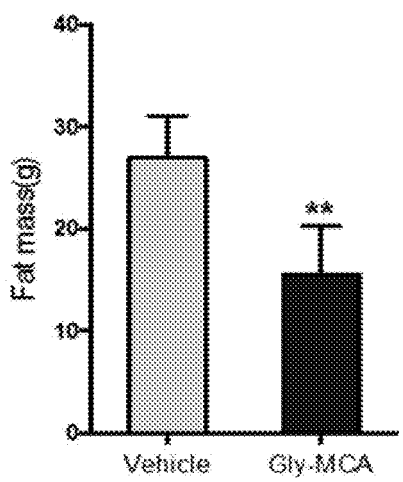
Figure 53B:
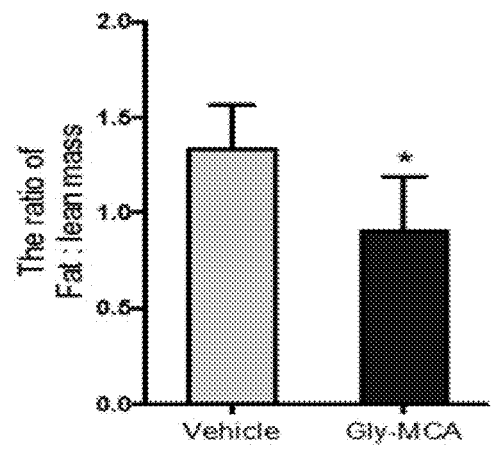

FIGS. 53A and 53B show the body composition, as determined by NMR, of the fat mass, and fat mass to lean mass ratio in db/db mice treated with vehicle and Gly-MCA for 6 weeks. n=5 mice per group. All data are presented as mean±SD.

Figure 54A:
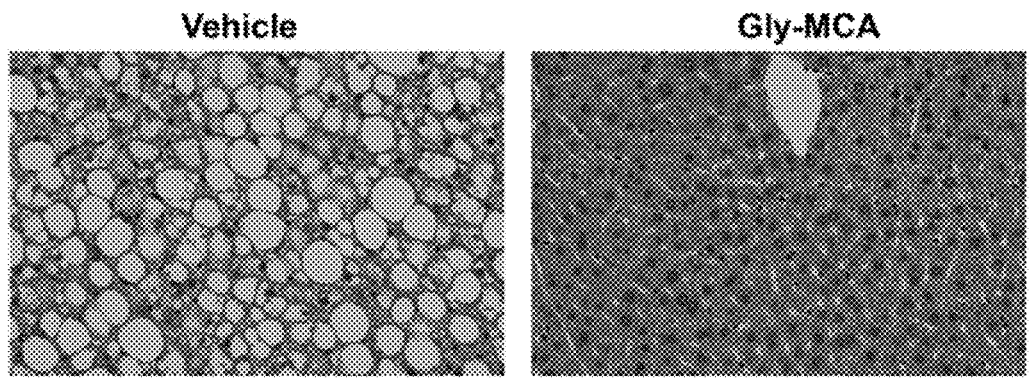

FIG. 54A shows representative H&E staining of liver sections in db/db mice treated with vehicle and Gly-MCA for 6 weeks. n=5 mice per group.

Figure 54B:
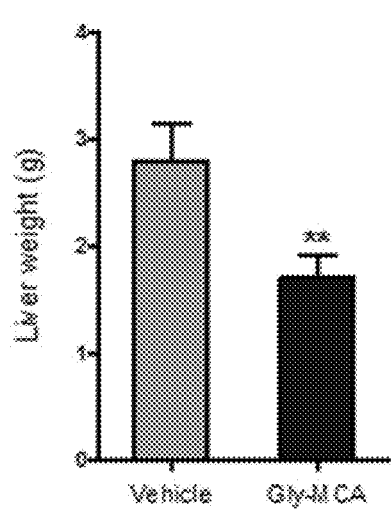
Figure 54C:
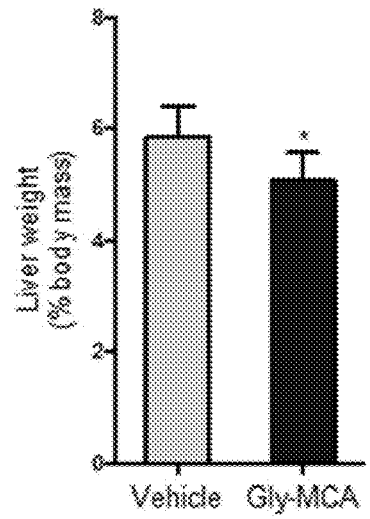

FIGS. 54B and 54C shows liver weights, and liver weight to body weight ratios in db/db mice treated with vehicle and Gly-MCA for 6 weeks. n=5 mice per group.

FIG. 54D shows liver triglyceride content of db/db mice treated with vehicle and Gly-MCA for 6 weeks. n=5 mice per group. All data are presented as mean±SD.

FIGS. 55A and 55B show serum ALT and AST levels in db/db mice treated with vehicle and Gly-MCA for 6 weeks. n=5 mice per group. All data are presented as mean±SD.

Figure 56A:
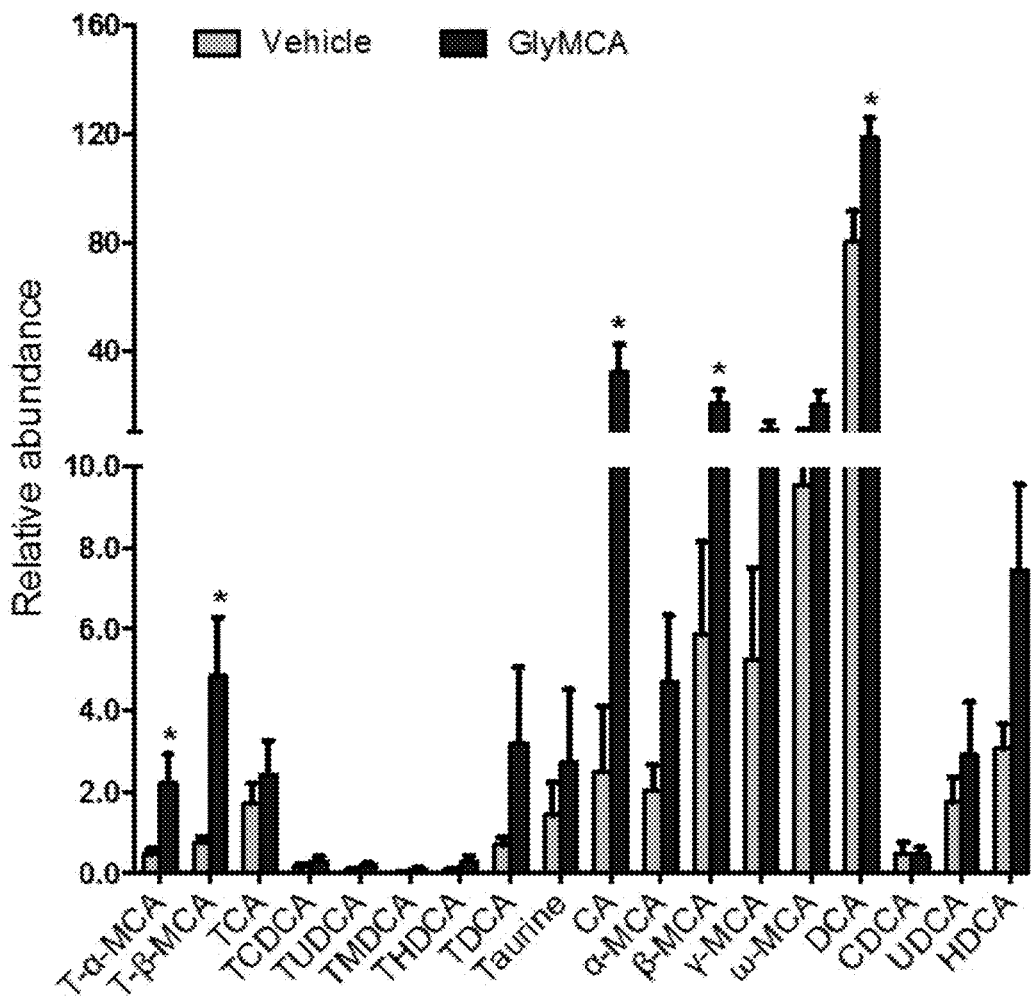
Figure 56B:
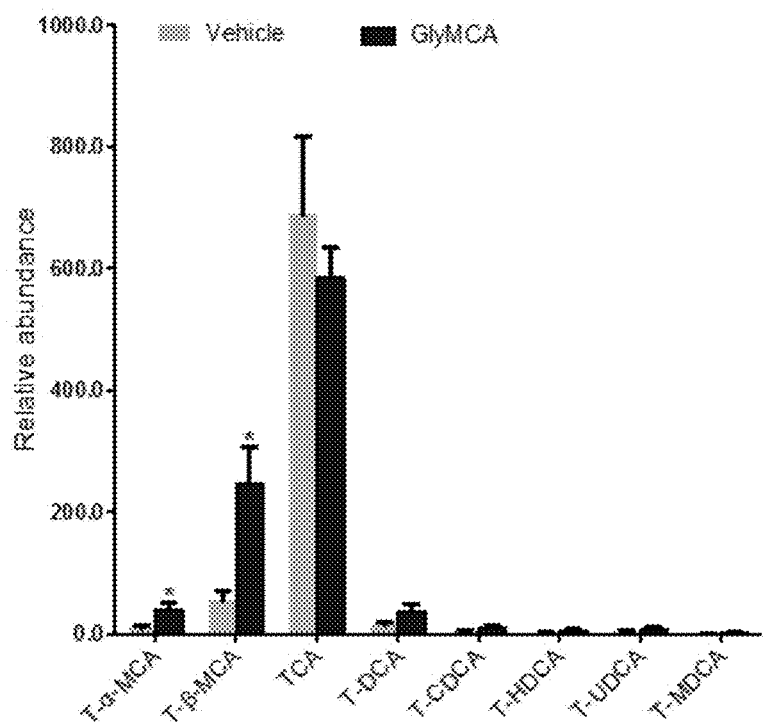

FIGS. 56A and 56B shows the bile acid composition in feces and ileum from vehicle and Gly-MCA-treated db/db mice for 6 weeks. n=5 mice per group.

Figure 56C:
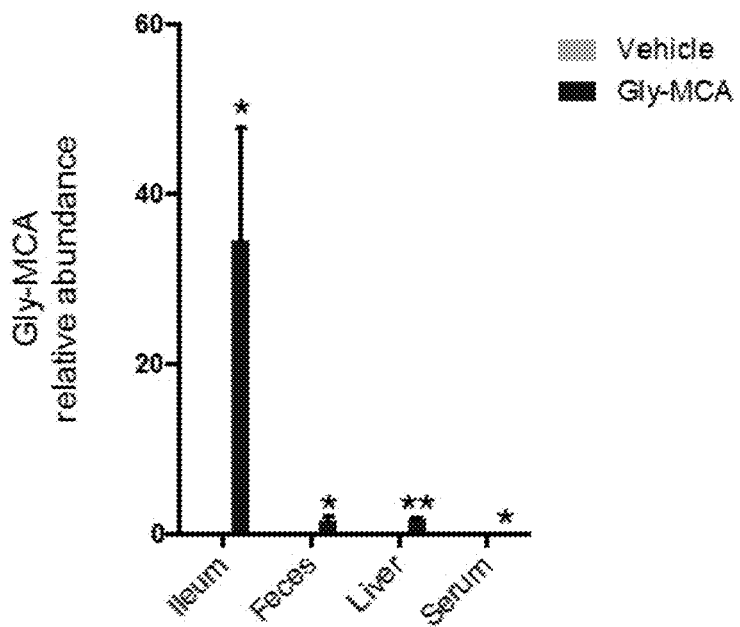

FIG. 56C shows relative levels of Gly-MCA in ileum, feces, liver and serum of vehicle and Gly-MCA-treated db/db mice for 6 weeks. n=5 mice per group. All data are presented as mean±SD.

Figure 57A:
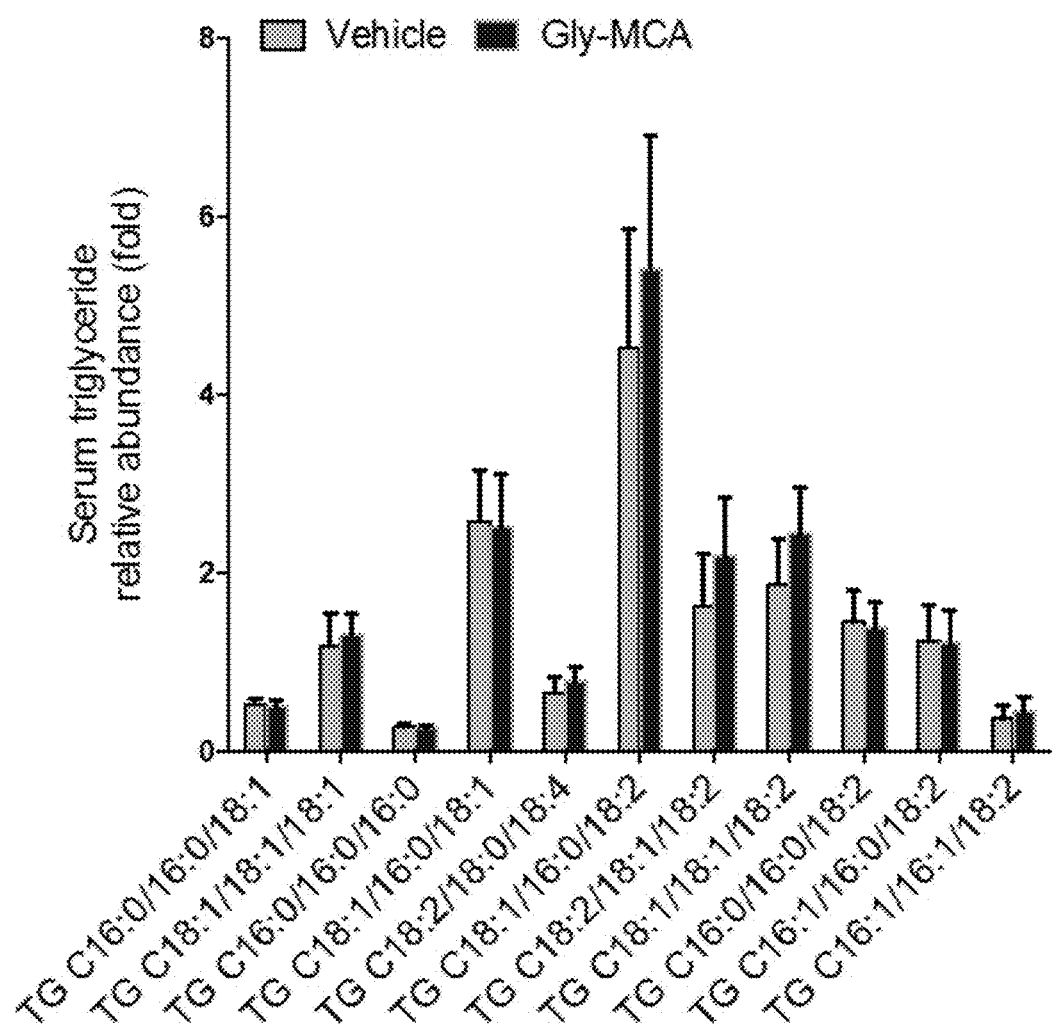

FIG. 57A shows the profile of serum triglyceride species in db/db mice treated with vehicle and Gly-MCA for 6 weeks. n=5 mice per group.

Figure 57B:
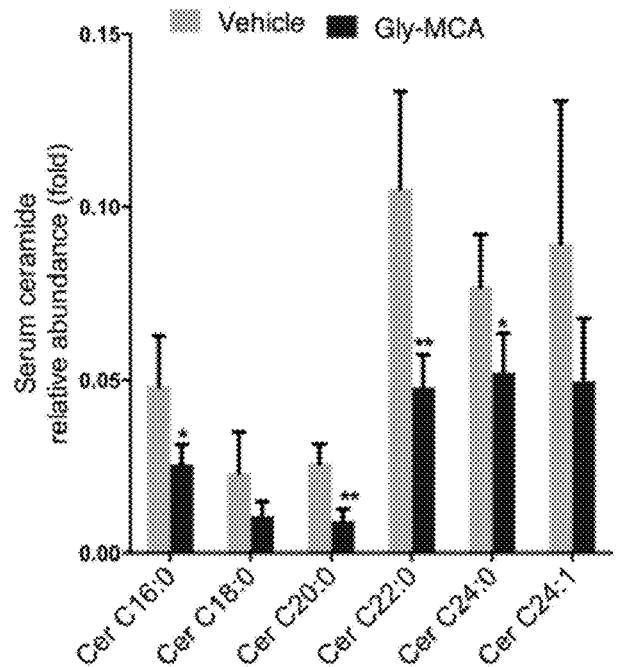
Figure 57C:
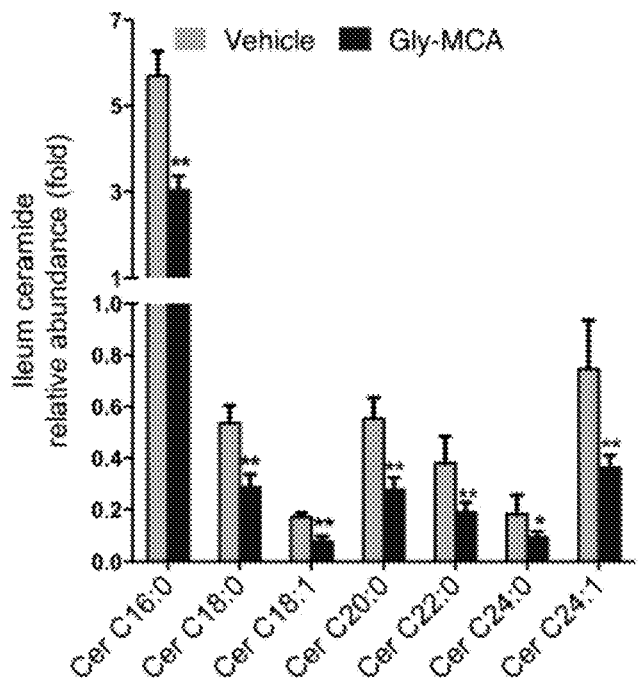

FIGS. 57B and 57C shows profiles of serum and ileum ceramides species from vehicle and Gly-MCA-treated mice fed a high-fat diet for 9 weeks. n=5 mice per group. All data are presented as mean±SD.

Figure 58:
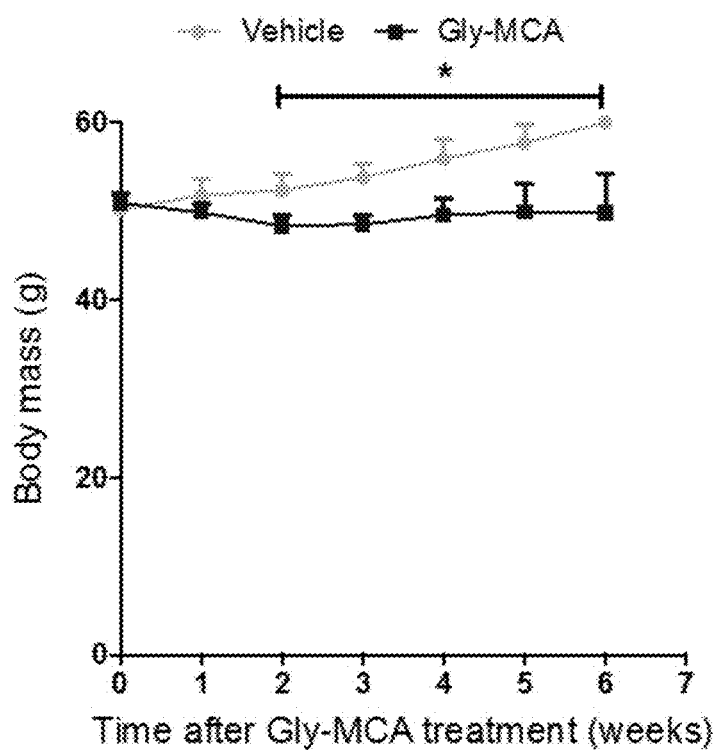

FIG. 58 show the curves of body mass of HFD-induced obese mice treated with vehicle- and Gly-MCA for 6 weeks. n=5 mice per group.

Figure 59:
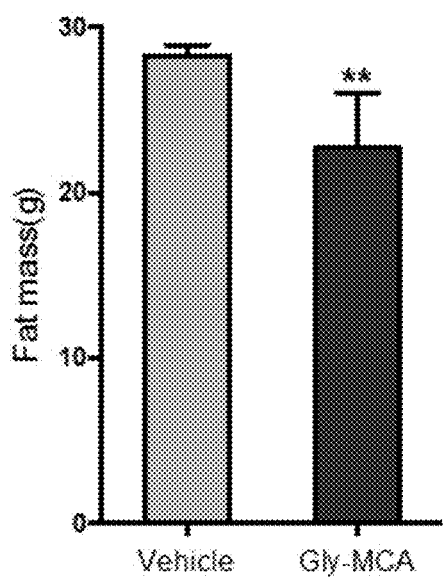

FIG. 59 show body composition as determined by NMR in high-fat diet-induced obese mice treated with vehicle- and Gly-MCA for 6 weeks. n=5 mice per group.

Figure 60A:
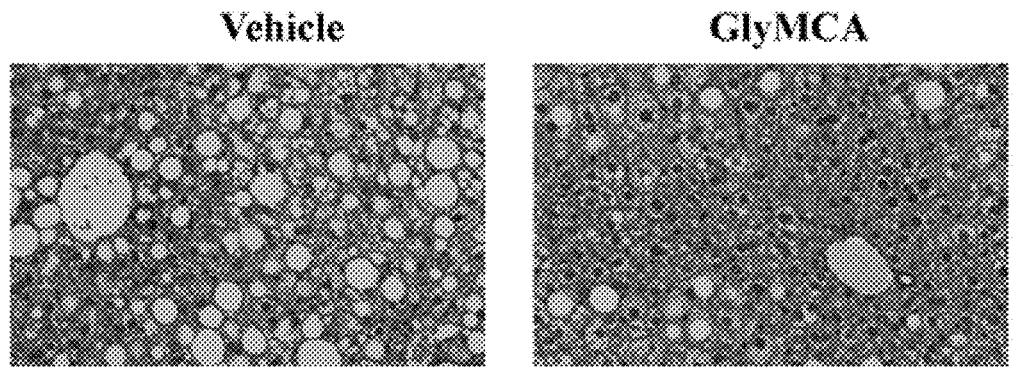

FIG. 60A shows representative H&E staining of liver sections in high-fat diet-induced obese mice treated with vehicle- and Gly-MCA for 6 weeks. n=5 mice per group.

Figure 60B:
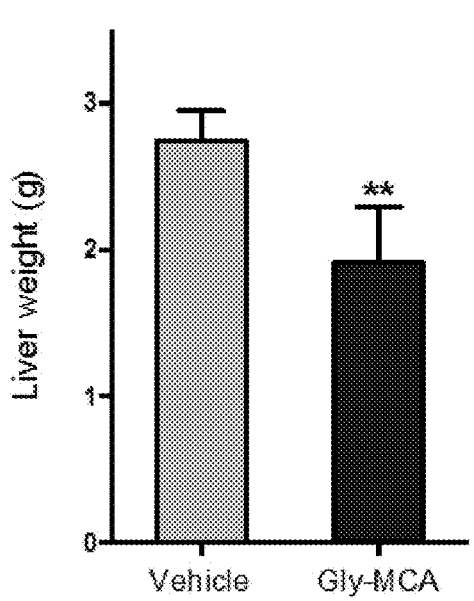
Figure 60C:
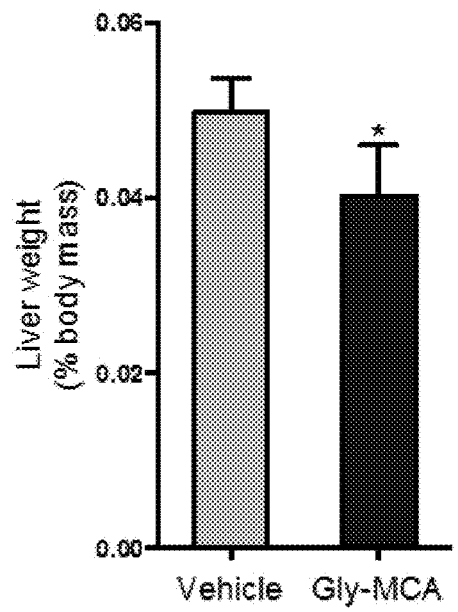

FIGS. 60B and 60C shows liver weights and liver weight to body weight ratios in high-fat diet-induced obese mice treated with vehicle- and Gly-MCA for 6 weeks. n=5 mice per group.

Figure 61A:
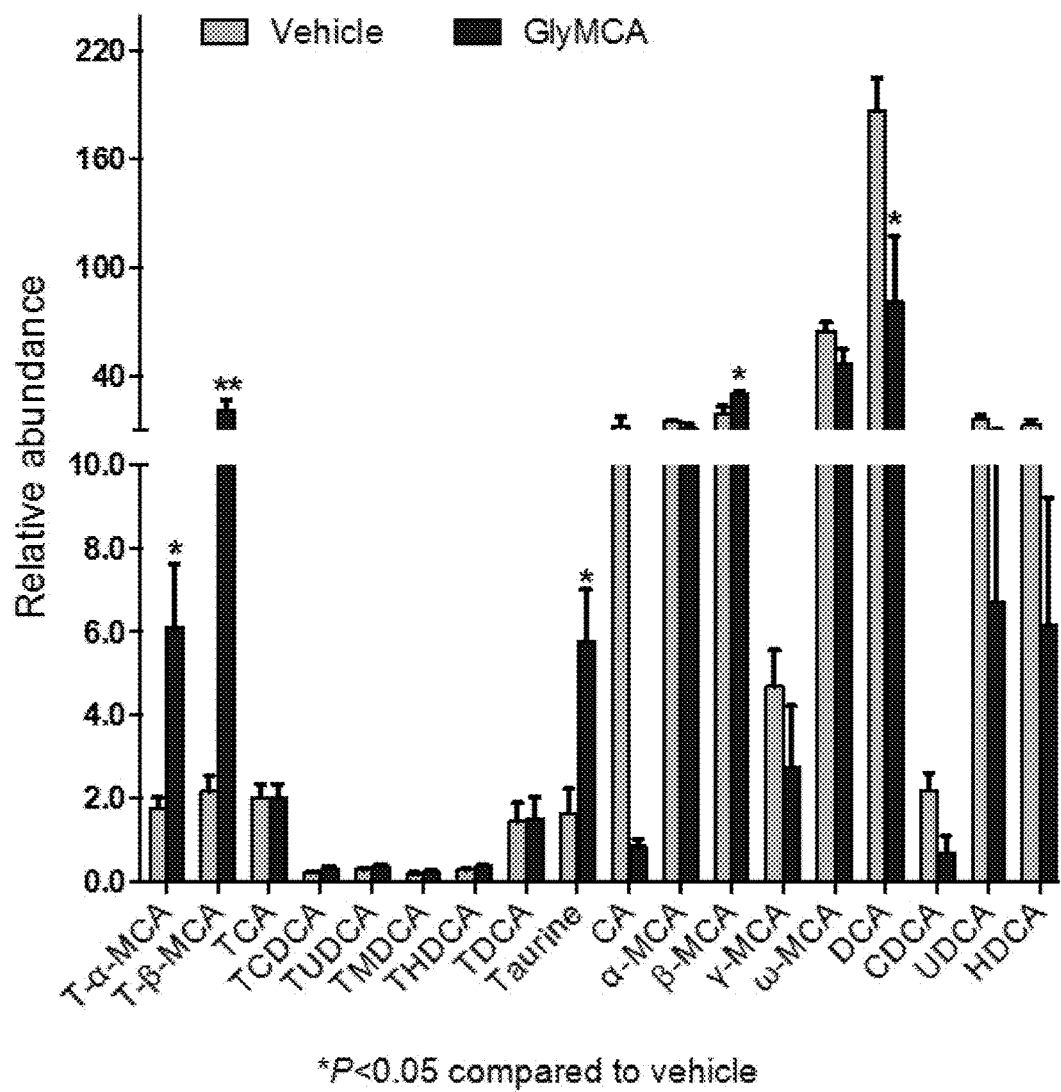
Figure 61B:
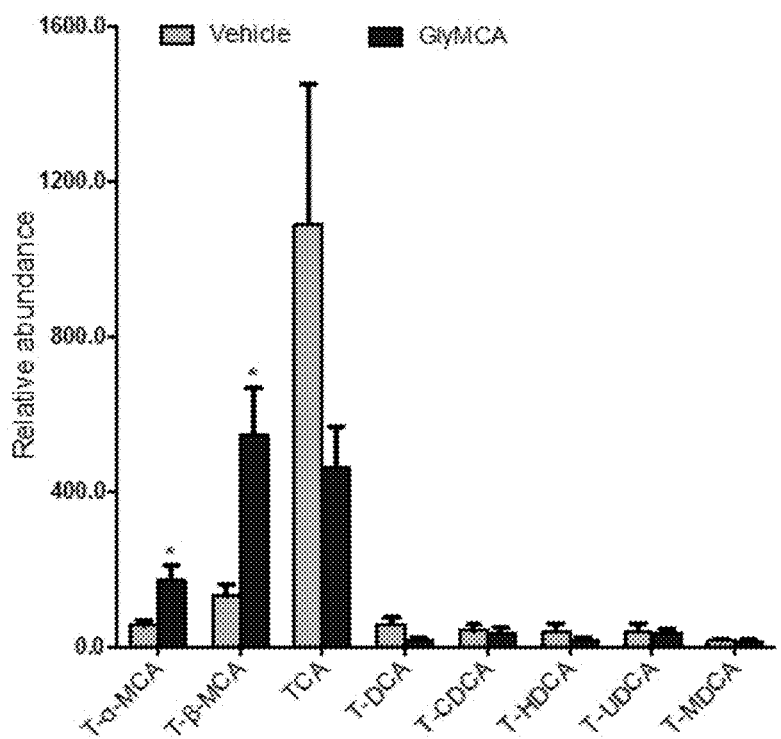

FIGS. 61A and 61B shows the bile acid composition in feces and ileum from high-fat diet-induced obese mice treated with vehicle- and Gly-MCA for 6 weeks. n=5 mice per group.

Figure 61C:
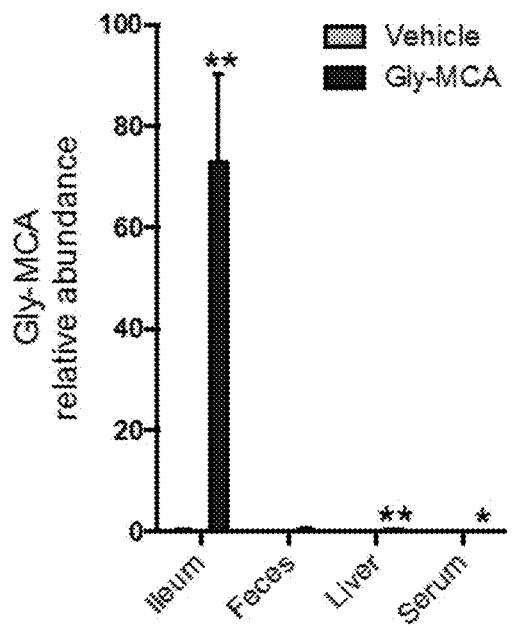

FIG. 61C shows relative levels of Gly-MCA in the ileum, feces, liver and serum of vehicle and Gly-MCA-treated high-fat diet-induced obese mice for 6 weeks. n=5 mice per group. All data are presented as mean±SD.

DETAILED DESCRIPTION OF THE INVENTION

In an embodiment, the invention provides a compound of formula (I) or (II):

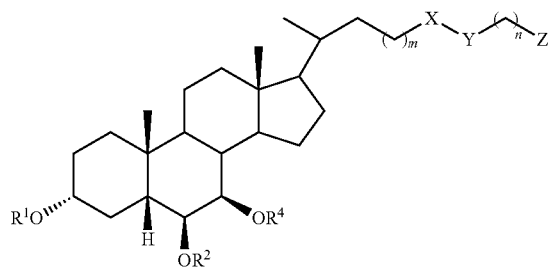

(I)

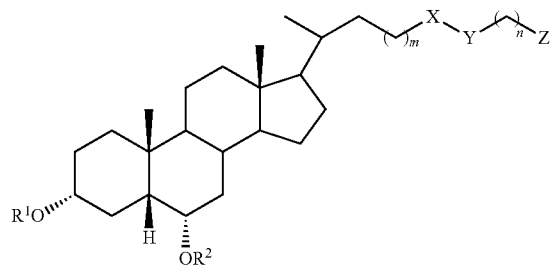

(II)

wherein $R^1$ and $R^2$ are independently selected from hydrogen, alkyl, and $C(=O)R^3$, $R^4$ is selected from hydrogen, alkyl, and $C(=O)R^3$, X is selected from C=O and $CH_2$, Y is selected from $CH_2$, $NR^5$, O, S, SO, $SO_2$, and Se, or X and Y taken together form C=C, Z is selected from $COOR^6$, $SO_3R^7$, and $P(=O)(OR^8)_2$, $R^3$, $R^5$, $R^6$, $R^7$, and $R^8$ are independently selected from hydrogen, alkyl, and aryl, $R^4$ is selected from hydrogen, alkyl, and $C(=O)R^3$, m is an integer of 1 to 6, and n is an integer of 1 to 6, or a pharmaceutically acceptable salt thereof, with the proviso that, when the compound is of formula (I), m is 1, n is 2, X is C=O, Y is NH, $R^1$ and $R^2$ are both hydrogen, and $R^4$ is hydrogen, then Z is not $SO_3H$.

In accordance with certain embodiments, when the compound is of formula (I), m is 1, X is C=O, Y is NH, $R^1$ and $R^2$ are both hydrogen, $R^4$ is hydrogen, and n is 1, then Z is not COOH.

In accordance with certain embodiments, the compound is of formula (I).

In accordance with any of the above embodiments, $R^4$ is hydrogen.

In accordance with certain embodiments, $R^1$ and $R^2$ are hydrogen.

In accordance with certain embodiments, X is C=O.

In accordance with certain embodiments, m is 2.

In accordance with certain embodiments, Y is NH.

In accordance with certain embodiments, n is an integer of 1 to 6.

In accordance with certain preferred embodiments, the compound is selected from:

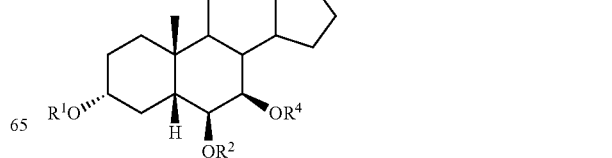

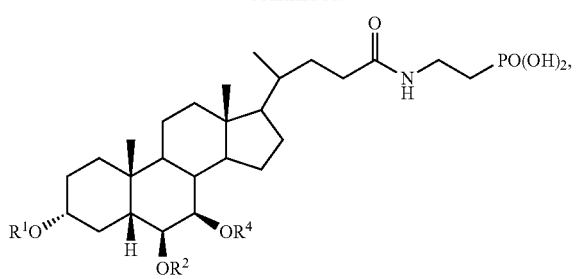

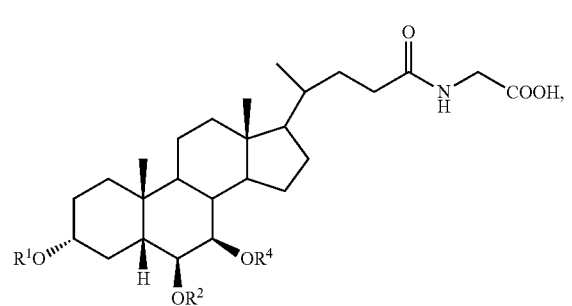

and

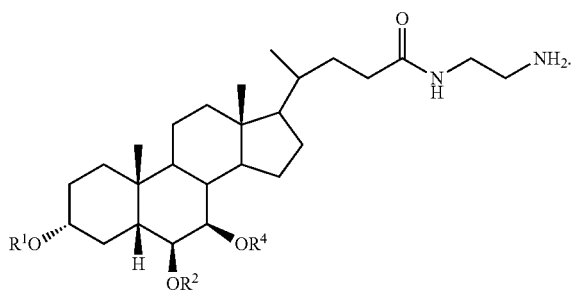

In accordance with certain preferred embodiments, the compound is selected from:

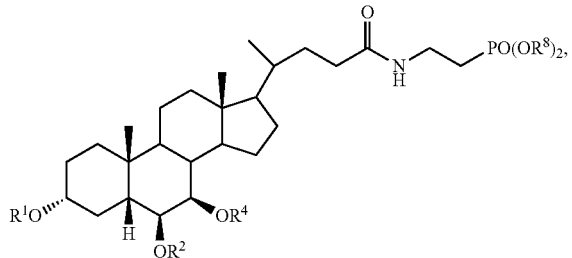

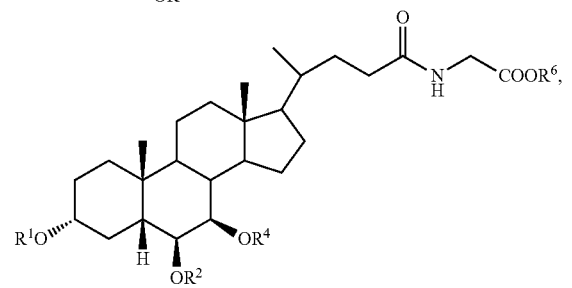

and

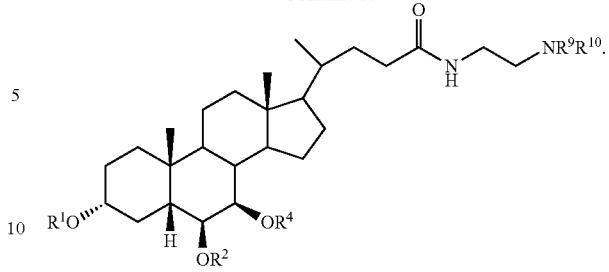

In accordance with certain embodiments, X is CH$_2$.
In accordance with certain embodiments, Y is selected from NH, O, S, and Se.
In accordance with certain embodiments, m is 2
In accordance with certain embodiments, n is 2.
In accordance with certain embodiments, Z is SO$_3$H.
In accordance with certain preferred embodiments, the compound is selected from:

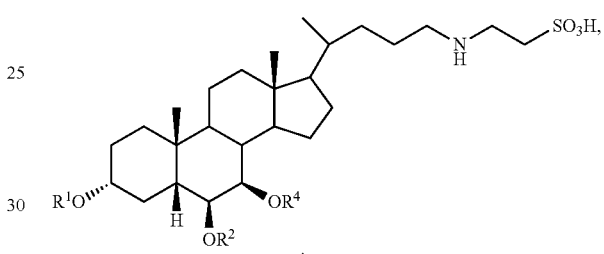

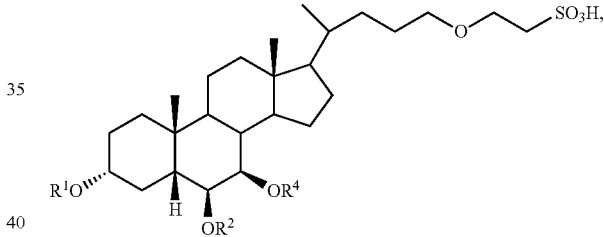

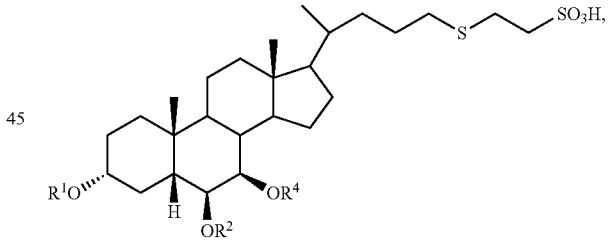

and

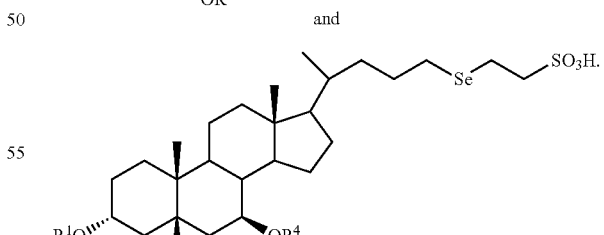

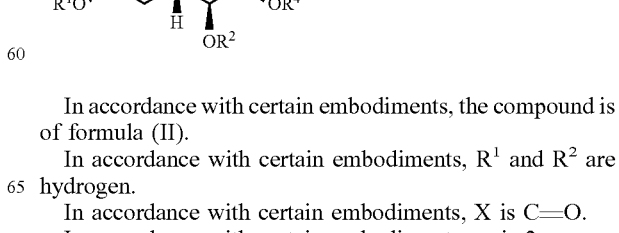

In accordance with certain embodiments, the compound is of formula (II).
In accordance with certain embodiments, R$^1$ and R$^2$ are hydrogen.
In accordance with certain embodiments, X is C=O.
In accordance with certain embodiments, m is 2.

In accordance with certain embodiments, Y is NH.

In accordance with certain embodiments, n is an integer of 1 to 6.

In accordance with certain preferred embodiments, the compound is selected from:

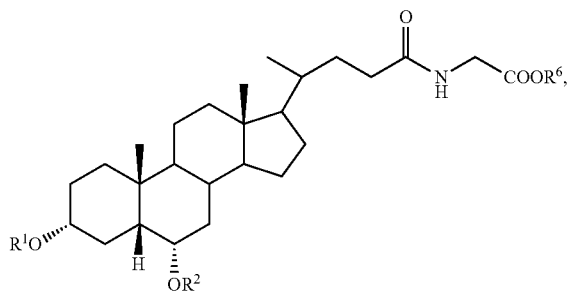

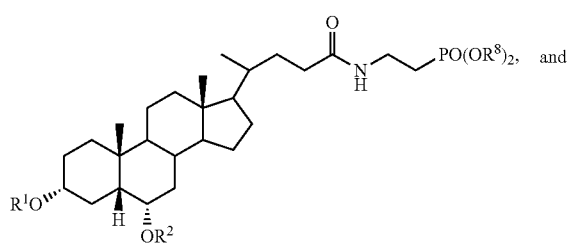

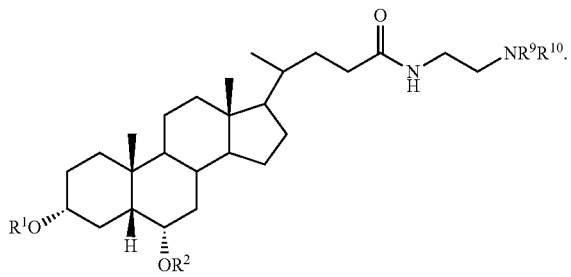

In accordance with certain preferred embodiments, the compound is selected from:

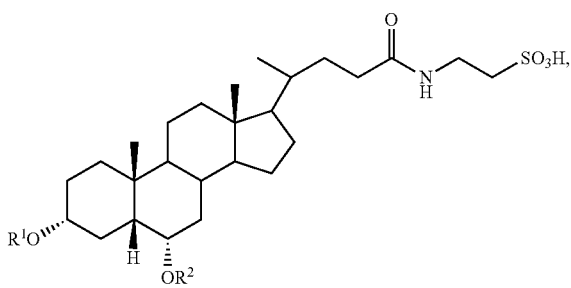

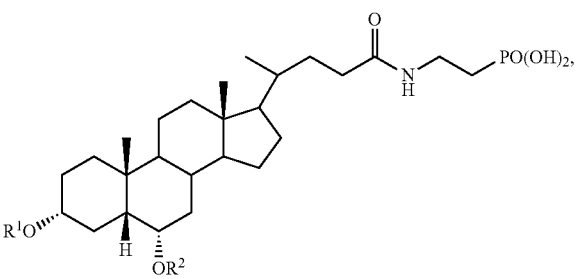

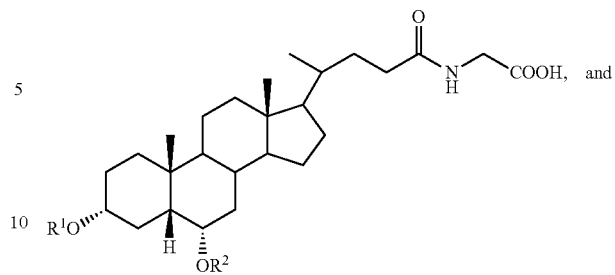

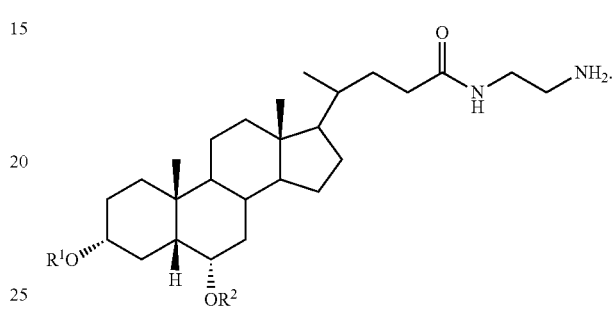

In certain embodiments, X is $CH_2$.

In accordance with certain embodiments, Y is selected from NH, O, S, and Se.

In certain embodiments, m is 2.

In certain embodiments, n is 2.

In certain embodiments, Z is $SO_3H$.

In accordance with certain preferred embodiments, the compound is selected from:

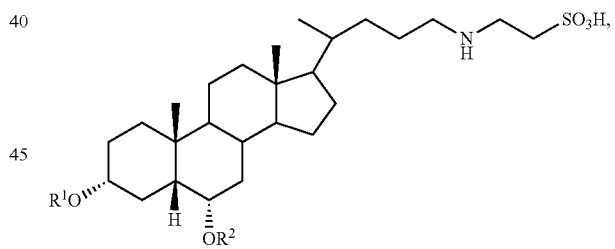

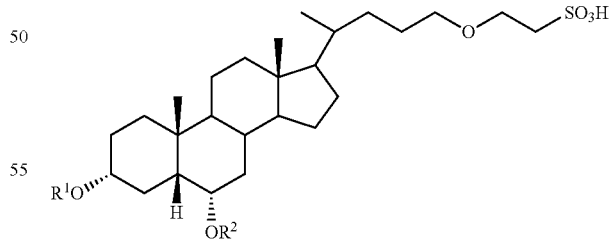

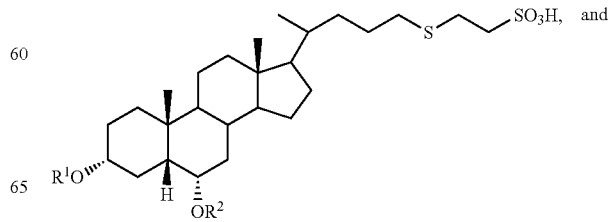

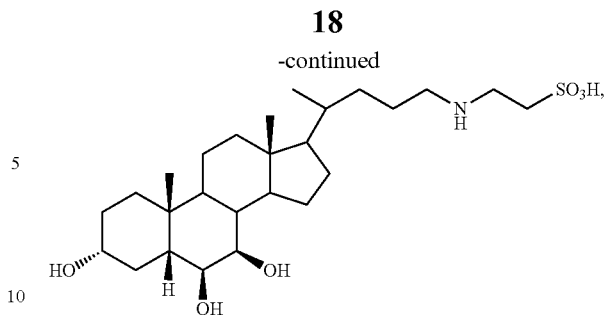
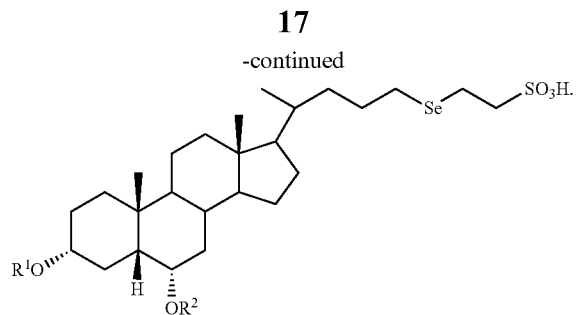
In accordance with certain more preferred embodiments, the compound is selected from:
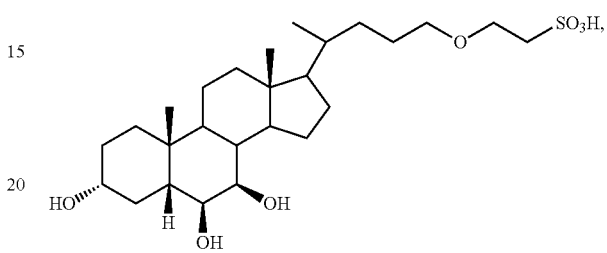
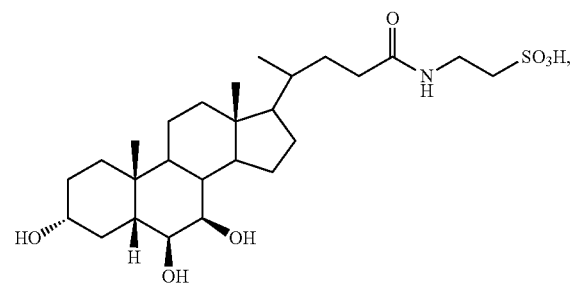
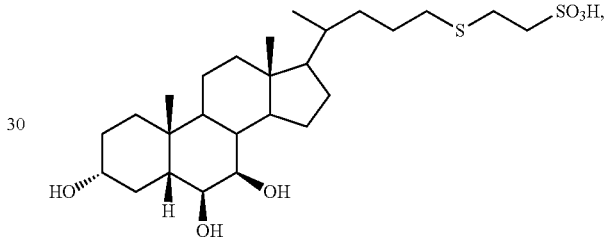
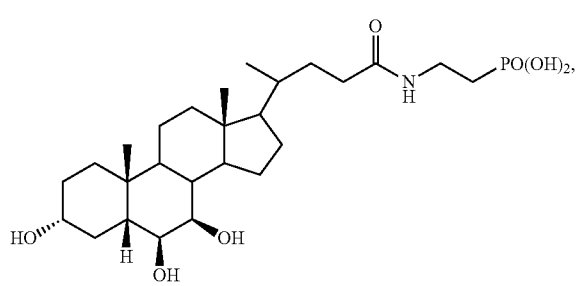
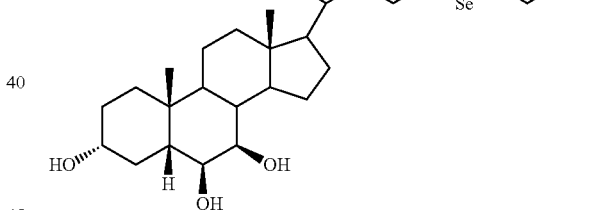
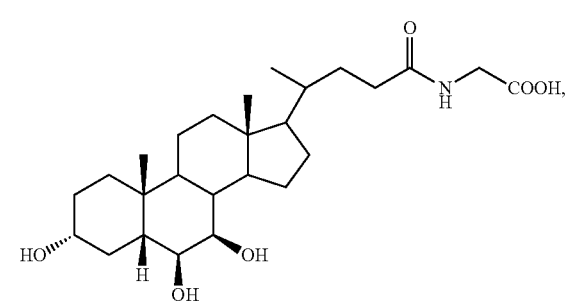
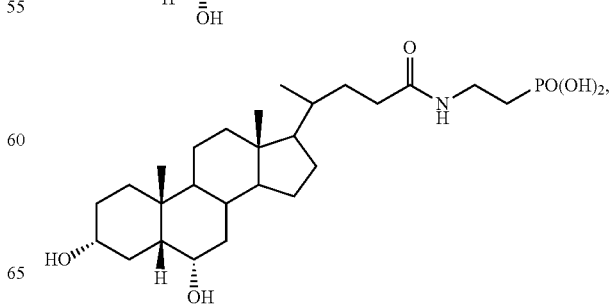
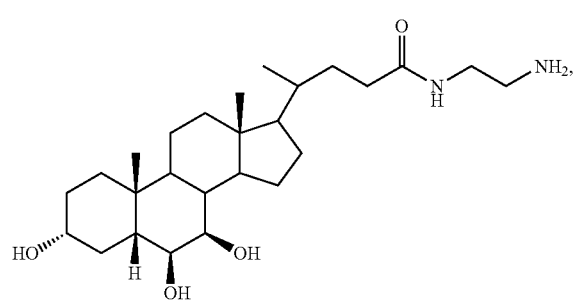

-continued

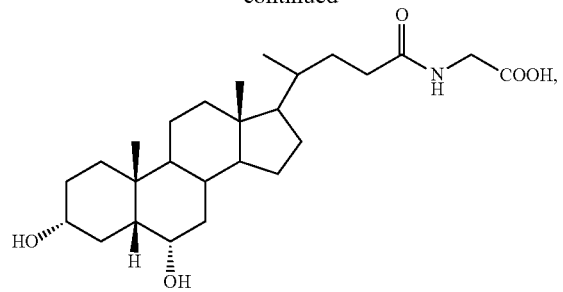

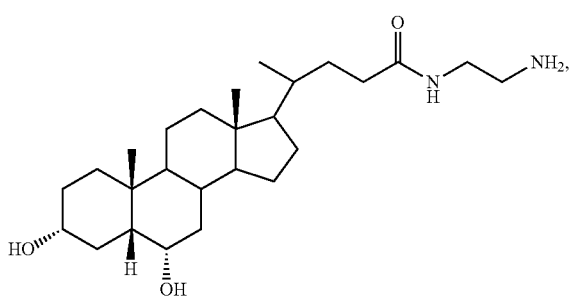

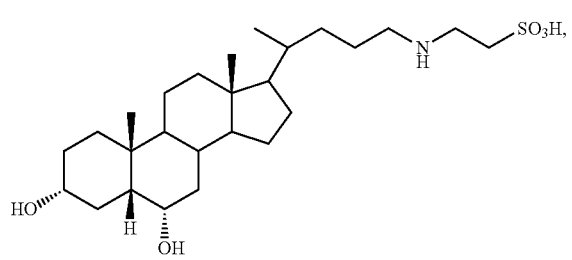

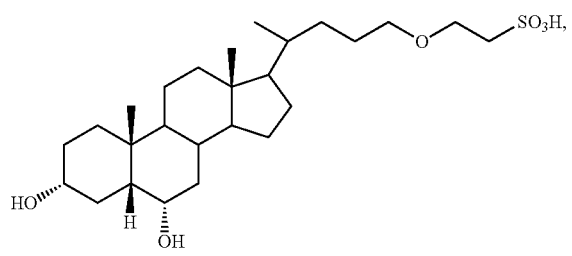

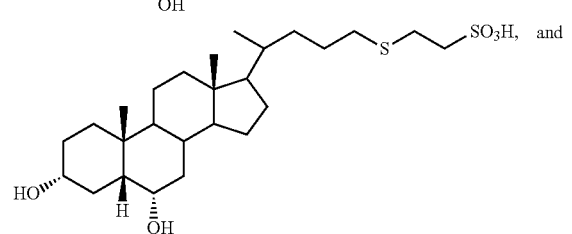

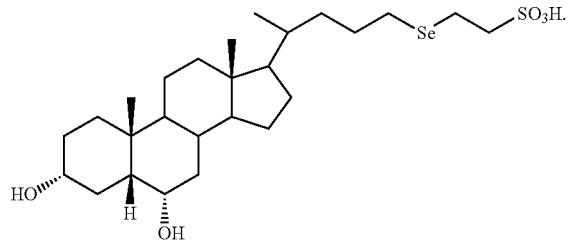

The invention also provides a compound of formula (III):

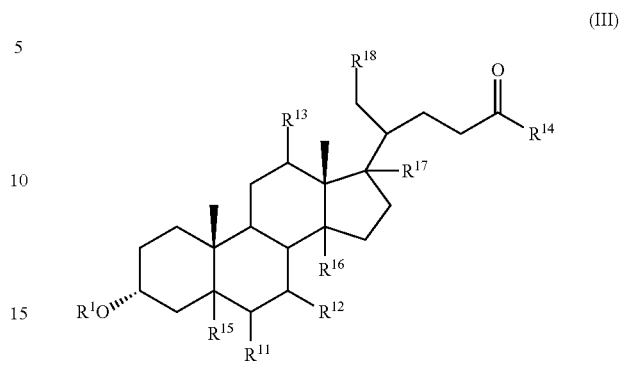

(III)

wherein $R^1$ and $R^2$ are independently selected from hydrogen, alkyl, and C(=O)$R^3$,
$R^{11}$ is hydrogen, halo, alkyl, O$R^2$, and C(=O)$R^3$,
$R^{12}$ is hydrogen, halo, alkyl, O$R^4$, or C(=O)$R^3$,
$R^{13}$ is hydrogen, alkyl, O$R^{14}$, or C(=O)$R^3$,
$R^4$ is selected from hydrogen, alkyl, and C(=O)$R^3$,
$R^3$ is hydrogen, alkyl, or aryl,
$R^{15}$, $R^{16}$, $R^{17}$, and $R^{18}$ are independently selected from hydrogen and halo, and $R^{14}$ is selected from glycino, alaninо, β-alaninо, phenylalaninо, tyrosinо, methioninо, tryptophano, leucino, isoleucino, methyl aspartato, asparto, methyl glutamo, glutamo, methyl prolino, prolino, valino, 2-fluoro-β-alanino, 2-bromoalanino, 2-chloroalanino, 2-fluoroalanino, 2-iodoalanino, 3-bromoalanino, 3-chloroalanino, 3-fluoroalanino, 3-iodoalanino, 4-bromophenylalanino, 4-chlorophenylalanino, 4-fluorophenylalanino, taurino, and 4-iodophenylalanino,
or a pharmaceutically acceptable salt thereof,
with the provisos that, when $R^1$ is hydrogen, $R^{11}$ and $R^{12}$ are both β-hydroxyl, $R^{13}$, $R^{15}$, $R^{16}$, $R^{17}$, and $R^{18}$ are all hydrogen, then $R^{14}$ is not glycine or taurine, and,
when $R^1$ is hydrogen, $R^{11}$ is α-hydroxyl, $R^{12}$, $R^{13}$, $R^{15}$, $R^{16}$, $R^{17}$, and $R^{18}$ are all hydrogen, then $R^{14}$ is not glycine or taurine.

In certain embodiments, the compound is selected from:

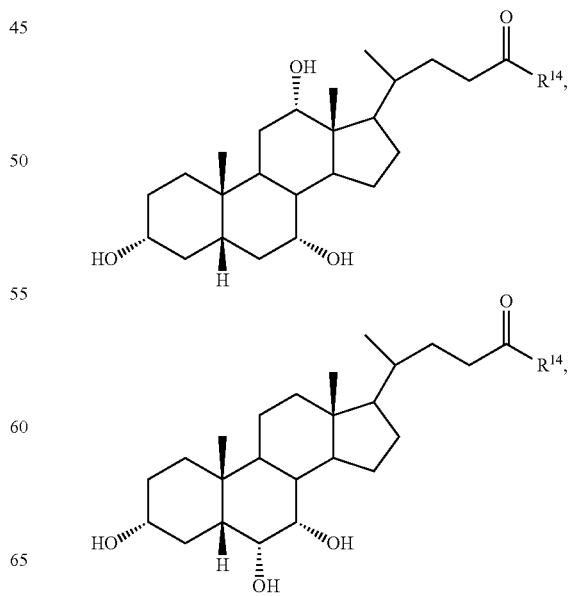

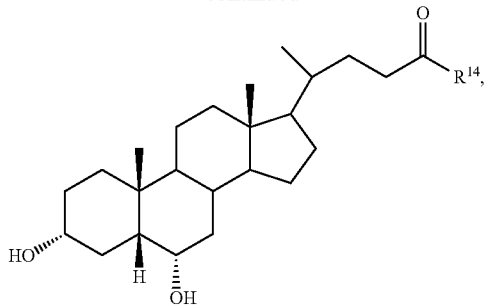

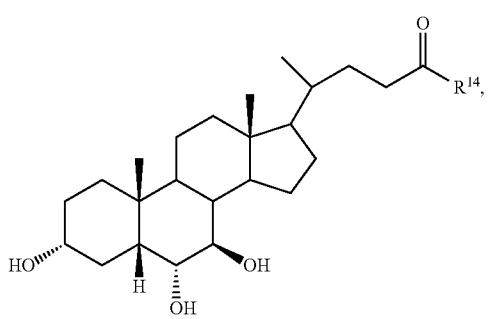

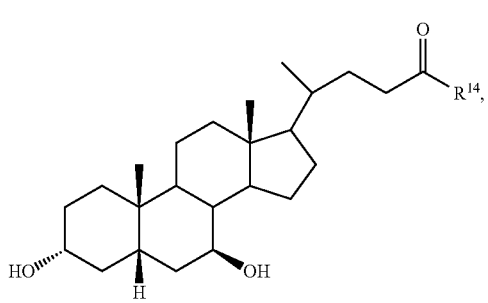

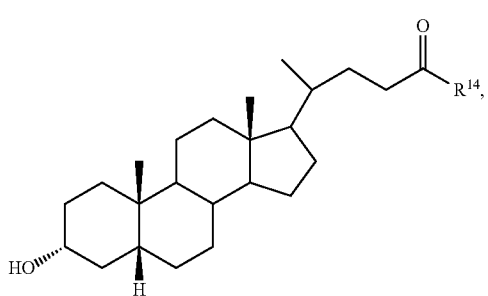

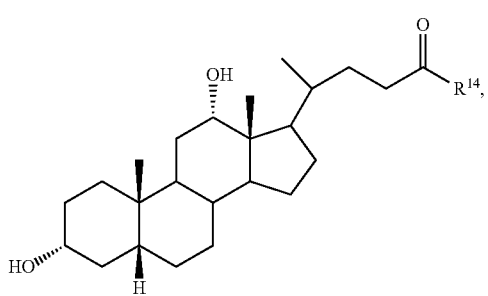

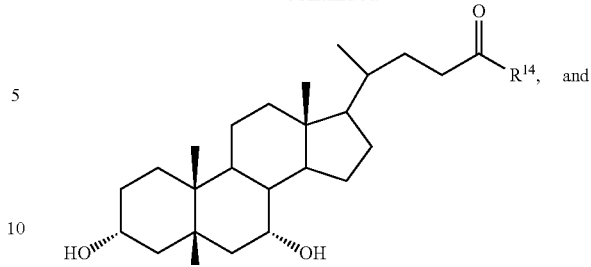

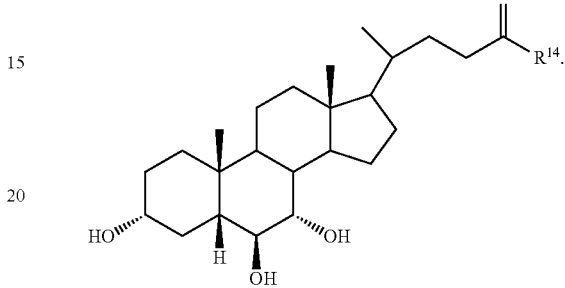

In certain embodiments, $R^{11}$ is halo, $R^{12}$ and $R^{13}$ is hydroxyl, and $R^{15}$, $R^{16}$, $R^{17}$, and $R^{18}$ are all hydrogen.

In certain embodiments, and $R^{12}$ are both halo, and $R^{15}$, $R^{16}$, $R^{17}$, and $R^{18}$ are all hydrogen.

In certain embodiments, $R^{18}$ is halo and $R^{15}$, $R^{16}$, and $R^{17}$ are all hydrogen.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2\pi$ electrons, according to Hückel's Rule.

In any of the above embodiments, the C-20 carbon atom of the compound or salt of Formula (I) or (II) can have an R configuration, an S configuration, or can be a mixture of R and S isomers.

In any of the above embodiments, when the stereochemistry at a chiral carbon atom is not specified, the chiral carbon atom can have an R configuration, an S configuration, or can be a mixture of R and S isomers.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. In certain embodiments, the formulation is suitable for administration to the alimentary tract, and in particular, to the small intestine.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

In some embodiments, the formulation can be suitable to prolonging the amount of time that the compound of the present invention is contacted with the alimentary tract of the mammal, and in particular with the small intestine of the mammal. In this regard, various formulations such as extended release formulation and formulations designed to prolong the amount of time that the compound is retained in the stomach before release into the small intestine can be utilized. A number of suitable formulations are presented in *Remington: The Science and Practice of Pharmacy*, Gennaro, A. R., ed., pp. 858-929, Lippincott Williams and Wilkins (2000).

In some embodiments, the compound or salt of the present invention can be administered in the form of a food additive, that is, in admixture with foodstuffs or beverages. For use as a food additive, the compound or salt can be mixed with a foodstuff or beverage per se, or can be formulated as a composition comprising one or more suitable excipients prior to mixing with a foodstuff or beverage. The foodstuff or beverage can be any suitable foodstuff or beverage. In some embodiments, the foodstuff or beverage has a relatively high fat content.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

In certain embodiments, the pharmaceutical composition can be administered parenterally, e.g., intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions. Many such compositions are known in the art.

In accordance with an embodiment, the invention provides a method of inhibiting a farnesoid X receptor in a mammal in need thereof, which method comprises administering to the mammal an effective amount of a compound of the invention.

Preferably, the animal is a mammal. More preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

In certain embodiments, the FXR-mediated disease or condition is cardiovascular disease, atherosclerosis, arteriosclerosis, hypercholesteremia, or hyperlipidemiachronic liver disease, gastrointestinal disease, renal disease, cardiovascular disease, metabolic disease, cancer (i.e., colorectal cancer), or neurological indications such as stroke. In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis. In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease. In certain embodiments, the cardiovascular disease is atherosclerosis, arteriosclerosis, dyslipidemia, hypercholesterolemia, or hypertriglyceridemia.

In accordance with a preferred embodiment, the invention provides a method of treating or preventing obesity in a mammal in need thereof, comprising administering to the mammal an effective amount of a compound or salt of the invention.

As used herein, obesity can be considered as a condition in which excess body fat may put a person at health risk (see Barlow and Dietz, *Pediatrics* 102: E29, 1998; National Institutes of Health, *Obes. Res.* 6 (suppl. 2):51S-209S, 1998). Excess body fat is a result of an imbalance of energy intake and energy expenditure. In one embodiment in humans, the Body Mass Index (BMI) is used to assess obesity. In one embodiment, a BMI of 25.0 kg/m$^2$ to 29.9 kg/m$^2$ is overweight (also called grade I obesity), while a BMI of 30 kg/m$^2$ is truly obese (also called grade II obesity).

In another embodiment in humans, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

The dose administered to a mammal, particularly a human, in accordance with the present invention should be sufficient to effect the desired response. Such responses include reversal or prevention of the undesirable effects of the disease or disorder mediated by the farnesoid X receptor expressed in the intestine for which treatment is desired or to elicit the desired benefit. In certain embodiments, the disorder is non-alcoholic fatty liver disease, obesity and type 2 diabetes (insulin resistance). One skilled in the art will recognize that dosage will depend upon a variety of factors, including the age, condition, and body weight of the human, as well as the extent of the non-alcoholic fatty liver disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that successful treatment of non-alcoholic fatty liver disease, obesity, type 2 diabetes (insulin resistance) or other disease or disorder may require prolonged treatment involving multiple administrations.

In this regard, treatment of NAFLD via inhibition of the intestinal farnesoid X receptor can be regarded as a reduction in the clinical manifestations of hepatic steatosis in a mammal. While in many cases NAFLD does not cause signs or symptoms, NAFLD may cause fatigue, pain, particularly in the upper right abdomen, and weight loss. In some instances, NAFLD may progress to nonalcoholic steatohepatitis, an inflammation in the liver. NAFLD may progress to nonalcoholic fatty liver disease-associated cirrhosis which is a scarring of the liver accompanied by markedly decreased liver function. Over time, scarring can become so severe that the liver no longer functions adequately.

NAFLD can be assessed, for example, by ultrasound, computed tomography, magnetic resonance studies, or by liver biopsy. In certain embodiments, the mammal is consuming a high fat diet. A high fat diet can be considered as one that provides more than 30% of energy as fat (see, for example, Churchill Livingstone's Dictionary of Sport and Exercise Science and Medicine, S. Jennett, Elsevier Limited, 2008). In other embodiments, the invention provides a method of preventing non-alcoholic fatty liver disease in a mammal. Preventing non-alcoholic fatty liver disease can be regarded as reducing an expected manifestation of hepatic steatosis in a mammal that is subjected to a dietary change from a low fat or intermediate fat diet to a high fat diet.

Currently, no standard treatment for NAFLD exists. Physicians typically treat the risk factors that contribute to the disease. For example, physicians assist afflicted patients with weight loss programs and choice of a healthy diet, control of diabetes, and lowering of cholesterol.

In this regard, treatment of obesity via inhibition of the farnesoid X receptor can be regarded as a reduction in the rate of weight gain in a mammal. In certain embodiments, the mammal is consuming a high fat diet. A high fat diet can be consider as one which provides more than 30% of energy as fat (see, for example, Churchill Livingstone's Dictionary of Sport and Exercise Science and Medicine, S. Jennett, Elsevier Limited, 2008). In other embodiments, the invention provides a method of preventing obesity in a mammal. Preventing obesity can be regarded as reducing an expected weight gain in a normal weight mammal that is subjected to a dietary change from a low fat or intermediate fat diet to a high fat diet.

In this regard, treatment of diabetes via inhibition of the farnesoid X receptor can be regarded as a reduction of insulin resistance in a patient afflicted therewith. Insulin resistance can result in hyperglycemia, and a reduction in insulin resistance can result in a lowering of blood glucose levels. Non-limiting examples of symptoms that be treated via inhibition of the farnesoid X receptor include brain fogginess and inability to focus, high blood sugar, intestinal bloating, sleepiness, weight gain, fat storage, difficulty losing weight, increased blood triglyceride levels, increased blood pressure, increased pro-inflammatory cytokines associated with cardiovascular disease, depression, *acanthosis nigricans*, and increased hunger.

The dose administered to a mammal, particularly, a human, in accordance with the present invention should be sufficient to effect the desired response. Such responses include reversal or prevention of the bad effects of the disease or disorder mediated by the farnesoid X receptor for which treatment is desired or to elicit the desired benefit. In certain embodiments, the disorder is obesity. One skilled in the art will recognize that dosage will depend upon a variety of factors, including the age, condition, and body weight of the human, as well as the extent of the obesity in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that successful treatment of obesity or other disease or disorder may require prolonged treatment involving multiple administrations.

In this regard, treatment of obesity via inhibition of the farnesoid X receptor can be regarded as a reduction in the rate of weight gain in a mammal. In certain embodiments, the mammal is consuming a high fat diet. A high fat diet can be consider as one which provides more than 30% of energy as fat (see, for example, Churchill Livingstone's Dictionary of Sport and Exercise Science and Medicine, S. Jennett, Elsevier Limited (2008)). In other embodiments, the invention provides a method of preventing obesity in a mammal. Preventing obesity can be regarded as reducing an expected weight gain in a normal weight mammal that is subjected to a dietary change from a low fat or intermediate fat diet to a high fat diet.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg (e.g., about 0.1 to about 150 mg, about 0.1 to about 100 mg, or about 0.1 to about 50 mg) of one or more of the compounds described above per kg body weight of the mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

As demonstrated herein, farnesoid X receptor is implicated in the development of obesity. Thus, administration of inhibitors of farnesoid X receptor is expected to treat or prevent the development of obesity, particularly in a mammal consuming a high fat diet.

Here, it has also been shown that intestinal farnesoid X receptor plays an essential role in the progression of NAFLD. Inhibition of intestinal farnesoid X receptor in embodiments of the invention has been shown to ameliorate NAFLD induced by a high fat diet.

Through studies on tempol and antibiotics that remodel and kill gut bacteria, respectively, a novel pathway was uncovered in which these agents alter the population of the gut microbiota resulting in loss of bacteria that express the enzyme bile salt hydrolase (BSH). Lower BSH results in increased levels of conjugated bile acids in the intestine, such as T-β-MCA. T-β-MCA in turn is an antagonist of intestinal FXR. Lower FXR signaling in the intestine results in decreased obesity, insulin resistance and NAFLD in mice fed a high-fat diet, and in genetically obese mice. These studies led to the hypothesis that inhibiting FXR would be a promising approach for treating patients with obesity, insulin resistance and NAFLD. Oral administration of a new chemical entity glycine β-muricholic acid (Gly-MCA) decreases obesity, insulin resistance and NAFLD in high-fat diet-treated mice and in genetically obese mice. It is proposed that any compound that is orally administered and retained in the intestine and that inhibits intestinal FXR and has no effect on FXR expressed in liver, would have utility in the treatment of patients with obesity, insulin resistance and NAFLD.

Chemistry

Figure 8:
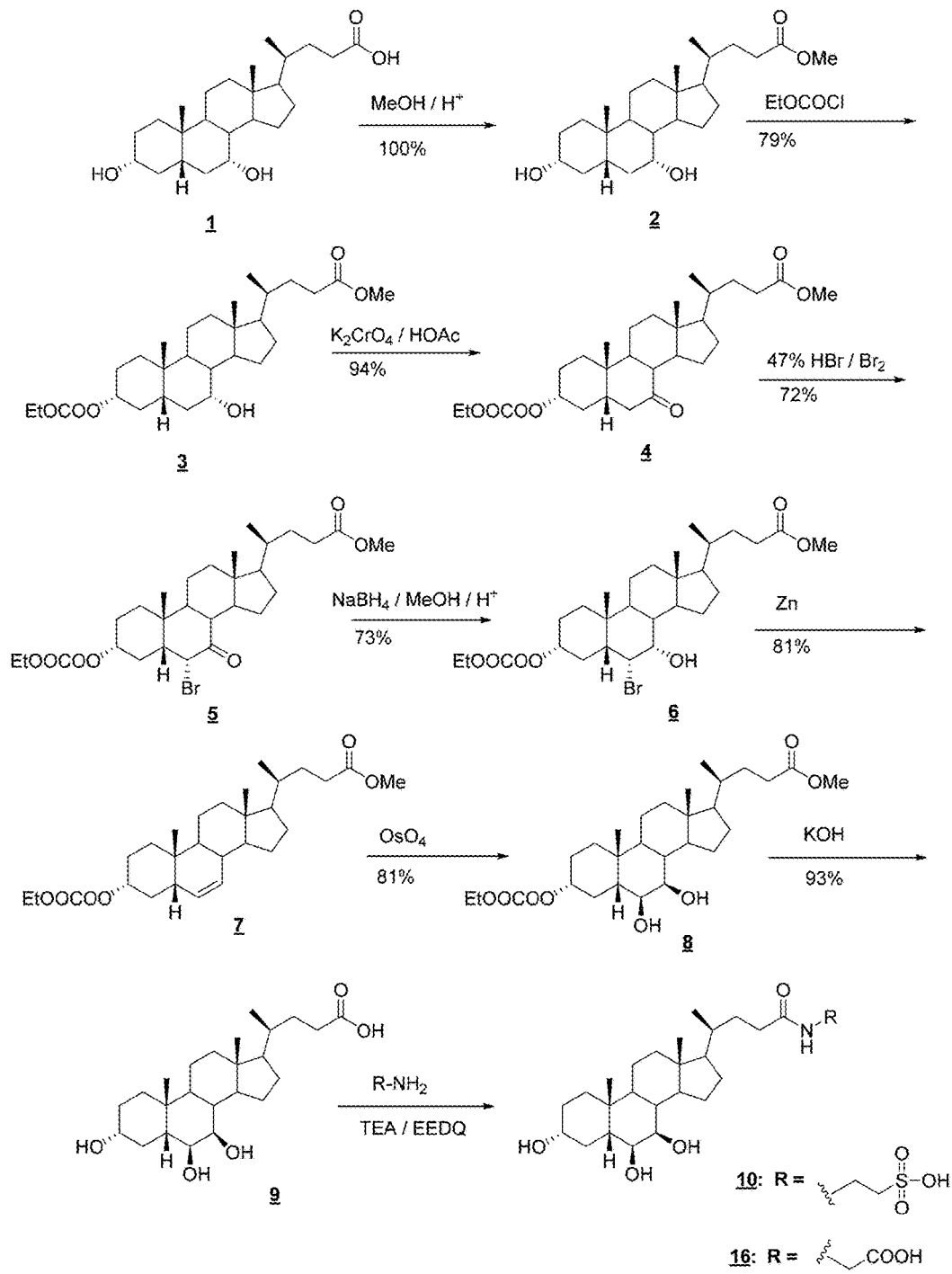
FIG. 8 depicts a synthesis of compounds in accordance with an embodiment of the invention.

Compounds of formula 1, wherein W is $OR^4$, $R^4$ is hydrogen, $R^1$ and $R^2$ are hydrogen, X is C=O, m is 1 and Y is NH, such as β-Muricholic acid 9 and conjugates thereof, such as the representative embodiments of tauro-β-Muricholic acid 10 and glycine-β-Muricholic acid 16 can be prepared as illustrated in the scheme set forth in FIG. 8. Esterification of the dihydroxy acid 1 with, for example, methanol under acid catalysis provides ester 2. Protection of the A-ring hydroxyl group with ethyl chloroformate provides carbonate 3. Oxidation of the 7-hydroxyl group with, for example potassium chromate gives ketone 4. Bromination with, for example, bromine in HBr gives bromo ketone 5. Reduction of the ketone with, for example, gives bromo alcohol 6. Reductive elimination of bromine using, for example, zinc metal provides olefin 7. Cis-dihydroxylation with, for example, osmium tetroxide gives cis diol 8. Hydrolysis of both esters provides β-muricholic acid 9. β-muricholic acid 9 can be conjugated with taurine using a suitable coupling agent provides tauro-β-muricholic acid 10. Glycine can be substituted for taurine to provide the glycine conjugate of β-muricholic acid 2-aminoethylphosphonic acid can be substituted for taurine to provide the phosphonic acid analog of tauro-β-muricholic acid. The chemistry is as described in Iida, T., et al., *Lipid*, 16: 863-5 (1981), Lida T., et al., *Journal of Lipid Research*, 30: 1267-1279 (1989), and Tserng K-Y., et al., *J Lipid Research*, 18: 404-407 (1977).

Figure 9:
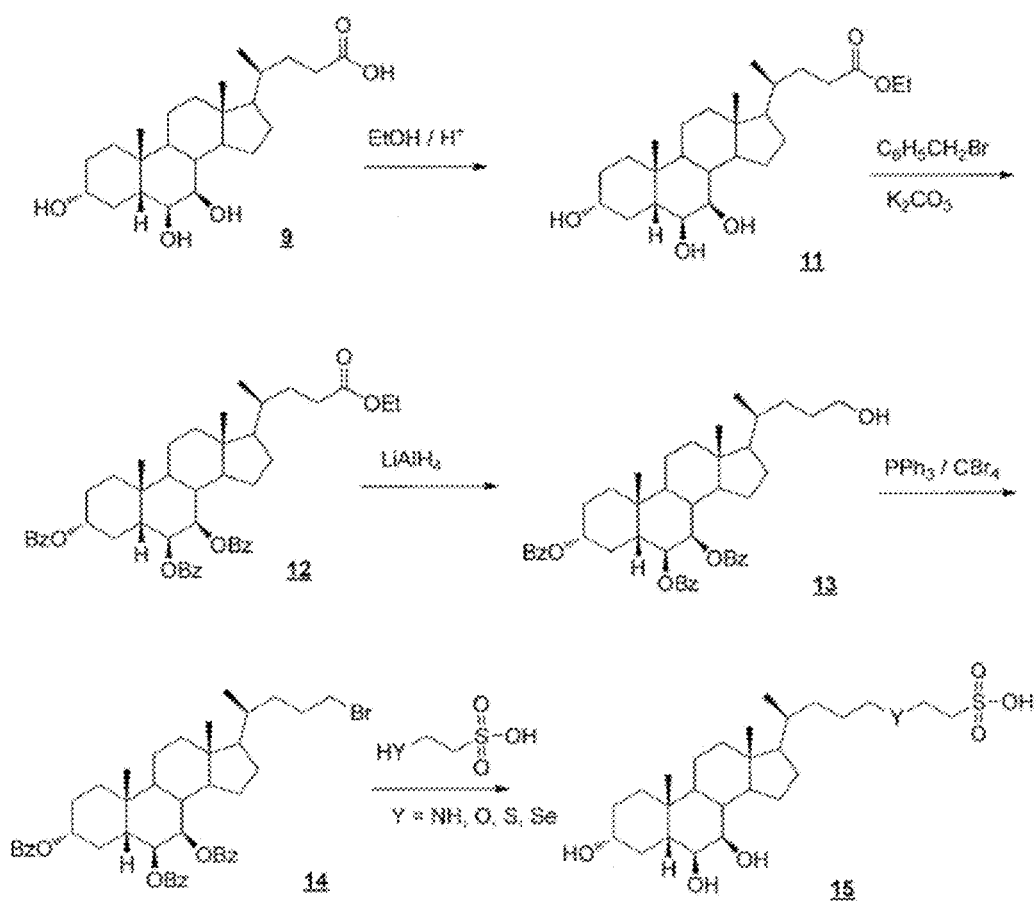
FIG. 9 depicts a synthesis of compounds in accordance with an embodiment of the invention.

Compounds of formula I, wherein X is $CH_2$, wherein m is 2, can be prepared for example by the route illustrated in FIG. 9, starting with the illustrative embodiment of β-muricholic acid 9. The carboxylic acid is protected via acid-catalyzed esterification to provide compound 11. The hydroxyl groups in compound H can be protected using any suitable protecting group such as benzyl (Bzl) to give compound 12. Reduction of the carboxyl group using any suitable reducing agent, for example, lithium aluminum hydride provides alcohol 13. Conversion of the hydroxyl group to a suitable leaving group, for example, bromo, using any suitable reagents such as triphenylphosphine and carbon tetrabromide gives compound 14. Displacement of the leaving group in 13 using, for example, a nucleophilic reagent of the formula: $HYCH_2CH_2SO_3H$ wherein Y is NH, O, S, or Se followed by deprotection gives taurine conjugated analog 15.

In an embodiment, the invention provides a method of synthesizing the compound of formula (I):

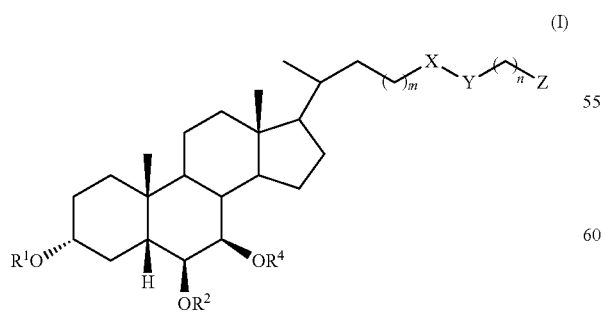

wherein $R^1$, and $R^2$, and $R^4$ are hydrogen,
X is $CH_2$,
Y is selected from $CH_2$, $NR^5$, O, S, SO, $SO_2$, and Se, Z is selected from $COOR^6$, $SO_3R^7$, $P(=O)(OR^8)_2$ and $NR^9R^{10}$, $R^3$, $R^5$, $R^6$, $R^7$, $R^8$ $R^9$, and $R^{10}$ are independently selected from hydrogen, alkyl, and aryl, $R^4$ is selected from hydrogen, alkyl, and $C(=O)R^3$, m is an integer of 1 to 6, and n is an integer of 1 to 6, comprising the steps of:

(i) providing a compound of formula (IV):

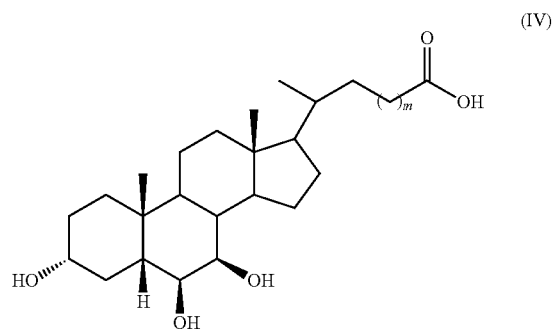

(ii) treating the compound of formula (IV) with an alcohol to provide a compound of formula (V):

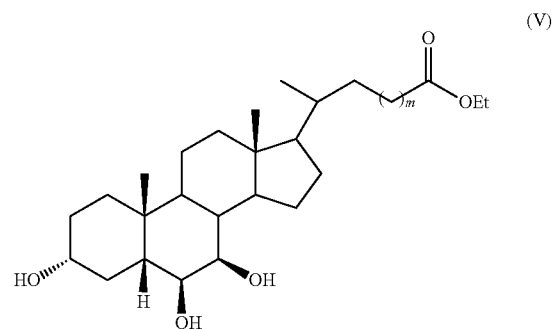

(iii) protecting the hydroxyl groups in the compound of formula (V) to provide a compound of formula (VI):

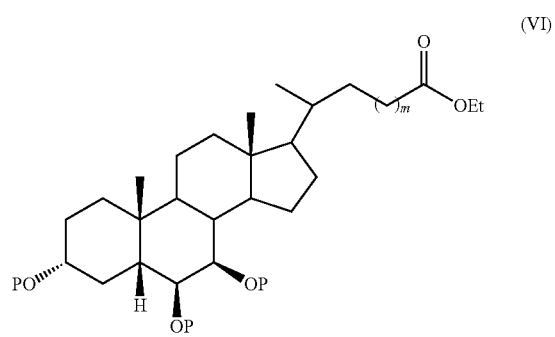

(iv) treating the compound of formula (VI) with a reducing agent to provide a compound of formula (VII):

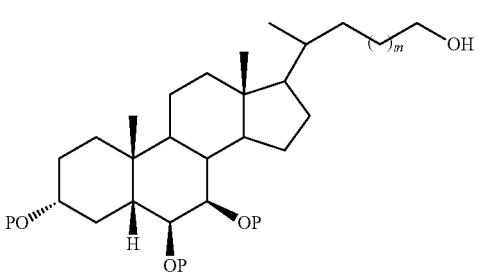

(v) converting the compound of formula (VII) to a compound of formula (VIII), wherein LG is a leaving group:

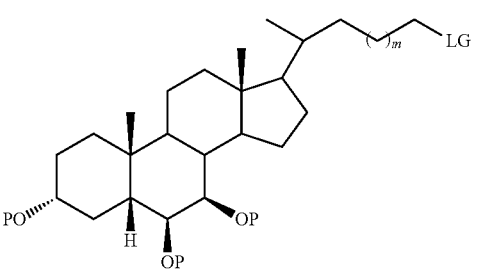

(vi) treating the compound of formula (VIII) with a compound of the formula: HY(CH$_2$)$_n$Z wherein Y is NH, S, O, or Se to provide a compound of formula (IX):

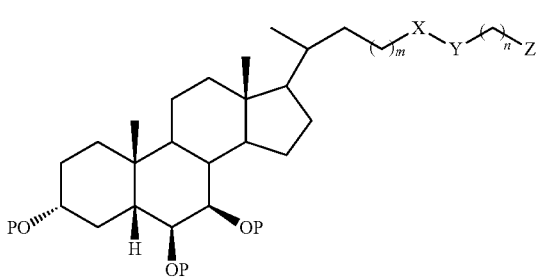

and
(vii) converting the compound of formula (IX) into the compound of formula (I).

In an embodiment, the invention provides a method of synthesizing the compound of formula (II):

(II)

wherein R$^1$ and R$^2$ are hydrogen,
X is CH$_2$,
Y is selected from CH$_2$, NR$^5$, O, S, SO, SO$_2$, and Se,
Z is selected from COOR$^6$, SO$_3$R$^7$, P(=O)(OR$^8$)$_2$ and NR$^9$R$^{10}$, R$^3$, R$^5$, R$^6$, R$^7$, R$^8$ R$^9$, and R$^{10}$ are independently selected from hydrogen, alkyl, and aryl,
R$^4$ is selected from hydrogen, alkyl, and C(=O)R$^3$,
m is an integer of 1 to 6, and
n is an integer of 1 to 6,
comprising the steps of:
(i) providing a compound of formula (X):

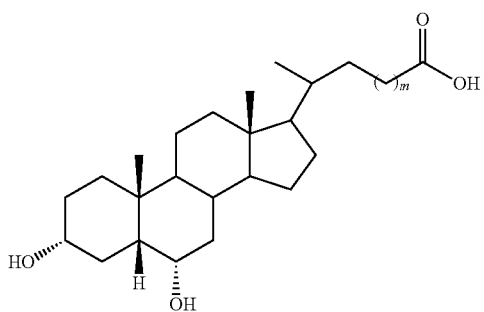

(ii) treating the compound of formula (X) with an alcohol to provide a compound of formula (XI):

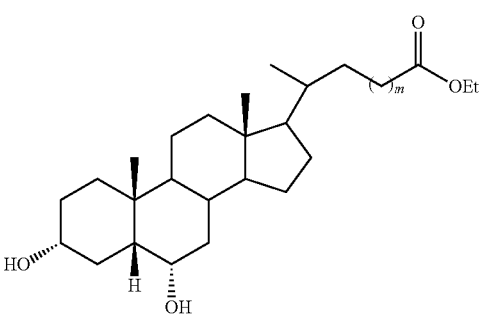

(iii) protecting the hydroxyl groups in the compound of formula (XI) to provide a compound of formula (XII):

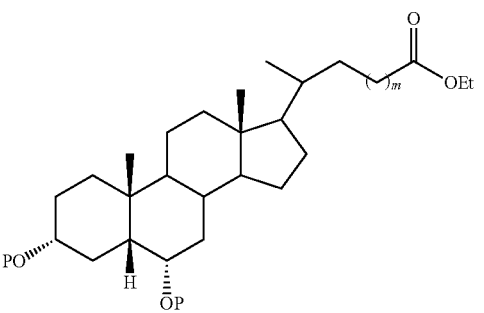

(iv) treating the compound of formula (XII) with a reducing agent to provide a compound of formula (XIII):

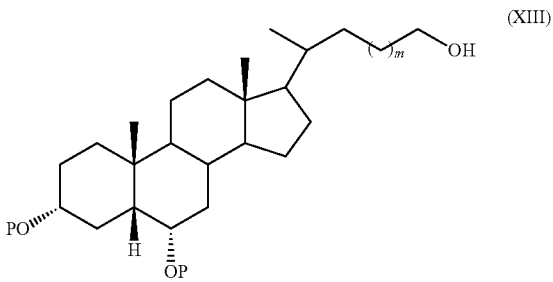

(XIII)

(v) converting the compound of formula (XIII) to a compound of formula (XIV), wherein LG is a leaving group:

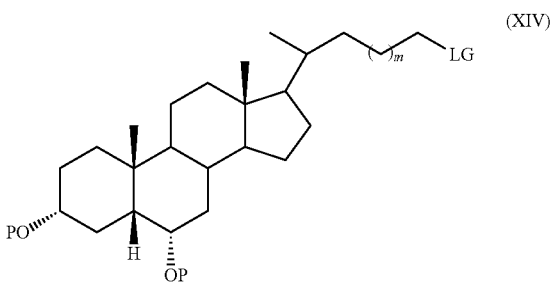

(XIV)

(vi) treating the compound of formula (XIV) with a compound of the formula: $HY(CH_2)_nZ$ wherein Y is NH, S, O, or Se to provide a compound of formula (XV):

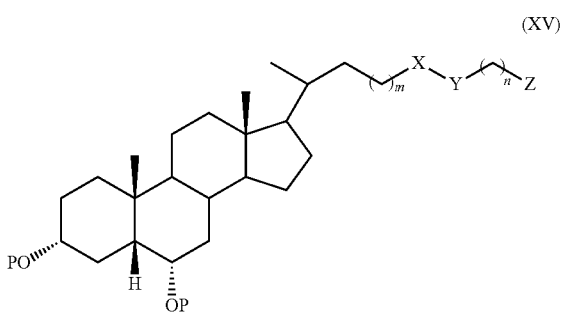

(XV)

and (vii) converting the compound of formula (XV) into the compound of formula (II).

The following examples further illustrate the invention but, of course, should not be construed as in any way limiting its scope.

Luciferase Assay

The PGL4-Shp-TK firefly luciferase construct and human Fxr expression plasmid were provided by Grace L. Guo of Rutgers University. The human Asbt expression plasmid was provided by Paul A. Dawson of Wake Forest University School of Medicine. The plasmids were transfected into cells using X-TREMEGENE™ HP DNA Transfection Reagent (Roche). The cells were lysed, and luciferase activities measured with a DUAL-LUCIFERASE™ assay kit (Promega). Firefly luciferase activity was normalized to *Renilla* luciferase activity.

ATP Assay

ATP detection was performed using the following protocol. For extraction of ATP, 10 mg of ileum mucosa were homogenized with 1.0 mL of ice-cold TE saturated phenol (Sigma-Aldrich). A mixture of 200 μL of chloroform and 150 μL of deionized water were added and the homogenate thoroughly shaken for 20 s and centrifuged at 10,000 g for 5 min at 4° C. The aliquot from the supernatant was diluted 100-fold with deionized water, and 10 μL of the diluted extract was measured by ATP determination kit (Invitrogen Corp.) (Chida et al., *Analytica Chimica Acta* 727: 8-12 (2012).

Tempol, bacitracin, neomycin, and streptomycin were purchased from Sigma-Aldrich (St. Louis, Mo.). Bile acids were ordered from Steraloids, Inc. (Newport, R.I.) and Sigma (St. Louis, Mo.), and taurocholic acid-d5 sodium salt was from Toronto Research Chemicals Inc. (Toronto, Ontario). Ceramides were obtained from Avanti Polar Lipids. HFD (60 kcal % fat) were purchased from Bio-Sery (Frenchtown, N.J.). T-β-MCA and Gly-MCA were synthesized as according to the scheme shown in FIG. 41 and described in Example 1. All solvents and organic reagents were of the highest grade available.

Animal Studies

High-fat diet (HFD) (60% kcal consisting of fat) was purchased from Bioserv. Inc. Intestine-specific Fxr-null ($Fxr^{\Delta IE}$) mice and wild-type ($Fxr^{fl/fl}$) mice had a C57BL/6N genetic background. $Fxr^{fl/fl}$ and $Fxr^{\Delta IE}$ (Kim et al., *J. Lipid Res.* 48:2664-2672, 2007) mice were backcrossed with C57BL/6N mice for over 10 generations. For the antibiotic (the combination of bacitracin, neomycin, and streptomycin) study, male C57BL/6N mice from 6 weeks of age were fed a high-fat diet ("HFD) and administered 0.1% (w/v) of each compound (the combination of bacitracin, neomycin, and streptomycin) in the drinking water. For the tempol study, male C57BL/6N mice from 6 weeks of age were fed a HFD and administered 0.064% (w/v) tempol in the drinking water. For TβMCA in vivo, male C57BL/6N mice from 6 weeks of age were fed a HFD and treated with the antibiotics (0.1% of each compound of bacitracin, neomycin, and streptomycin combination) for 3 days. Vehicle (saline), TCA (400 mg/kg body weight, dissolved in saline) or a combination of TCA and TβMCA (400 mg/kg body weight of each compound, dissolved in saline) were orally administered to the mice and followed by a second dose 12 h later. The mice were killed 2 h later for tissue collection. For the Gly-MCA study, Gly-MCA was custom synthesized. Bacon-flavored dough pills were produced as described (Walker et al., *Toxicol. Appl. Pharmacol.* 260:65-69, 2012) for oral administration of Gly-MCA (0.25 mg Gly-MCA/pill, dose of 10 mg/kg). Mice were trained to eat the dough pills prior to the study. For the prevention of obesity, insulin resistance and NAFLD, male wild-type (WT) C57BL/6N mice, 6- to 8-weeks-old, were fed a high-fat diet (Bio-Serv, Frenchtown, N.J.; 60 kcal % fat) from the age of 6 weeks and were orally administered with vehicle (control pills) or Gly-MCA (0.25 mg/pill/day, dose 10 mg/kg). C57BL/6N mice fed a high-fat diet for 12 weeks were administered (0.25 mg Gly-MCA/pill, dose of 5 mg/kg). Leptin-deficient db/db mice, 6- to 8-weeks-old, fed a chow diet, were administered Gly-MCA (0.25 mg/pill/day, 10 mg/kg). Mice were housed individually in their home cages. Cumulative food intake and $TEE_{bal}$ were measured for 1 week in vehicle and Gly-MCA-treated mice from 6 to 7 weeks of HFD. $TEE_{bal}$ was measured as previously described (Ravussin et al., *Int. J. Obesity* 37:399-403, 2013).

All animal studies were performed in accordance with the Institute of Laboratory Animal Resources guidelines and approved by the NCI Animal Care and Use Committee.

Preparation and Culture of Primary Hepatocytes

Primary hepatocytes from 6-week-old C57BL/6N mice were obtained by collagenase 1 (Invitrogen, Carlsbad, Calif.) perfusion. The cells were purified by 45% Percoll (Sigma, St. Louis, Mo.) density centrifugation and cultured in DMEM (Invitrogen, Carlsbad, Calif.) with 10% fetal bovine serum and 1% Insulin-Transferrin-Selenium-Ethanolamine (ITS-X) (Invitrogen, Carlsbad, Calif.). The viability of hepatocytes was determined using trypan blue dye exclusion, and those with higher than 85% viability were used. The medium was changed to DMEM with 1% fetal bovine serum after culturing for 4 hours. After starvation for 4 hours, the cells were exposed to ceramide. At the prescribed time points, cells were harvested and subjected to qPCR analysis and TG content detection.

RNA Analysis

The mucosa of intestine was gently scraped and liver was taken and both were flash frozen in liquid nitrogen and stored at −80° C. until RNA was prepared. RNA was extracted from frozen intestine and liver using TRIzol reagent (Invitrogen, Carlsbad, Calif.). cDNA was synthesized from 1 µg total RNA using Superscript II reverse transcriptase (Invitrogen, Carlsbad, Calif.). qPCR primers were designed with qPrimerDepot. Measured mRNA levels were normalized to those of 18S ribosomal RNA and expressed as fold change relative to those of control group.

Western Blot Analysis

Liver whole-cell or nuclear extracts were prepared. Membranes were incubated with antibodies against FXR (Santa Cruz Biotechnology, Inc., Santa Cruz, Calif.), SREBP1 (BD Biosciences, San Jose, Calif.), and CIDEA (Abcam, Cambridge, Mass.). The signals obtained were normalized to β-ACTIN (Abcam) for whole cell extract and LAMIN A/C (Santa Cruz) for nuclear extracts.

16S rRNA Gene Sequencing of the Intestinal Microbiome

The bacteria in feces and cecum content were extracted using PowerSoil DNA Isolation Kit (Mo Bio laboratory, Inc., Carlsbad, Calif.). The PCR products (approximately 1000 bps) were purified using the Agencourt AMPure technology (Beckman Coulter, Brea, Calif.) as described in 454 Technical Bulletin #2011-002, Short Fragment Removal Procedure. After purification, the products were quantified by both Qubit (Lifetech, Carlsbad, Calif.) and qPCR, using the KAPA Biosystems Library Quantification Kit (KapaBiosystems, Woburn, Mass.), pooled based on molar amounts, run on a 1% agarose gel and extracted. After purification with a QIAquick PCR Purification kit (Qiagen, Valencia, Calif.), the quality and quantity were assessed using a DNA 7500LabChip on the Agilent 2100 Bioanalyzer (Agilent Technologies, Santa Clara, Calif.) and Qubit quantification. The sequencing was performed using a quarter PTP plate on a 454 Life Sciences Genome Sequencer FLX+ (Roche Diagnostics, Indianapolis, Ind.). 16S rRNA gene sequencing analysis was performed as previously described (Lozupone and Knight, *Appl. Environ. Microbiol.* 71:8228-8235, 2005). Weighted UniFrac analysis to assess changes in the bacterial abundance was performed on the Galaxy web-based platform (Blankenberg et al., *Bioinformatics* 26:1783-1785, 2010; Goecks et al., *Genome Biol.* 11: 126, 2010; Giardine et al., *Genome Res.* 15:1451-1455, 2005).

Metagenomic Data Analysis

After quality filtering and deduplication, each sample contained on average 11 thousand reads. The Mothur software package was used to preprocess the sequencing data and the RDP multi-classifier to assign each sequence to a taxonomic rank. Preprocessing consisted of filtering reads for an average quality of 20, removing duplicated sequences and splitting into samples by barcodes while allowing for one mismatch in the barcode. To account for differences in total reads per sample, classifications were converted to percent of total reads. This approach then permitted accurate comparisons within and between groups.

Metabolomics Analysis

Lipidomics analysis: For serum lipidomics analysis 25 µl serum were extracted by 4-fold cold chloroform:methanol (2:1) solution containing 2 µM LPC (17:0), PC (17:0), SM (17:0) and CER (17:0) (Avanti Polar Lipids, Alabaster, Ala.) as internal standards. The samples were vortexed for 30 s and then allowed to stand for 5 min at room temperature. The mixture was centrifuged at 13,000 rpm for 5 min and then the lower organic phase was collected and evaporated at room temperature under vacuum. The residue was dissolved in chloroform:methanol (1:1), followed by diluting with isopropanol:acetonitrile:$H_2O$ (2:1:1) containing 2 µM PC (17:0) prior to UPLC-MS analysis. For tissue lipidomics analysis, about 50 mg of accurately weighted tissues were homogenized with 700 µL methanol: $H_2O$ (4:3) solution and then extracted using 800 µL chloroform containing 2 µM LPC (17:0), SM (17:0) and CER (17:0) as internal standards. The homogenate was incubated at 37° C. for 20 min followed by centrifuged for 20 min at 13,000 rpm. The lower organic phase was transferred to a new tube and dried under vacuum. The residue was suspended with 100 chloroform: methanol (1:1) solution and then diluted with isopropanol: acetonitrile:$H_2O$ (2:1:1) solution containing 2 µM PC (17:0) before injection. For lipidomics discovery, samples were analyzed by UPLC-ESI-QTOF MS using a Water Acquity CSH 1.7 um C18 column (2.1×100 mm) under the following conditions: UPLC: A-acetonitrile/water (60/40), B-isopropanol/acetonitrile (90/10). Both A and B contained 10 mM Ammonium acetate and 0.1% formic acid. Gradient: initial 60% A to 57% A at 2 min, to 50% A at 2.1 min*, to 46% A at 12 min, to 30% A at 12.1 min*, to 1% A at 18 min before returning to initial conditions at 18.5 min with equilibration for 2 additional minutes (an *indicates ballistic gradient). Flow rate was 0.4 ml/min. Column temperature was maintained at 55° C. MS, same conditions as above, except run time was 18 min.

Global metabolomics analysis: urine samples were prepared by adding 20 µL of urine to 180 µL 50% aqueous acetonitrile (50:50 water/acetonitrile). Samples were vortexed for 5 min and centrifuged at 18000×g for 20 min at 4° C. to remove particulates and precipitated protein. The supernatant was transferred to an autosampler vial for analysis. 50 mg tissue samples were homogenized in 500 mL 50% aqueous acetonitrile containing 5 µM of chlorpropamide (internal standard). The samples were vortexed and centrifuged at 13,000 rpm for 20 min at 4° C. to remove particulates and precipitate protein. The supernatant was transferred to an autosampler vial for analysis. For metabolomics discovery, a 5 µl aliquot of supernatant samples was injected into the UPLC-ESI-QTOFMS system (Waters, Milford, Mass.) with a Waters Acquity BEH 1.7 um C18 (2.1×50 mm) column. The gradient mobile phase comprises 0.1% formic acid in water (A) and 0.1% formic acid in acetonitrile (B). The gradient was maintained at initial 95% A for 0.5 min, to 40% A at 4 min, and then to 1% A at 8 min. The column was flushed for 1 min, then equilibrated at initial conditions for 1.5 min. Flow rate was 0.5 ml/min. Column temperature was maintained at 60° C. Waters Synapt HDMS Q-TOF was operated in both positive and negative modes, scanning 50-850 amu, at a rate of 0.3 scans/sec. The following instrument conditions were used: capillary 3 kV, source temperature 120° C., sampling cove 30V, desolvation gas flow 850 L/h at 400° C. Biomarker identification and quantitation: Biomarkers were screened by analyzing ions in the loading scatter plot, and metabolomics databases (METLIN and Madison Metabolomics Consortium Database) were searched to find potential candidates. To confirm the identities of the putative markers, the authentic standards were compared with the metabolites based on MS/MS fragmentation pattern and retention time. Concentrations of the metabolites were determined by multiple reaction-monitoring mass spectrometry based on standard curves using authentic standards.

Data Processing and Multivariate Data Analysis

Chromatographic and spectral data were deconvoluted by MarkerLynx software (Waters). A multivariate data matrix containing information on sample identity, ion identity (retention time and m/z), and ion abundance was generated through centroiding, deisotoping, filtering, peak recognition, and integration. The intensity of each ion was calculated by normalizing the single ion counts vs. the total ion counts in the whole chromatogram. The data matrix was further exported into SIMCA-P software (Umetrics, Kinnelon, N.J.) and transformed by mean-centering and pareto scaling, a technique that increases the importance of low abundance ions without significant amplification of noise. Statistical models including principal components analysis (PCA), partial least squares-discriminant analysis (PLS-DA), and orthogonal projections to latent structures-discriminant analysis (OPLS-DA) were established to represent the major latent variables in the data matrix.

NMR-Based Metabolomics Experiments

Methanol, $K_2HPO_4$, $NaH_2PO_4$ (all in analytical grade), sodium 3-trimethylsilyl [2,2,3,3-d4] propionate (TSP-d4) and $D_2O$ (99.9% in D) were purchased from Sigma-Aldrich (St. Louis, Mo.). Phosphate buffer (0.1 M $K_2HPO_4$/$NaH_2PO_4$ and PH 7.4) was prepared with $K_2HPO$ and $NaH_2PO_4$ for their good solubility and low-temperature stability. Liver samples (~50 mg) were extracted three times with 0.6 mL 600 µL of precooled methanol-water mixture (2/1, v/v) using the PreCellys Tissue Homogenizer (Bertin Technologies, Rockville, Md.). After centrifugation at 11180×g for 10 min at 4° C., the combined supernatants were dried. Each of the aqueous extracts was separately reconstituted into 600 µL phosphate buffer containing 50% $D_2O$ and 0.005% TSP-d4 (chemical shift reference). Following centrifugation, 550 µL of each extract was transferred into a 5 mm NMR tube. Cecal content samples were directly extracted using an optimized procedure described previously (Wu et al., 2010). Briefly, samples (~50 mg) were mixed with 600 µL precooled phosphate buffer, vortexed for 30 s and subjected to three consecutive freeze-thaws followed by homogenization using the Precellys™ Tissue Homogenizer. After centrifugation (11,180×g, 4° C.) for 10 min, the supernatants (550 µL) were transferred into 5 mm NMR tubes for NMR analysis.

$^1$H NMR Spectroscopy $^1$H NMR spectra of aqueous liver and fecal extracts were recorded at 298 K on a Bruker Avance III 850 MHz spectrometer (operating at 850.23 MHz for 1H) equipped with a Bruker inverse cryogenic probe (Bruker Biospin, Germany). A typical one-dimensional NMR spectrum was acquired for each of all samples employing the first increment of NOESY pulse sequence (NOESYPR1D). To suppress the water signal, a weak continuous wave irradiation was applied to the water peak during recycle delay (2 s) and mixing time (100 ms). The 90° pulse length was adjusted to approximately 10 µs for each sample and 64 transients were collected into 32 k data points for each spectrum with spectral width of 20 ppm. To facilitate NMR signal assignments, a range of 2D NMR spectra were acquired and processed as described previously (Dai et al., 2010; Ding et al., 2009) for selected samples including $^1$H-$^1$H correlation spectroscopy (COSY), $^1$H-$^1$H total correlation spectroscopy (TOCSY), $^1$H-$^{13}$C heteronuclear single quantum correlation (HSQC), and $^1$H-$^{13}$C heteronuclear multiple bond correlation spectra (HMBC).

Spectral Data Processing and Multivariate Data Analysis

All free induction decays (FID) were multiplied by an exponential function with a 1 Hz line broadening factor prior to Fourier transformation. $^1$H NMR spectra were corrected manually for phase and baseline distortions and spectral region δ 0.5-9.5 was integrated into regions with equal width of 0.004 ppm (2.4 Hz) using AMIX software package (V3.8, Bruker-Biospin, Germany). Region δ 4.45-5.20 was discarded by imperfect water saturation. Regions δ 1.15-1.23 and δ 3.62-3.69 were also removed for ethanol contaminations in the cecal contents during mice dissection process. Each bucketed region was then normalized to the total sum of the spectral integrals to compensate for the overall concentration differences prior to statistical data analysis.

Multivariate data analysis was carried out with SIMCAP+ software (version 13.0, Umetrics, Sweden). Principal Component Analysis (PCA) was initially carried out on the NMR data to generate an overview and to assess data quality. Orthogonal projection to latent structures with discriminant analysis (OPLS-DA) was subsequently conducted on the NMR data. The OPLS-DA models were validated using a 7-fold cross validation method and the quality of the model was described by the parameters R2X and Q2 values. To facilitate interpretation of the results, back-transformation (Cloarec et al., *Anal. Chem.* 77:517-526, 2005) of the loadings generated from the OPLS-DA was performed prior to generating the loadings plots, which were color-coded with the Pearson linear correlation coefficients of variables (or metabolites) using an in-house developed script for MATLAB (The Mathworks Inc.; Natwick, Mass.). In this study, a cutoff value of |r|>0.811 (r>0.755 and r<−0.755) was chosen for correlation coefficient as significant based on the discrimination significance (p<0.05).

Bile Salt Hydrolase Activity

Fecal proteins were prepared from feces samples (0.5 g) in pH 7.4 phosphate buffered saline (PBS, 5.0 mL) using sonication. Bile salt hydrolase (BSH) activity was measured based on the generation of CDCA from TCDCA in the feces. Briefly, incubation was carried out in 3 mM sodium acetate buffer, pH 5.2, containing 0.1 mg/ml fecal protein and 50 µM TCDCA-d5 in a final volume of 200 µL. After a 20 min incubation at 37° C., the reaction was stopped by plunging the samples into dry ice. 100 µL of acetonitrile was directly added to the reaction mix. After centrifuging at 14,000×g for 20 min, 5 µL of the supernatant was transferred to an auto sampler vial subjected to analysis by a UPLC system coupled with a XEVO triple quadrupole tandem mass spectrometer (Waters Corp., Milford, Mass.).

Mitochondrial Isolation and Functional Studies

For intestinal mitochondria, the mucosa of ileum was gently scraped, washed 2× with PBS, minced in ice-cold mitochondrial homogenization buffer (225 mM mannitol, 75 mM sucrose, 5 mM MOPS, 0.5 mM EGTA and 2 mM taurine (pH 7.25)) containing 0.2% BSA, and homogenized in a loose fitting homogenizer. Homogenates were centrifuged at 500×g for 10 min at 4° C. The supernatant was then centrifuged at 10,000×g for 10 min at 4° C. The final mitochondrial pellet was resuspended in mitochondrial isolation buffer containing 0.2% BSA at a concentration of 0.5 mg/ml before functional assessment.

The oxygen consumption of isolated mitochondria was measured in a chamber connected to a Clark-type $O_2$ electrode (Instech) and $O_2$ monitor (Model 5300, YSI Inc) at 25° C. Mitochondria were incubated in respiration buffer (120 mM KCl, 5 mM MOPS, 0.1 mM EGTA, 5 mM $KH_2PO_4$ and 0.2% BSA) with substrates for either complex I (5 mM glutamate and 5 mM malate), or complex II (5 mM succinate and 1 µM rotenone). State 3 (maximal) respiration activity was measured after addition of 1 mM ADP. ADP independent respiration activity (State 4) was monitored after addition of 2 µM oligomycin. The respiratory control ratio was determined by the state 3/state 4 respiration rates.

Histological Analysis

Hematoxylin and eosin (H&E) staining were performed on formalin fixed paraffin embedded sections using a standard protocol. Oil red 0 staining was performed on frozen liver sections using a standard protocol. At least three discontinuous liver sections were evaluated for each mouse.

Triglycerides Content Quantification

Hepatic lipids were extracted using a 2:1 chloroform-methanol solution. Liver triglycerides were measured with a triglyceride colorimetric assay kit, according to the manufacturer's recommendation (Bioassay Systems, Hayward, Calif.).

Cell Culture

Caco-2 (ATCC™ HTB-37™) cells were induced to differentiate following the method as described previously (Ferraretto et al., *Anticancer Res.* 27:3919-3925, 2007). The differentiated Caco-2 cells were incubated for 8 hours with DMEM media with 1% fetal bovine serum, and then exposed to Gly-MCA/CDCA/GW4064 for 24 hours. RNA was extracted from frozen intestine using TRIzol reagent (Invitrogen). cDNA was synthesized from 1 µg total RNA using Superscript II reverse transcriptase (Invitrogen).

Gly-MCA Hydroxylation by Gut Bacterial

Fecal proteins were prepared from the fecal sample (0.5 g) in pH 7.4 PBS (5.0 ml) using sonication. Incubation was carried out in 3 mM sodium acetate buffer, pH 5.2, containing 0.1 mg/ml fecal protein and 50 µM Gly-MCA or T-β-MCA in a final volume of 200 ml. After a 20-min incubation at 37° C., the samples were plunged into dry ice to stop the reaction. 100 of µL methanol was directly added to the 100 ml reaction mixture. After centrifuging at 14,000 g for 20 min, 5 ml of the supernatant was transferred to an autosampler vial subjected to analysis by a UPLC system coupled with a XEVO triple quadrupole tandem mass spectrometer (Waters Corp., Milford, Mass.).

Animal Studies

High fat diet (HFD) (60% kcal consisting of fat) was purchased from Bioserv. Inc. Gly-MCA was custom synthesized.

Bacon-flavored dough pills were produced as described (Walker et al., *Toxicol. Appl. Pharmacol.* 260:65-69, 2012) for oral administration of Gly-MCA (0.25 mg Gly-MCA/pill). Mice were trained to eat the dough pills prior to the study.

Male wild-type (WT) C57BL/6N mice, 6- to 8-weeks-old, were fed a HFD (Bio-Serv, Frenchtown, N.J.; 60 kcal % fat) from the age of 6 weeks and were orally administered with vehicle (control pills) or Gly-MCA (0.25 mg/pill/day, 10 mg/kg). Mice were housed individually in their home cages. Cumulative food intake and $TEE_{bal}$ were measured for 1 week in vehicle and Gly-MCA-treated mice from 6 to 7 weeks of HFD. $TEE_{bal}$ was measured as previously described (Ravussin et al., *Int. J. Obesity* 37:399-403, 2013).

All animal studies were performed in accordance with the Institute of Laboratory Animal Resources guidelines and approved by the NCI Animal Care and Use Committee.

Metabolic Assays

For the glucose tolerance test (GTT), mice were fasted for 16 h, blood was drawn, and mice were injected intraperitoneally (i.p.) with 1 g/kg glucose. For the insulin tolerance test (ITT), mice were fasted 4 h, blood was drawn, and then were injected with insulin (Eli Lilly, Washington, D.C.), by i.p. at a dose of 1 U/kg body weight. Blood samples were taken from the tail at 15, 30, 60, and 90 min after injection, and glucose measured using a Glucometer (Bayer, Pittsburgh, Pa.).

Example 1

This example demonstrates that tauro-β-muricholic (TβMCA) acid antagonized FXR activation by taurocholic acid (TCA) in primary mouse hepatocytes.

Primary hepatocytes from $Fxr^{+/+}$ and $Fxr^{-/-}$ mice were transfected with PGL4-Shp-TK firefly luciferase construct and the control plasmid phRL-SV40. After 24 h, the cells were treated with 100 µM taurocholic acid (TCA), TβMCA, or TβMCA with TCA. The cells were lysed, and luciferase activities measured as describe herein. The results are depicted in FIG. 1.

Figure 1:
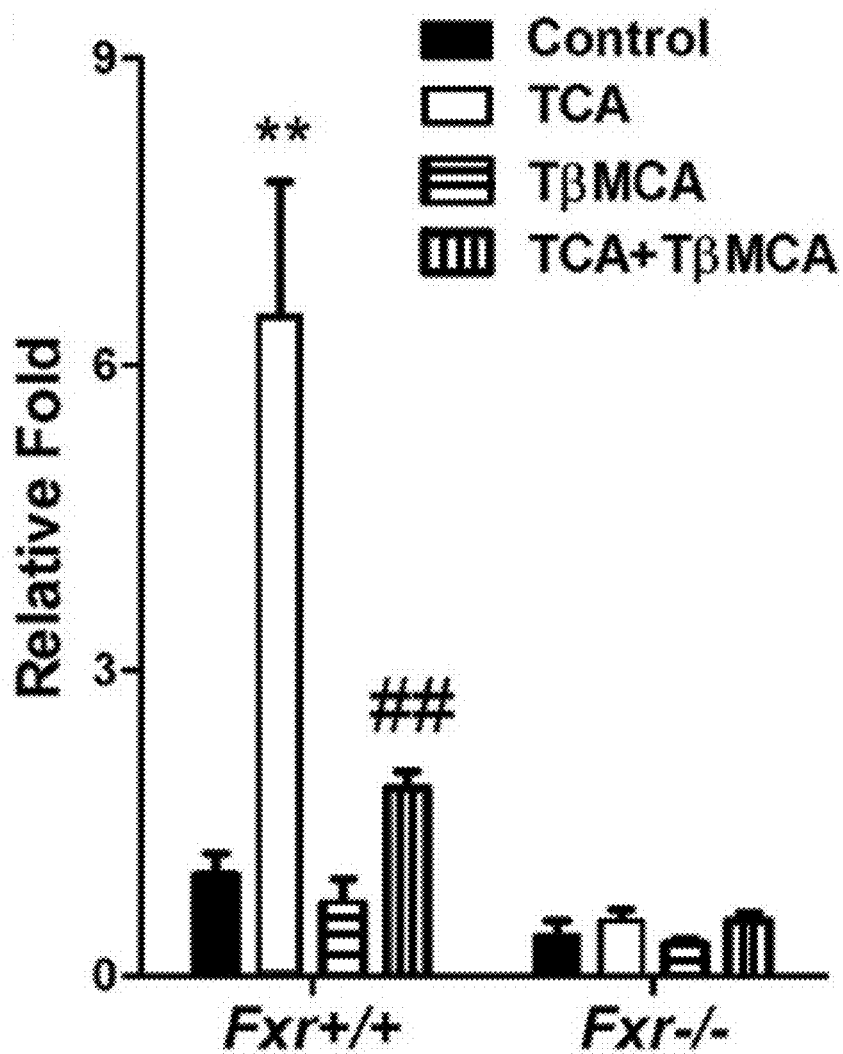
FIG. 1 depicts results of luciferase assays showing that tauro-β-muricholic acid (TβMCA) antagonizes farnesoid X receptor (FXR) activation by the FXR agonist taurocholic acid (TCA) in cultured primary hepatocytes.

As is apparent from the results depicted in FIG. 1, TβMCA antagonized FXR activation by TCA in primary hepatocytes from $Fxr^{+/+}$ mice, but not from $Fxr^{-/-}$ mice.

Example 2

This example demonstrates that TβMCA antagonized FXR activation by TCA in Caco-2 cells.

Caco-2 cells were transfected with PGL4-Shp-TK firefly luciferase construct, the control plasmid phRL-SV40, and human FXR and human ASBT expression plasmids. After 24 h, the cells were treated with 100 µM TCA, TβMCA, or TβMCA with 100 µL 100 µM TCA. The cells were lysed, and luciferase activities measured as describe herein. The results are depicted in FIG. 2.

Figure 2:
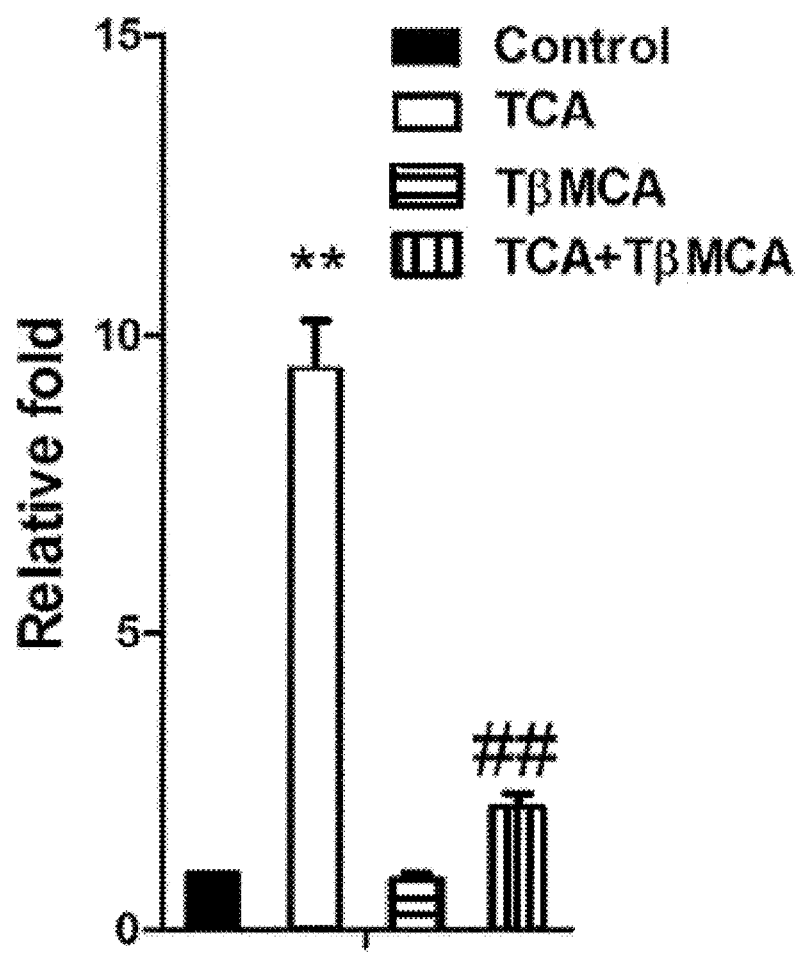
FIG. 2 depicts results of luciferase assays showing that tauro-β-muricholic acid (TβMCA) antagonizes FXR activation by the FXR agonist taurocholic acid (TCA) in Caco2 cells.

As is apparent from the results depicted in FIG. 2, TβMCA antagonized FXR activation by TCA in Caco-2 cells.

Example 3

This example demonstrates that ATP levels in mouse ileum mucosa were markedly elevated in $Fxr^{\Delta IE}$ mice as compared to $Fxr^{fl/fl}$ mice after 14 weeks on a high fat diet.

Two separate groups of $Fxr^{fl/fl}$ mice and $Fxr^{\Delta IE}$ mice were kept on a high fat diet for 14 weeks. ATP levels in the ileum mucosa of both groups of mice were determined as described herein. The results are depicted in FIG. 3.

Figure 3:
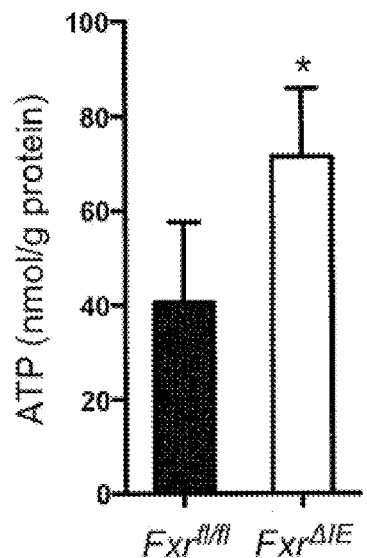
FIG. 3 illustrates ATP levels in the ileum mucosa of $Fxr^{fl/fl}$ mice and $Fxr^{\Delta IE}$ mice that were kept on a high fat diet for 8 weeks.

As is apparent from the results depicted in FIG. 3, ATP levels in the ileum mucosa of $Fxr^{\Delta IE}$ mice, which do not express farnesoid X receptor (FXR) in the intestine, were markedly elevated as compared with ATP levels in the ileum mucosa of control $Fxr^{fl/fl}$ mice that express intestinal FXR. These results indicate increased energy expenditure occurred in the small intestine in the absence of the nuclear receptor FXR.

Example 4

This example demonstrates that glycine-β-muricholic acid (Gly-MCA) is an FXR antagonist.

Figure 4:
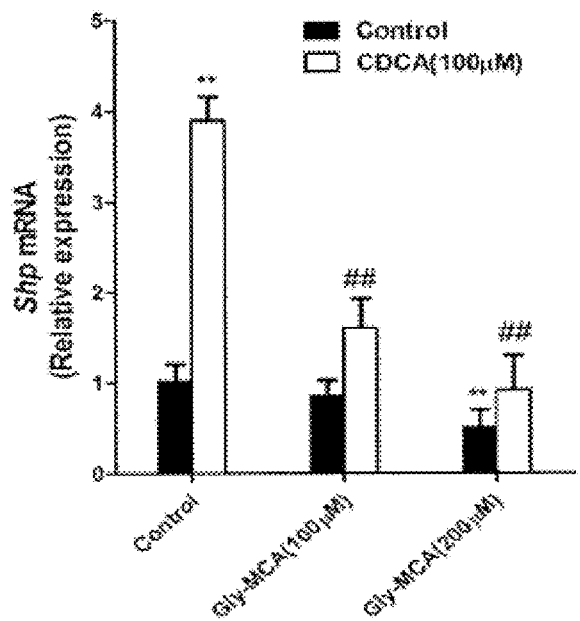
FIG. 4 illustrates the blocking of induction of Shp mRNA with chenodeoxycholic acid by glycine-β-muricholic acid.
Figure 5:
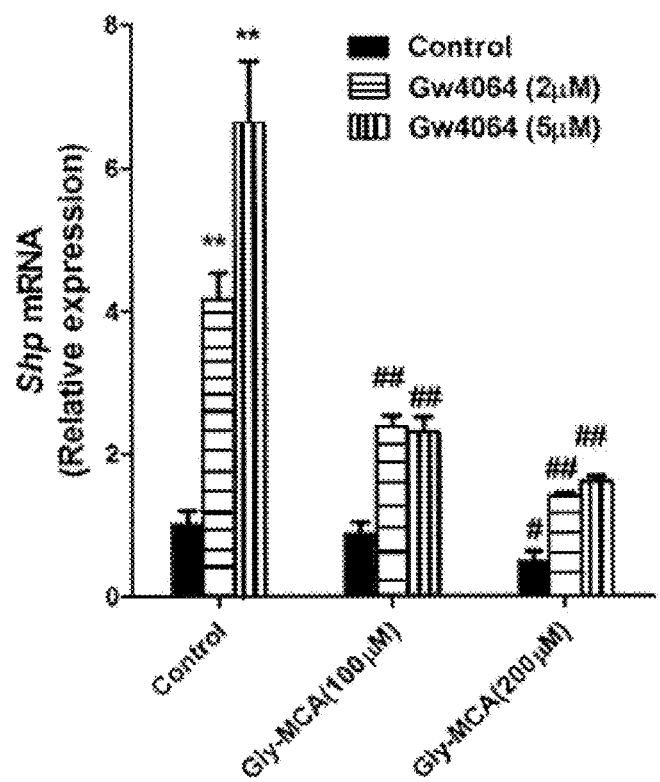
FIG. 5 illustrates the blocking of induction of Shp mRNA with GW4064 by glycine-β-muricholic acid.
Figure 6:
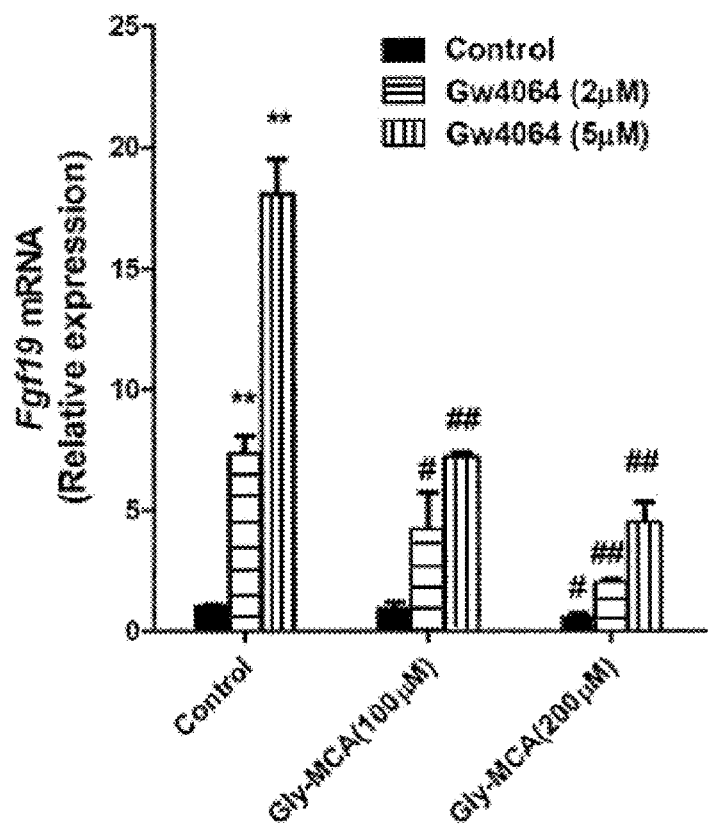
FIG. 6 illustrates the blocking of induction of Fgf19 mRNA with GW4064 by glycine-β-muricholic acid.
Figure 7:
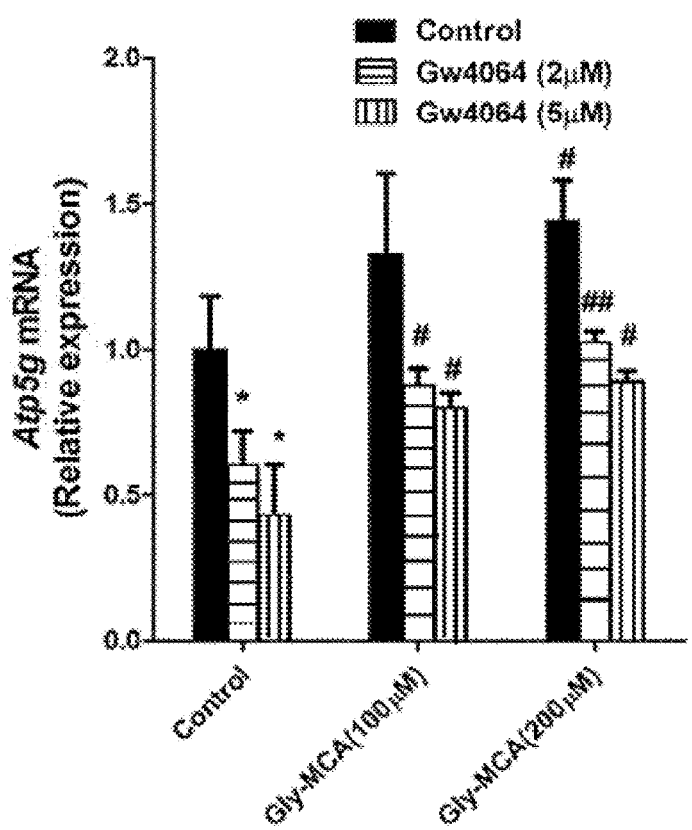
FIG. 7 illustrates the reversal of Atp5g mRNA inhibition by GW4064 by glycine-β-muricholic acid.

Mice make TβMCA in the liver while humans preferentially make Gly-MCA. Thus, it was of interest to determine whether Gly-MCA was also an FXR antagonist. Chenodeoxycholic acid (CDCA), an FXR agonist at a dose of 100 µM, increased expression of the Fxr target gene Shp mRNA four-fold and the induction of Shp mRNA with CDCA was inhibited by Gly-MCA in a dose dependent manner (FIG. 4). Gw4064, a synthetic FXR agonist, induced expression of the FXR target genes Shp and Fgf19 at both 2 µM and 5 µM concentrations, and induction of both genes was blocked by Gly-MCA ☐ in a dose dependent manner (FIGS. 5 and 6). In addition, Gw4064 treatment inhibited Atp5g mRNA expression and Gly-MCA reversed this inhibition (FIG. 7). These data indicate that Gly-MCA, produced in humans, is an FXR antagonist similar to TβMCA.

Example 5

This example demonstrates the effect of tempol on body mass of high-fat diet-treated $Fxr^{fl/fl}$ and $Fxr^{\Delta IE}$ mice.

Figure 11:
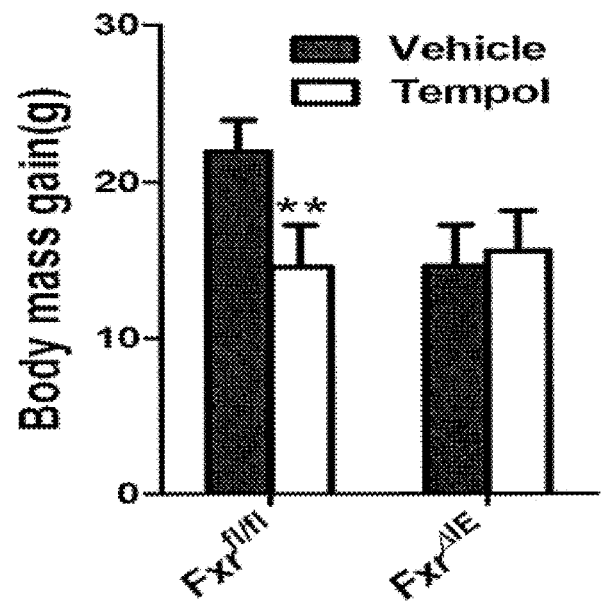
FIG. 11 illustrates the body mass gain for $Fxr^{fl/fl}$ and $Fxr^{\Delta IE}$ mice treated with vehicle or tempol after 10 weeks of a high fat diet.

Vehicle and tempol-treated $Fxr^{fl/fl}$ and $Fxr^{\Delta IE}$ mice were maintained on a high-fat diet for 10 weeks. FIG. 11 depicts the body mass gain in grams for vehicle and tempol-treated $Fxr^{fl/fl}$ and $Fxr^{\Delta IE}$ mice after 10 weeks of a high-fat diet feeding.

As is apparent from the results depicted in FIG. 11, tempol treatment of $Fxr^{fl/fl}$ mice resulted in a weight gain that was approximately 65% less of the weight gain exhibited by vehicle treated mice. Tempol treatment of $Fxr^{\Delta IE}$ mice, which are intestinal-specific Fxr-null mice, resulted in an insignificant difference in weight gain, thereby implicating intestinal FXR in mediating the lower weight gain by tempol of mice fed a high-fat diet.

Example 6

This example demonstrates the role of intestinal FXR in lipid and glucose metabolism.

Male $Fxr^{fl/fl}$ and $Fxr^{\Delta IE}$ mice were fed a high fat diet revealing that $Fxr^{\Delta IE}$ mice were resistant to high fat diet-induced obesity. The fat mass in grams and as a percentage of body mass was measured in non-anesthetized mice using an Echo 3-in-1 NMR analyzer (Echo Medical Systems, Houston, Tex.), and the results depicted in FIGS. 12A and B. The results show that fat mass and the ratio of fat and body mass of $Fxr^{fl/fl}$ mice were higher than for $Fxr^{\Delta IE}$ mice. The glucose tolerance test (GTT) revealed that $Fxr^{\Delta IE}$ mice had improved glucose intolerance compared to $Fxr^{fl/fl}$ mice, which is depicted in FIG. 13, which shows the area under the curve for blood glucose (in mg/dL) as a function of time. The insulin tolerance test (ITT), which is depicted in FIG. 14, demonstrated that the insulin sensitivity in $Fxr^{\Delta IE}$ mice was significantly increased as compared to $Fxr^{fl/fl}$ mice. In addition, fasted serum insulin levels and the HOMA in $Fxr^{\Delta IE}$ mice was significantly increased as compared to $Fxr^{fl/fl}$ mice, while fasted glucose was approximately the same in both groups of mice, as depicted in FIGS. 15A-C.

Example 7

This example demonstrates that tempol affects bile acid homeostasis via inhibition of the genus *Lactobacillus*.

Significant phylum-level shifts from Firmicutes to Bacteroidetes in the gut microbiome composition were observed in mouse cecum following 5 days of tempol treatment by gavage (250 mg/kg) of mice on normal chow diet. Heat map diagrams of 16S rRNA sequencing indicated that tempol treatment dramatically decreased the family Lactobacillacieae. It was found that tempol treatment robustly reduced the genus *Lactobacillus*. Similar to the results of acute treatment via gavage, qPCR analysis of suspected fecal microbes obtained from mice on a high fat diet revealed total bacteria remain unchanged between vehicle and tempol treated mice, while tempol treatment cause a shift from Firmicutes to Bacteroidetes, as depicted in FIGS. 16A and B. These results indicate that the effects of tempol on the gut microbiome are independent of diet and obesity conditions. Furthermore, the genus *Lactobacillus* of the Lactobacillaceae was decreased, coincident with significant downregulation of bile salt hydrolase (BSH) enzymatic activity in the feces, as depicted in FIGS. 17A and B. Bile salt hydrolase (BSH) deconjugates taurine-conjugated bile acids produced in the liver to free bile acids.

These results indicate that tempol affects bile acid homeostasis via inhibition of the genus *Lactobacillus*.

Example 8

This example demonstrates the results of a human FXR competition assay using the synthetic agonist Gw4064 and varied doses of TUDCA, TWMCA, TβMCA, TαMCA. Results were normalized to *Renilla* expression.

HEK293T cells were co-transfected with: 1) a chimeric receptor construct in which the carboxy terminal portions of human FXR (containing the native ligand-binding domain and AF2 transactivation domain) was fused to an amino terminal GAL4 DNA-binding domain under regulatory control of the constitutively active SV40 promoter; 2) a firefly luciferase reporter plasmid driven by the UAS GAL4 DNA response element; and, 3) a *Renilla* luciferase reporter gene (pRL-luciferase; Promega; Madison, Wis.) as a transfection efficiency control. Luciferase detection was conducted using the Dual Luciferase Reporter Assay kit (Promega Corp., Madison, Wis.) and a Tecan GeniosPro luminescent plate reader (Research Triangle Park, N.C.). The results are illustrated in FIGS. 18A-D.

As is apparent from the results illustrated in FIG. 18, all of the bile acid conjugates TUDCA, TWMCA, TβMCA, and TαMCA inhibited FXR in the presence of the synthetic agonist Gw4064.

Example 9

This example demonstrates that changes in the gut microbiota brought about by tempol are correlated with NAFLD.

High-fat diet (HFD) is extensively used as a mouse model for NAFLD. The antioxidant tempol selectively modulates the gut microbiota composition and metabolism under normal diet conditions (Li et al., *Nat. Commun.* 4: 2384, 2013). In an effort to determine whether tempol modifies the gut microbiome in the HFD-induced NAFLD model, 16S rRNA gene sequencing analysis was carried out. Weighted UniFrac™ analysis showed distinct clustering of cecal communities isolated from vehicle and tempol-treated groups on a HFD for 12 weeks. Principal coordinate 1 (PC1) explains 56.08% of the variation, indicating that tempol had a stronger effect on microbiota composition than vehicle in mice on a HFD for 12 weeks (FIG. 19A). The separation of samples in the principal components analysis plot reflects abundance differences in significantly decreased Firmicutes and markedly increased Proteobacteria. The genus *Desulfovibrio* was identified as a major contributor of the increased Proteobacteria (FIG. 19B), which was found to be significantly lower in obese subjects (Karlsson et al., *Obesity* 20:2257-2261, 2012). A dramatic increase in the genus *Roseburia* was observed (FIG. 19C), which is negatively correlated with body weight in dogs (Handi et al., *FEMS Microbiol. Ecol.* 84332-343, 2013). The genus *Clostridium sensu stricto* and *Lactobacillus* levels were also significantly decreased in tempol-treated mice, whereas the levels of genus *Bacteroides* and *Streptococcus* remained similar (FIG. 19D-G).

To identify gut microbiota related markers in urine, ultra-performance liquid chromatography coupled with electrospray ionization quadrupole time-of-flight mass spectrometry (UPLC-ESI-QTOFMS)-based metabolomics analysis was employed. PCA modeling of UPLC-ESI-QTOFMS negative mode data from mouse urine demonstrated clear discrimination between the tempol and the control group (FIG. 20A). Loadings scatter plot analysis revealed that two compounds, p-cresol sulfate (m/s 187.0060 with retention time 2.61 min) and p-cresol glucuronide (m/s 283.0812 with retention time 3.04 min) were significantly reduced in urine of the tempol-treated group (FIGS. 20B and C). The identities of these compounds were confirmed by MS/MS analysis (FIGS. 20D and E). These results indicated that tempol remodeled the gut microbiota composition and altered gut microbiota-related metabolism markers in mice on HFD for 14 weeks. Similar to the results of the tempol treatment model to specifically modulate the gut flora, metabolomics analysis revealed that the urinary levels of p-cresol sulfate and p-cresol glucuronide were almost absent in antibiotic-treated mice on a HFD for 14 weeks (FIGS. 21A-C). Following the change of the gut microbiota composition and related metabolites, liver histology indicated a significant reduction in hepatic lipid droplets in tempol-treated mice on a HFD for 16 weeks and antibiotic-treated mice on a HFD for 7 weeks (FIGS. 22A and B, and FIG. 23A). Tempol treatment and antibiotic treatment, which also changes the gut microbiota composition, decreased liver weights and liver/body mass ratios, respectively (FIGS. 22C and D, FIGS. 23A and B). Hepatic triglyceride (TG) contents were decreased to approximately 50% and 35% in mice treated with antibiotic and tempol, respectively (FIG. 22E and FIG. 23D).

Example 10

This example demonstrates that gut microbiota modifies bile acid metabolism and affects FXR signaling.

The gut microbiota is tightly associated with bile acid metabolism. UPLC-ESI-QTOFMS-based metabolomics analysis was adopted to determine bile acid composition and levels of bile acid metabolites in the intestine. Scores scatter plot of a PCA model of the UPLC-ESI-QTOFMS negative mode data from mouse ileum indicated distinct metabolic profiles between the vehicle and antibiotic groups (FIG. 24A). The top enriched metabolite, TβMCA (m/z 514.2871, retention time=6.64 min), was increased in the antibiotic-treated mice on a HFD for 7 weeks as revealed in the loading scatter plot (FIG. 24B) according to previous methods; this increase was similar to what was observed with tempol treatment (Li et al., *J. Proteome Res.*, 12:1369-1376, 2013). Analysis of ileum bile acid composition revealed that the levels of taurine-conjugated bile acid TβMCA were significantly increased after antibiotic treatment (FIG. 25A). Similar results were obtained from tempol-treated mice on a HFD for 16 weeks (FIG. 25B). The gut microbiota can modify bile acid composition by microbial enzymatic activities. The activity of bile salt hydrolase (BSH), a bacterial enzyme that hydrolyzes taurine-conjugated bile acids to free bile acids, was greatly reduced in the antibiotic-treated mice on a HFD for 7 weeks (FIG. 26A). This likely accounts for the most significantly enriched bile acid in the ileum of antibiotic- and tempol-treated mice on a HFD that was TβMCA, an FXR antagonist (Li et al., *J. Proteome Res.*, 12:1369-1376, 2013; Sayin et al., *Cell Metab.* 225-235, 2013). Western blot and qPCR analysis indicated that 12 weeks of HFD treatment significantly induced FXR protein levels (FIG. 26B) and FXR signaling in the ileum as revealed by increases in mRNAs from the FXR target genes, small heterodimer partner (Shp) and fibroblast growth factor 15 (Fgf15) mRNAs (FIG. 26 C). Conversely, antibiotic treatment decreased Shp and Fgf15 mRNAs indicating that FXR signaling was inhibited in the ileum (FIG. 26D). The question arose as to whether TβMCA inhibited FXR signaling in mice on HFD treatment in vivo. TβMCA treatment significantly blunted the Shp and Fgf15 induction by the FXR agonist TCA in the ileum of mice treated with antibiotic on a HFD for three days (FIG. 26E). These results indicated that both antibiotic and tempol treatments regulated bile acid composition, mainly by increasing TβMCA as a result of lower bacterial BSH activity, which inhibited FXR signaling in the ileum of HFD-fed mice.

Example 11

This example demonstrates that intestine-specific Fxr disruption reduces hepatic lipid accumulation in high-fat diet fed mice.

To further clarify the role of intestinal FXR in the development of NAFLD, intestine-specific Fxr-null (Fxr$^{\Delta IE}$) mice were treated with HFD for 14 weeks. H&E staining and Oil red 0 staining of liver sections showed a significant decrease in lipid accumulation in livers of Fxr$^{\Delta IE}$ mice compared to wild-type (Fxr$^{fl/fl}$) mice (FIGS. 27A and B). Fxr$^{\Delta IE}$ mice displayed significantly reduced liver weight and ratio of liver weight (FIG. 27C). This change in liver weight was largely due to hepatic triglyceride (TG) levels that were 50% lower in Fxr$^{\Delta IE}$ mice compared to Fxr$^{fl/fl}$ mice on a HFD for 14 weeks (FIG. 27D). Mechanistic studies revealed that the expression of mitochondrial electron transport chain (ETC) complex II related genes such as succinate dehydrogenase complex, subunit D, integral membrane protein (Sdhd), complex III related gene such as cytochrome c1 (Cyc1), complex IV related gene such as mitochondrially-encoded cytochrome c oxidase II (mt-Co2), cytochrome c oxidase subunit IV isoform 1 (Cox4i1), cytochrome c oxidase subunit Va (Cox5a), ATP synthase, H+ transporting, mitochondrial F0 complex, subunit C1 (subunit 9) (Atp5g) and ATP synthase, H+ transporting, mitochondrial F0 complex, subunit D (Atp5h), were elevated in the ileum epithelium of Fxr$^{\Delta IE}$ mice (FIG. 28A). Similar results were obtained from antibiotic-treated mice (FIG. 28B). Subsequently, there was an approximately 70% increased activity of complex II and no significant elevation in activity of complex I in the ileum mitochondria of Fxr$^{\Delta IE}$ mice compared to Fxr$^{fl/fl}$ mice (FIG. 28C). Ileum ATP levels in Fxr$^{\Delta IE}$ mice were also significantly higher than in Fxr$^{fl/fl}$ mice (FIG. 28D). Free fatty acids are closely associated with the development of hepatic steatosis (Donnelly et al., *J. Clin. Invest.* 115:1343-1351, 20052005). However, serum lipidomics revealed that a subset of species of free fatty acids were at similar levels in vehicle- and tempol-treated Fxr$^{\Delta IE}$ mice and Fxr$^{fl/fl}$ mice (FIG. 29A). LC-MS/MS quantitation confirmed that ileum C16:0, C18:0, C20:0, C22:0, C24:0 and C24:1 ceramide levels were significantly reduced in antibiotic-treated mice on a HFD for 7 weeks (FIG. 29B). Accordingly, serum C16:0, C18:0, C20:0, C24:0 and C24:1 ceramide levels in antibiotic-treated mice were also significantly lower than in vehicle-treated mice (FIG. 29C). The identity of each ceramide was confirmed by LC-MS fragmentography (FIG. 30A-G). Further, intestinal mRNAs encoding de novo ceramide synthesis-related genes, such as serine palmitoyl-transferase, long chain base subunit 3 (Sptlc3), ceramide synthase 4 (Cers4), degenerative spermatocyte homolog 1 (Degs1), and sphingomyelin phosphodiesterase 3 (Smpd3) waned significantly in $Fxr^{\Delta IE}$ mice and antibiotic-treated mice (FIGS. 29C and D). Ceramide synthase 2 (Cers2) mRNA levels were significantly decreased in antibiotic-treated mice, and have a reduced trend (P=0.06) in $Fxr^{\Delta IE}$ mice. The expression of genes involved in ceramide catabolism such as sphingomyelin synthase 1 and 2 (Sgms1 and Sgms2), and alkaline ceramidase 1 and 3 (Acer1 and Acer3) remained similar in $Fxr^{\Delta IE}$ mice and antibiotic-treated mice (FIGS. 29C and D)

Example 12

This example demonstrates that ceramide regulates the SREBP1c-CIDEA pathway in the liver.

To establish a causal relationship between the decrease in ceramide levels and improvement of NAFLD, mice on a HFD were treated with antibiotics for a short duration. Three days of antibiotic treatment did not decrease triglyceride content in the liver (FIG. 31A). Subsequently, the FXR signaling pathway was inhibited as revealed by decreased expression of the FXR target gene Shp and Fgf15 mRNAs (FIG. 31B). As early as 3 days after antibiotic treatment, ceramide levels in the ileum of antibiotic-treated mice were significantly decreased (FIG. 31C). These results indicated ceramide might be the cause rather than the result of the development of NAFLD and a a biomarker to monitor NAFLD. The contribution of ceramide to NAFLD was further evaluated in cultured primary mouse hepatocytes. Ceramide treatment induced a significantly increased triglyceride contents in primary hepatocytes in a dose-dependent manner (FIG. 31D). To elucidate the mechanisms by which ceramide leads to hepatic steatosis, the expression of the genes involved in hepatic lipogenesis and fatty acid oxidation were measured. Fatty acid synthesis-related genes such as sterol response element-binding protein 1c (Srebp1c), DNA fragmentation factor-alpha-like effector a (Cidea), elongation of very-long-chain fatty acids protein 6 (Elovl6) and TG formulation related genes such as diacyl-glycerol O-acyltransferase 2 (Dgat2) were significantly upregulated by ceramide in primary hepatocytes (FIG. 31E). In contrast, the expression of genes involved in fatty acid β-oxidation such as carnitine palmitoyltransferase 1 (Cpt1), acyl-coenzyme A oxidase 1 (Acox1), enoyl-coenzyme A, hydratase/3-hydroxyacyl coenzyme A dehydrogenase (Ehhadh), and acetyl-coenzyme A acyltransferase 1A (Acaa1a) were not affected by ceramide treatment (FIG. 31E). In agreement with the mRNA results, ceramide exposure at 2 μM and 10 μM significantly induced the protein levels of the mature nuclear form of SREBP1-N and the SREBP1-N target gene protein CIDEA (FIGS. 31F and G). In vivo, mRNAs encoded by the hepatic fatty acid synthesis related genes Srebp1c, Cidea, fatty acid synthase (Fasn), and Elovl6 were decreased in antibiotic-treated mice compared to vehicle-treated mice, and $Fxr^{\Delta IE}$ compared to $Fxr^{fl/fl}$ mice (FIGS. 32A and B). The expression of genes involved in fatty acid remained at similar levels in antibiotic-treated mice compared to vehicle-treated mice, and $Fxr^{\Delta IE}$ compared to $Fxr^{fl/fl}$ mice (FIGS. 32C and D). Western blot analysis further revealed that the protein levels of the mature nuclear form of SREBP1-N and CIDEA were significantly downregulated in livers of antibiotic-treated mice on a HFD for 7 weeks (FIGS. 32E and F). The rate limiting enzyme cholesterol 7α-hydroxylase (CYP7A1) initiates the classic pathway for bile acid synthesis and plays an important role in regulating lipid metabolism. Cyp7a1 mRNA levels were marginally induced in antibiotic-treated mice, but not in tempol-treated mice (FIGS. 32G and H). In addition, inflammation-related genes such as toll-like receptor 2 (Tlr2), toll-like receptor 4 (Tlr4), toll-like receptor 9 (Tlr9) and tumor necrosis factor α (Tnfα), were comparable in antibiotic- and tempol-mice (FIGS. 32I and J). The present findings revealed that inhibition of ceramide metabolism might be a major contributing factor to improve HFD-induced NAFLD development in antibiotic-treated mice.

Example 13

This example demonstrates that inhibition of intestinal FXR is required for gut microbiome-mediated progression of NAFLD.

$Fxr^{\Delta IE}$ mice were employed to determine the role of intestinal FXR in the progression of the NAFLD. Liver histology revealed that antibiotic and tempol treatment decreased hepatic lipid droplets in $Fxr^{fl/fl}$ mice on a HFD for 14 and 16 weeks, respectively; no changes in hepatic lipid were observed in $Fxr^{\Delta IE}$ mice with these treatments (FIGS. 33A and B and FIGS. 34A and B). The liver weights and liver/body mass ratios of antibiotic- and tempol-treated $Fxr^{fl/fl}$ mice were significantly reduced, whereas the liver weights and liver/body mass ratios were similar in $Fxr^{\Delta IE}$ and $Fxr^{fl/fl}$ mice (FIGS. 33C and D, FIGS. 34C and D). Hepatic triglyceride content analysis confirmed that antibiotic and tempol treatment did not alleviate hepatic steatosis in $Fxr^{\Delta IE}$ mice (FIG. 33E and FIG. 34E). Ileum and serum C16:0, C18:0, C20:0, C22:0, C24:0 and C24:1 ceramide levels were significantly decreased in $Fxr^{\Delta IE}$ mice and tempol-treated $Fxr^{fl/fl}$ mice, but not in $Fxr^{\Delta IE}$ mice (FIGS. 33F and G). In $Fxr^{\Delta IE}$ mice, hepatic fatty acid synthesis related genes such as Srebp1c, Cidea, Fasn, and Elovl6 remained unchanged between vehicle-treated and antibiotic-treated mice (FIG. 34F). Further, the protein levels of the mature nuclear form of SREBP1 and CIDEA proteins were significantly reduced in the liver of tempol-treated mice, whereas no decrease was noted in $Fxr^{\Delta IE}$ mice treated with tempol (FIGS. 34G and H). The present findings revealed that inhibition of intestinal FXR mediates the amelioration of NAFLD caused by antibiotic and tempol treatments.

Example 14

This example demonstrates the systemic responses of mice on a high-fat diet, to tempol and antibiotic treatment.

A total of 53 metabolites involved in the metabolism of amino acids, carbohydrates and nucleotides were identified by $^1$H NMR. 1D $^1$H NMR spectra of the cecal contents are dominated by short chain fatty acids (SCFAs), nucleotides, oligosaccharides and some amino acids. Glycogen, glucose, amino acids and nucleotides are the dominant metabolites observed in the $^1$H NMR spectra of liver.

In order to obtain the metabolic variations associated with different biological sample groups, pair-wise OPLS-DA was performed between data obtained from cecal contents or liver of mice after tempol or antibiotic treatment. The quality of these models was further validated by evaluation with CV-ANOVA (p<0.05) and permutation test (200 tests) for the OPLS-DA and PLS-DA models. Compared with the vehicle-treated wild-type mice, tempol treatment significantly decreased the levels of SCFAs (acetate, propionate, and butyrate) but significantly elevated the levels of oligosaccharides and glucose in the cecal contents. Similar changes in SCFAs and oligosaccharides were also observed from the cecal contents of the antibiotic-treated wild type mice compared to those from the respective controls. However, no significant differences in the levels of SCFAs and oligosaccharides were observed in the cecal contents between tempol-treated and vehicle-treated $Fxr^{\Delta IE}$ mice.

Tempol treatment significantly decreased the levels of lipid and unsaturated fatty acid (UFA) in the livers, whereas tempol treatment significantly elevated the levels of glucose, glycogen, bile acids and a range of nucleotide metabolites (e.g., uridine, hypoxanthine and 5'-IMP), nicotinurate, and choline in comparison with the vehicle-treated wild-type mice. These observations are consistent with reduced lipogenesis in the liver due to tempol treatment. However, no significant change in lipid and glucose metabolism was observed in the liver of $Fxr^{\Delta IE}$ mice after tempol-treatment. In addition, antibiotic treatment significantly elevated the levels of bile acids, trimethylamine oxide (TMAO, choline, fumarate, formate, amino acids including branched chain amino acids (leucine, isoleucine and valine), alanine, glycine, tyrosine and phenylalanine, and some nucleic acids such as hypoxanthine, uridine and 5'-IMP in the liver. Compared with the vehicle-treated $Fxr^{fl/fl}$ mice, $Fxr^{\Delta IE}$ mice exhibit lower lipid and UFA levels but higher taurine and glycogen levels in the livers.

Example 15

This example demonstrates a synthesis of β-muricholic acid 9, glycine-β-muricholic acid (Gly-MCA) 16, and tauro-β-muricholic acid (T-β-MCA) 10 in accordance with an embodiment of the invention.

β-Muricholic acid (β-MCA) 9 was prepared as illustrated in FIG. 41 by following the literature procedure (Lida T, Momose T, et al., *Journal of Lipid Research,* 30: 1267-1279 (1989)). In general, esterification of the dihydroxy acid 1 with methanol under acid catalysis provided ester 2 in quantitative yield. Protection of the hydroxyl group in the 3 position with ethyl chloroformate provided carbonate 3. Oxidation of the 6-hydroxyl group with potassium chromate gave ketone 4 in quantitative yield. Bromination with 47% HBr solution gave bromo ketone 5, which on reduction with $NaBH_4$ gave bromohydrin 6 in moderate yield. Reductive dehydrobromination with zinc metal provided olefin 7 in about 80% yield. Cis-dihydroxylation with osmium tetroxide to give cis diol 8 followed by hydrolysis provided s-muricholic acid 9 in quantitative yield. r-muricholic acid 9 was conjugated with glycine to provide glycine-β-muricholic acid (Gly-MCA) 16. A suspension of ethyl glycinate was reacted with β-MCA 9 and EEDQ by refluxing overnight. The residue obtained after workup was dissolved in boiling ethanol and hydrolyzed with 10% $K_2CO_3$. The aqueous solution was acidified to give Gly-MCA 16 as a white powder in 68% yield. $^1H$ NMR ($CDCl_3$) 0.75 (s, 3H, 18-Me), 1.01 (d, 3H, J=6.5 Hz, 21-Me), 1.14 (s, 3H, 19-Me), 3.44-3.56 (m, 2H), 3.58-3.61 (m, 1H), 3.91 (s, 2H).

TβMCA 11 was similarly prepared from 9 by conjugation with taurine instead of glycine.

Example 16

This example demonstrates that Gly-MCA is stable in the intestine.

Fecal extracts were prepared as described above. Gly-MCA (50 μM) was incubated with fecal extract (0.1 mg/mL). The negative control was fecal extract alone. The positive control was fecal extract (0.1 mg/mL) and TβMCA acid (50 μM). The samples were analyzed by UPLC to determine the amount of RR-MCA (hydrolysis product) and the results shown in FIG. 35.

Gly-MCA was given to mice via oral gavage at dosages of 0, 1, 5, and 50 mg/kg of Gly-MCA, with the Gly-MCA dosed in corn oil. Gly-MCA was detected using ultra performance liquid chromatography-electrospray ionization-quadrupole time-of-flight mass spectrometry (UPLC-ESI-QTOFMS). The results are shown in FIG. 36.

As is apparent from the results shown in FIGS. 35 and 36, Gly-MCA is stable in the intestine.

Example 17

This example demonstrates that mice treated with Gly-MCA do not develop significant liver toxicity.

Mice were dosed with vehicle or Gly-MCA at 1 mg/kg, 5 mg/kg, and 50 mg/kg. After 24 h, serum aminotransferase (ALT) and aspirate aminotransferase (AST) levels were determined and the results shown in FIG. 37.

As is apparent from the results shown in FIG. 37, Gly-MCA did not exhibit significant liver toxicity at each of the doses as compared with vehicle.

Example 18

This example demonstrates that Gly-MCA significantly inhibited the FXR activity induced by the synthetic FXR agonist GW4064.

HEK293T fibroblasts were transiently co-transfected with (1) a chimeric receptor construct in which the carboxy terminal portions of human FXR (containing the native ligand-binding domain and AF2 transactivation domain) was fused to an amino terminal GAL4 DNA-binding domain under regulatory control of the constitutively active SV40 promoter, (2) a firefly luciferase reporter plasmid driven by the UAS GAL4 DNA response element, and (3) a *Renilla* luciferase reporter gene (pRL-luciferase; Promega; Madison, Wis.) as a transfection efficiency control. GW4064 or GW4064 and Gly-MCA were added to the media for 24 h, the cells were harvested, and cell extracts prepared. Luciferase detection was conducted using the Dual Luciferase Reporter Assay kit (Promega; Madison, Wis.) and a Tecan GeniosPro™ luminescent plate reader (Research Triangle Park, N.C.). The results are shown in FIG. 38.

As is apparent from the results shown in FIG. 38, Gly-MCA significantly inhibited the FXR activity induced by GW4064.

Example 19

This example demonstrates that Gly-MCA is a potent antagonist of FXR.

Differentiated Caco-2 cells were treated with 100 μM of the FXR agonist chenodeoxycholic acid (CDCA) and with 0, 100 μM, or 200 μM Gly-MCA, and expression of the FXR target gene Shp mRNA measured. As is apparent from the results shown in FIG. 39, CDCA caused a 4-fold increase in expression of Shp mRNA. Gly-MCA inhibited the induction of Shp mRNA with CDCA in a dose-dependent manner.

Differentiated Caco-2 cells were treated with 0.2 μM or 5 μM GW4064 and with 100 μM or 200 μM Gly-MCA.

Control cells were not treated with either agent. Relative expression of the FXR target gene mRNAs, Shp mRNA, Fgf19 mRNA, and Atp5g mRNA were determined and the results shown in FIGS. 40A-C, respectively. Expression of Shp mRNA and Fgf19 mRNA induced by GW4064 was blocked by Gly-MCA in a dose-dependent manner (FIGS. 40A and B). GW4064 treatment inhibited expression of the FXR target gene Atp5g mRNA and Gly-MCA reversed the inhibition (FIG. 40C).

Example 20

This example demonstrates that inhibition of FXR signaling by Gly-MCA is a potent therapeutic strategy for treatment of obesity, insulin resistance and NAFLD.

To determine whether inhibition of intestinal FXR could be a therapeutic target for high-fat diet (HFD)-induced obesity, insulin resistance and NAFLD, and confirm that this transcription factor is a suitable drug target, HFD-treated mice were orally administered Gly-MCA. Gly-MCA treatment reduced body weight gain after one week of treatment with a HFD (FIGS. 41A and B). The absolute fat mass and the fat/lean mass ratio, measured by NMR, were significantly decreased in Gly-MCA-treated mice after 7 weeks of treatment compared with vehicle-treated mice (FIGS. 41C and D). To explore the mechanism of reduced adiposity in Gly-MCA-treated mice, cumulative food intake, energy expenditure (EE) using an energy balance technique (TEE$_{bal}$: food energy intake and body composition change) were measured. Food intake was comparable between the two groups (FIG. 44A). Gly-MCA treatment increased the energy expenditure significantly, which could contribute to the decreased body weight gain of mice on a HFD compared with vehicle-treated mice (FIG. 42B). To clarify the role of Gly-MCA in obesity-related glucose homeostasis, glucose and insulin tolerance tests (GTT and ITT, respectively) were performed. The GTT revealed that after 6 weeks of HFD challenge, Gly-MCA-treated mice displayed significantly reduced blood glucose levels after glucose loading compared with vehicle-treated mice (FIGS. 43A and B). The ITT demonstrated that the insulin sensitivity was significantly increased after Gly-MCA treatment (FIG. 43C). These results indicated that Gly-MCA improved HFD-induced obesity and insulin resistance. Liver histology indicated a marked reduction in hepatic lipid droplets after Gly-MCA treatment of mice that were fed a HFD for 7 weeks (FIG. 44A). Gly-MCA treatment decreased liver weights and liver/body mass ratios (FIG. 44B). Hepatic triglyceride contents were decreased to approximately 51% in mice treated with Gly-MCA (FIG. 44D). These results indicated that Gly-MCA treatment protected mice from HFD-induced non-alcoholic fatty liver disease (NAFLD). To exclude the possibility that the effect of Gly-MCA on body weight and NAFLD were due to a non-specific toxicological effects, serum aminotransferase (ALT) and aspartate aminotransferase (AST) biomarkers of liver toxicity were determined. ALT and AST were significantly higher on a HFD and GlyMCA treatment significantly decreased serum ALT and AST levels (FIGS. 45A and B), thus indicating that the dose of Gly-MCA employed was not toxic, but actually decreased HFD-induced hepatic toxicity. NAFLD is tightly associated with bile acid metabolism. UPLC-ESI-QTOFMS-based metabolomics analysis was adopted to determine bile acid composition and levels of bile acid metabolites in the feces and intestine. A Scores scatter plot of a PCA model of the UPLC-ESI-QTOFMS negative mode data from mouse feces and ileum indicated distinct metabolic profiles between the vehicle- and Gly-MCA-treated groups (FIGS. 46A and B). The top enriched metabolite, TβMCA (m/z 514.2871, retention time=6.64 min), was increased in the Gly-MCA-treated mice on a HFD for 9 weeks as revealed in the loading scatters plot (FIGS. 46B and 47B). Levels of T-β-MCA were significantly increased whereas TCA levels were significantly decreased in feces after Gly-MCA treatment (FIG. 46C). The levels of taurine-conjugated bile acids were increased in the ileum of Gly-MCA-treated mice, notably, levels of TβMCA were significantly increased (FIG. 46C). Gly-MCA levels were markedly increased in the feces and ileum after Gly-MCA treatment for 9 weeks (FIGS. 46D and 47D, respectively). Serum triglyceride levels remained similar between the two groups on a HFD for 9 weeks (FIGS. 48A and B). Serum C16:0, C20:0, C22:0, and C24:1 ceramides levels, and ileum C16:0, C18:1, and C24:0 ceramides levels were reduced in Gly-MCA treated mice on a HFD for 9 weeks (FIGS. 49A and B). Gly-MCA treatment decreased Shp and Fgf15 mRNAs indicating that FXR signaling was inhibited in the ileum (FIG. 50A). Intestinal mRNAs encoding ceramide de novo synthesis-related genes, such as serine Sptlc3, Cers4, Degs1, and Smpd3 were significantly lower in Gly-MCA-treated mice (FIG. 50B). The expression of Shp mRNA was similar between two groups indicating that FXR signaling wasn't affected in the liver (FIG. 51A). Cyp7a1 mRNA levels were induced in Gly-MCA-treated mice (FIG. 51B). Since Fgf15 mRNA levels were lower, this might contribute to the increase of Cyp7a1 mRNA levels in Gly-MCA-treated mice. In a model of genetically-induced obesity, leptin receptor-deficient (db/db) mice treated with Gly-MCA for 6 weeks had reduced body weight as compared to vehicle-treated mice; weight loss was significant after just one week of treatment (FIG. 52). The absolute fat mass and the fat/lean mass ratio, as measured by NMR, were significantly decreased in Gly-MCA-treated db/db mice after 6 weeks of Gly-MCA treatment compared with vehicle-treated mice (FIGS. 53A and B). Liver histology indicated a significant decrease in hepatic lipid droplets after Gly-MCA treatment (FIG. 54A). Gly-MCA treatment decreased liver weights and liver/body mass ratios (FIGS. 54B and C). Liver TG contents were dramatically improved in mice treated with Gly-MCA (FIG. 54D). Gly-MCA treatment significantly decreased serum ALT and AST levels (FIGS. 55A and 55B), thus indicating that the dose of Gly-MCA employed was not toxic to the db/db mice and reduced liver toxicity in this mouse model. Levels of T-α-MCA and TβMCA were significantly increased in feces and ileum after Gly-MCA treatment (FIGS. 56A and 56B). The accumulation of Gly-MCA in the ileum is far much more than liver, feces, and serum (FIG. 56C). Serum triglyceride levels remained similar after 6 weeks of Gly-MCA treatment (FIG. 57A). Serum C16:0, C20:0, C22:0, and C24:1 ceramides levels, and ileum C16:0, C18:0, C18:1, C20:0, C22:0, C24:0 and C24:1 ceramides levels were reduced in Gly-MCA treated mice compare to vehicle treatment (FIGS. 57B and C). In another model of HFD-induced obesity, C57BL/6N mice made obese by 12 weeks of feeding a high-fat diet, were treated with Gly-MCA. Due to limited amounts of Gly-MCA, these mice were treated with only 5 mg/kg GMCA. Despite the lower dosing, they had reduced body weight gain as compared to vehicle-treated mice from two weeks of treatment (FIG. 58). The absolute fat mass, as measured by NMR, were significantly decreased in Gly-MCA-treated obese mice after 6 weeks of treatment compared with vehicle-treated mice (FIG. 59). Liver histology indicated a marked amelioration in hepatic lipid droplets after Gly-MCA treatment (FIG.

60A). Gly-MCA treatment reduced liver weights and liver/body mass ratios (FIGS. 60B and C). Levels of TαMCA and TβMCA were significantly enhanced in feces and ileum after Gly-MCA treatment (FIGS. 61A and 61B). The accumulation of Gly-MCA in the ileum is far greater than liver, feces, and serum (FIG. 61C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound selected from:

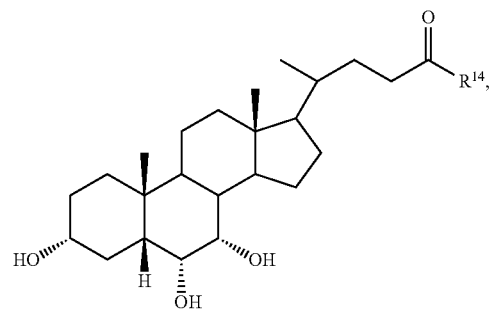

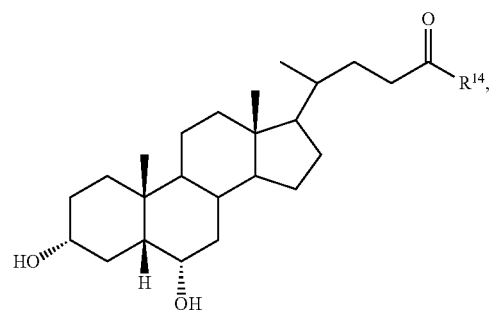

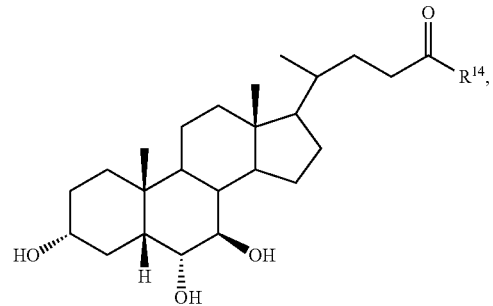

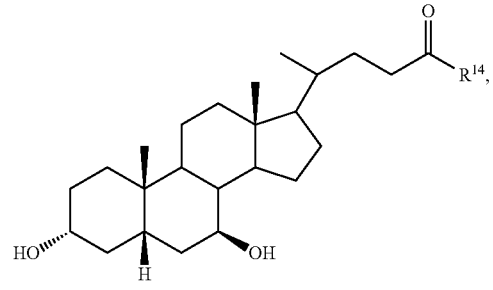

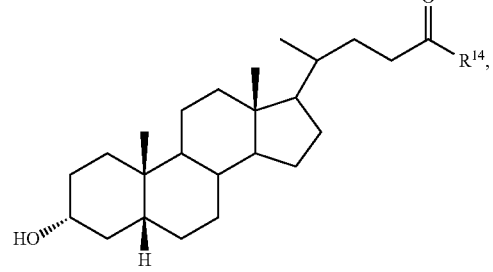

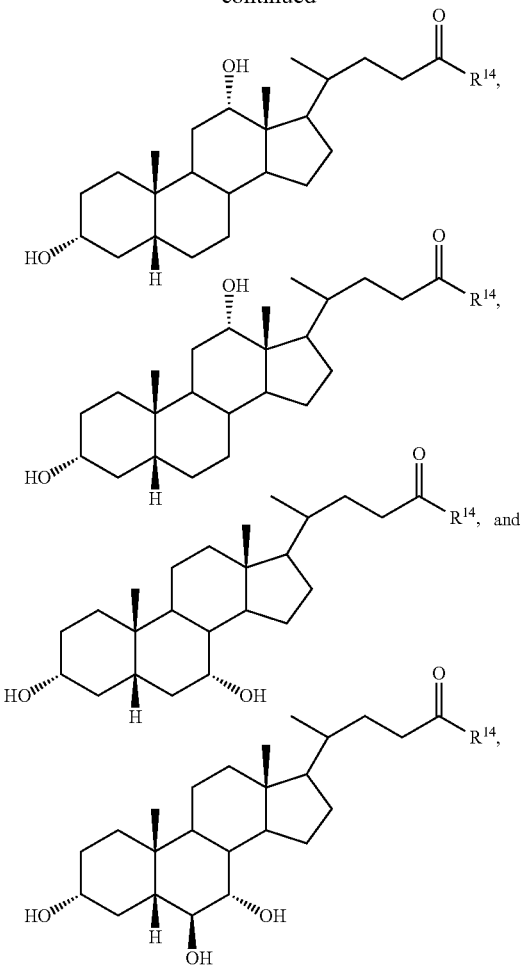

wherein R¹⁴ is selected from β-alanino, phenylalanino, tyrosino, methionino, tryptophano, leucino, isoleucino, methyl aspartato, asparto, valino, 2-fluoro-β-alanino, 2-bromoalanino, 2-chloroalanino, 2-fluoroalanino, 2-iodoalanino, 3-bromoalanino, 3-chloroalanino, 3-fluoroalanino, 3-iodoalanino, 4-bromophenylalanino, 4-chlorophenylalanino, 4-fluorophenylalanino, and 4-iodophenylalanino, or a pharmaceutically acceptable salt thereof.

2. A pharmaceutical composition comprising a pharmaceutically acceptable carrier and a compound or salt of claim 1.

3. The compound or salt of claim 1, wherein the compound is:

4. The compound or salt of claim 1, wherein the compound is:

5. The compound or salt of claim 1, wherein the compound is:

6. The compound or salt of claim 1, wherein the compound is:

7. The compound or salt of claim 1, wherein the compound is:

8. The compound or salt of claim 1, wherein the compound is:
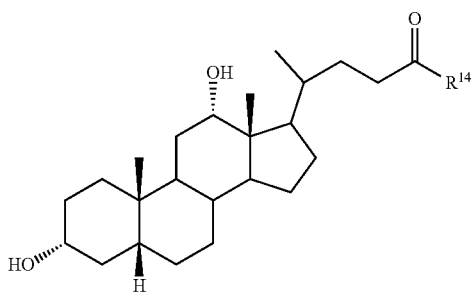
9. The compound or salt of claim 1, wherein the compound is:
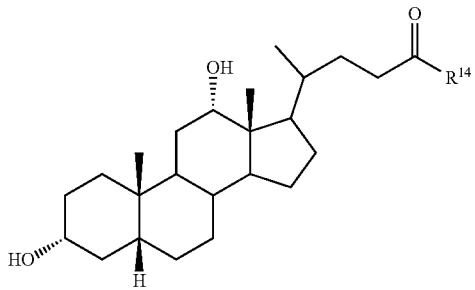
10. The compound or salt of claim 1, wherein the compound is:
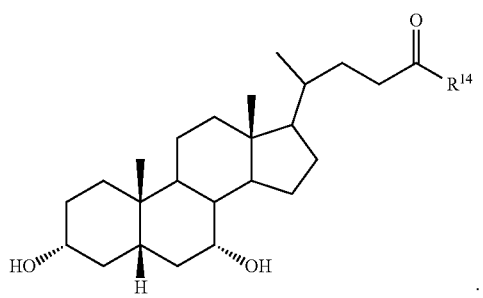
11. The compound or salt of claim 1, wherein the compound is:
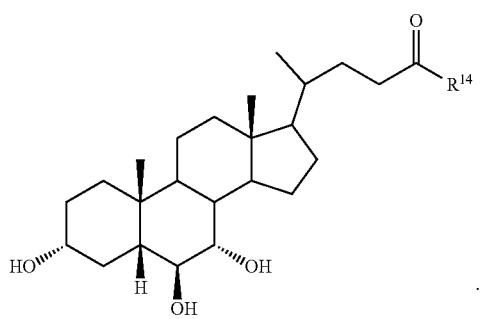
\* \* \* \* \*